(12) United States Patent
Elzinga et al.

(10) Patent No.: US 11,773,344 B2
(45) Date of Patent: Oct. 3, 2023

(54) TERPENE-BASED COMPOSITIONS, PROCESSES, METHODOLOGIES FOR CREATION AND PRODUCTS THEREBY

(71) Applicant: The Werc Shop, LLC, Monrovia, CA (US)

(72) Inventors: Sytze Elzinga, Monrovia, CA (US); Jeffrey Charles Raber, Monrovia, CA (US); Bradley J. Douglass, Monrovia, CA (US)

(73) Assignee: Scientific Holdings, LLC, Monrovia, CA (US)

( * ) Notice: Subject to any disclaimer, the term of this patent is extended or adjusted under 35 U.S.C. 154(b) by 172 days.

(21) Appl. No.: 17/002,666

(22) Filed: Aug. 25, 2020

(65) Prior Publication Data

US 2021/0017468 A1   Jan. 21, 2021

Related U.S. Application Data

(63) Continuation of application No. 14/467,565, filed on Aug. 25, 2014, now Pat. No. 10,774,288.

(60) Provisional application No. 61/879,281, filed on Sep. 18, 2013.

(51) Int. Cl.
| | |
|---|---|
| *C11B 9/00* | (2006.01) |
| *A23L 27/20* | (2016.01) |
| *A61K 31/015* | (2006.01) |
| *A61K 31/01* | (2006.01) |
| *C40B 30/00* | (2006.01) |
| *A23L 5/00* | (2016.01) |
| *A23L 27/10* | (2016.01) |
| *C11B 9/02* | (2006.01) |
| *G01N 33/00* | (2006.01) |

(52) U.S. Cl.
CPC .............. *C11B 9/0007* (2013.01); *A23L 5/51* (2016.08); *A23L 27/115* (2016.08); *A23L 27/202* (2016.08); *A23L 27/203* (2016.08); *A23L 27/2026* (2016.08); *A61K 31/01* (2013.01); *A61K 31/015* (2013.01); *C11B 9/0034* (2013.01); *C11B 9/0038* (2013.01); *C11B 9/0046* (2013.01); *C11B 9/0049* (2013.01); *C11B 9/022* (2013.01); *C40B 30/00* (2013.01); *G01N 33/00* (2013.01); *A23V 2200/15* (2013.01); *A23V 2200/16* (2013.01); *A23V 2250/21* (2013.01)

(58) Field of Classification Search
CPC . A23L 1/00; A23L 27/202; C11B 1/00; C11B 9/0007; A61K 31/01; A61K 31/015
See application file for complete search history.

(56) References Cited

U.S. PATENT DOCUMENTS

2003/0021883 A1*  1/2003  Skiff ........................ C11B 9/022
426/651

OTHER PUBLICATIONS

"Essential oils of different cultivars of *Cannabis sativa* L. and their antimicrobial activity," Novak et al., Flavour Fragr. J. 2001;16:259-62. (Year: 2001).*

"Chemical composition of essential oils of hops (*Humulus lupulus* L.) growing wild in Aukstaitija," Bernotienė et al., CHEMIJA 2004; 15(2):31-36. (Year: 2004).*

* cited by examiner

*Primary Examiner* — Theodore R. Howell
(74) *Attorney, Agent, or Firm* — JD Harriman

(57) ABSTRACT

Compositions which are fragrant and contain at least a member set culled from a library of compositions, each being comprised of sub-combinations of selected terpenes. Fragrances that mimic that of various states of organic and synthetic aromatics including products, processes and those from non-combusted plant products, among other things, uniquitous products, processes, medicinals, and related moieties leverage databases of all known terpene groupings are offered for consideration, and have been provided, according to the instant teachings.

21 Claims, 2 Drawing Sheets

TERPENE-BASED COMPOSITIONS, PROCESSES, METHODOLOGIES FOR CREATION AND PRODUCTS THEREBY

This application claims priority to U.S. Provisional Patent Application 61/879,281 filed on Sep. 18, 2013 and U.S. patent application Ser. No. 14/467,565 filed on Aug. 25, 2014, both of which are incorporated by reference herein in their entirety.

BACKGROUND OF THE SYSTEM

Field of the Disclosure

The present disclosure relates to compositions, and related methods, that comprise defined mixtures of terpenes that have a distinctive fragrance that mimics that of non-combusted plant products, intermediates, and related moieties.

Background of the Disclosure

The fragrant oils of oranges and lemons are used as aroma flavors in beverages, ice cream, gelatins, as well as in perfumes and soaps. Cloves, which contain aromatic oils, stimulated the establishment of global commerce between Asia and Europe. The major volatile constituent of cloves, eugenol, is used in perfumes, ice cream, baked goods, and candy. Peppermint, which also contains aromatic oils, is used in the manufacture of chewing gum, candies, and toothpaste. It is interesting that peppermint is a sterile hybrid and that it is a cross between mint and spearmint, and that according to legend, Minthe (a female spirit) of the river Cocytus, was converted by Persephone into a mint plant. Aromatic gums from frankincense and myrrh were commodities in Persia, Mesopotamia, Egypt, Greece, and Rome, as early as 1000 BC, where the gums were derived from trees growing in arid regions of Arabia. Presently, frankincense and myrrh are used in perfumes and cosmetics (Bourgou et al (2012) Scientific World J. ID 528593 (10 pages); Gershenzon et al (2000) Plant Physiol. 122:205-213; Kamatou et al (2012) Molecules. 17:6953-6981; W. Seller, M. Watt (2004) Frankincense and Myrrh, Random House Books, UK; Hillson (1988) J. Royal Soc. Med. 81:542-543; Coder (December 2011) Frankincense & Myrrh, Trees and Culture Series, Univ. Georgia; Anonymous (1829) A Commentary Mythological, Historical, and Geographical on Pope's Homer and Dryden's Aeneid of Virgil, John Murray, London, page 317).

The fragrant components of the oils in the above-mentioned commodities are largely terpenes. Terpenes are also known as terpenoids. In citrus fruits, the major aromatic compounds are limonene and 1,8-cineole (also called eucalyptol), which are both terpenes. The aromatic compounds of clove oil include eugenol and beta-caryophillene, which are terpenes. The aromatic compounds of peppermint include limonene, menthone, and menthol, which are all terpenes. The main terpenes in frankincense are E-beta-ocimene and limone (Al-Harrasi and Al-Saidi (2008) Molecules. 13:2181-2189). Myrrh contains the terpenes, lindestrene and furanoeudesma-1,3-diene, which represent the odor of unprocessed myrrh (Nanus et al (2005) Biomed. Papers. 149:3-28).

The founder of terpene chemistry is Otto Wallach who received the Nobel Prize in 1910 (Christmann (2010) Angew Chem. Int. Ed. Engl. 49:9580-9586). The terpenes are classified as "natural products." They are biosynthesized from units of isoprene, which can be linked to form linear chains or rings. In increasing length, the terpenes include hemiterpenes (single isoprenoid unit), monoterpenes (two units), sesquiterpenes (three units), diterpenes (four units), sesterterpenes (five units), triterpenes (six units), and so on. Non-aromatic terpenes include vitamin A, vitamin K, and the taxanes. The taxanes (diterpenes), such as paclitaxel, are renowned for their use in treating cancer (Heinig and Jennewein (2009) African J. Biotech. 8:1370-1385).

Some examples of terpenes, and their classification, are as follows:

Hemiterpenes: Examples of hemiterpenes, which do not necessarily have an odor, are 2-methyl-1,3-butadiene, hemialboside, and hymenoside;

Monoterpenes: pinene; alpha-pinene, beta-pinene, cis-pinane, trans-pinane, cis-pinanol, trans-pinanol (Erman and Kane (2008) Chem. Biodivers. 5:910-919), limonene; linalool; myrcene; eucalyptol; alpha-phellandrene; beta-phellandrene; alpha-ocimene; beta-ocimene, cis-ocimene, ocimene, delta-3-carene; fenchol; sabinene, borneol, isoborneol, camphene, camphor, phellandrene, alpha-phellandrene, alpha-terpinene, geraniol, linalool, nerol, menthol, myrcene, terpinolene, alpha-terpinolene, beta-terpinolene, gamma-terpinolene, delta-terpinolene, alpha-terpineol, trans-2-pinanol, Sesquiterpenes: caryophyllene; beta-caryophyllene, caryophyllene oxide, humulene, alpha-humulene, alpha-bisabolene; beta-bisabolene; santalol; selinene; nerolidol, bisabolol; alpha-cedrene, beta-cedrene, beta-eudesmol, eudesm-7(11)-en-4-ol, selina-3,7(11)-diene, guaiol, valencene, alpha-guaiene, beta-guaiene, delta-guaiene, guaiene, farnesene, alpha-farnesene, beta-farnesene, elemene, alpha-elemene, beta-elemene, gamma-elemene, delta-elemene, germacrene, germacrene A, germacrene B, germacrene C, germacrene D, germacrene E.

Diterpenes: oridonin,

Triterpenes: ursolic acid; oleanolic acid;

"1.5 ene": guaia-1(10),11-diene can be characterized as a 1.5 ene. Guaia-1(10),11-diene is halfway between a monoterpene and diterpene, in terms of how many isoprenoid units are present. Monoterpene is $C_{10}H_{16}$, and diterpene is $C_{20}H_{32}$. Guaia-1(10),11-diene is $C_{15}H_{24}$. Isoprene is $C_{0.5}H_{0.8}$ (two double bonds).

The present disclosure provides formulations that include one or more of these terpenes. In exclusionary embodiments, the present disclosure can also exclude one or more of any terpene that is disclosed herein, and/or related plant materials, depending on intended applications, inter alia.

The present disclosure provides compositions, comprising novel combinations of terpenes that mimic the fragrance of plant matter that is processed or dried. Also provided are novel combinations of terpenes that mimic a documented emotional response that is conferred by the processed or dried plant matter, or provides any number of utilitarian benefits, real or perceived.

SUMMARY

The present disclosure provides a composition that contains a combination of selected terpenes. The composition has a fragrance that mimics that of a non-combusted plant product, as determinable, for example, by a human odor panel or by a synthetic nose. Human testers describe embodiments of the invention as having memorable, distinct and generally pleasant odors. One embodiment of the composition is described as having sweet citrus odors, as well as woody or earthy overtones. The embodiment has a fragrance which may also be described as having a lightly floral, fruity, flowery, lemony, or the like.

The invention provides compositions comprising terpene formulations. The terpene formulations may comprise one or more selected from a list comprising alpha-bisabolol, borneol, camphene, camphor, beta-caryophyllene, delta-3-carene, caryophyllene oxide, alpha-cedreen, beta-eudesmol, fenchol, geraniol, guaiol, alpha-humulene, isoborneol, limonene, linalool, menthol, myrcene, nerol, cis-ocimene, trans-ocimene, alpha-phellandrene, alpha-pinene, beta-pinene, sabinene, alpha-terpinene, alpha-terpineol, terpinolene, alpha-guaiene, elemene, farnesene, germacrene B, guaia-1(10),11-diene, trans-2-pinanol, Selina-3,7(11)-diene, eudesm-7(11)-en-4-ol, and valencene. In embodiments, the terpene formulation has a detectable fragrance. The various terpene formulations are described in more detail below.

In an embodiment, the invention comprises a prepared composition of terpenes comprising beta-caryophyllene, limonene, and myrcene, wherein the composition has a detectable fragrance. The fragrance can be detected, for example, by a human olfactory system or a synthetic nose.

Also provided is the above composition further comprising one or more selected from a list comprising alpha-bisabolol, borneol, camphene, camphor, delta-3-carene, caryophyllene oxide, alpha-cedreen, beta-eudesmol, fenchol, geraniol, guaiol, alpha-humulene, isoborneol, linalool, menthol, nerol, cis-ocimene, trans-ocimene, alpha-phellandrene, alpha-pinene, beta-pinene, sabinene, alpha-terpinene, alpha-terpineol, terpinolene, alpha-guaiene, elemene, farnesene, germacrene B, guaia-1(10),11-diene, trans-2-pinanol, Selina-3,7(11)-diene, eudesm-7(11)-en-4-ol, and valencene.

Also provided is a composition comprising beta-caryophyllene, limonene, myrcene, alpha-pinene, and linalool, wherein the terpenes are present in approximately equal percentages by weight (wt %).

In another embodiment, the invention provides a composition comprising beta-caryophyllene at about 10-30 wt %, limonene at about 5-45 wt %, and myrcene at about 5-30 wt %; and wherein the sum of all terpenes in the composition is 100 wt %.

In an embodiment, the present disclosure provides a composition comprising a terpene formulation, wherein the terpene formulation consists of beta-caryophyllene, limonene, myrcene, and at least one other terpene, wherein the composition does not contain 3,3'-dihydroxy-5,4'-dimethoxybibenzyl, wherein the terpene formulation is the only source of terpenes in the composition, and wherein the beta-caryophyllene, limonene, and myrcene together comprise at least 25% (wt./vol.) of the terpene formulation, or at least 30%, at least 35%, at least 40%, at least 45%, at least 50%, at least 55%, at least 60%, at least 65%, at least 70%, at least 75%, at least 80%, at least 85%, at least 90%, of the terpene composition.

Also provided is a prepared composition of terpenes comprising myrcene and alpha-pinene, wherein the composition has a detectable fragrance. Also provided is the above composition further comprising one or more selected from a list comprising alpha-bisabolol, borneol, camphene, camphor, beta-caryophyllene, delta-3-carene, caryophyllene oxide, alpha-cedreen, beta-eudesmol, fenchol, geraniol, guaiol, alpha-humulene, isoborneol, limonene, linalool, menthol, nerol, cis-ocimene, trans-ocimene, alpha-phellandrene, beta-pinene, sabinene, alpha-terpinene, alpha-terpineol, terpinolene, alpha-guaiene, elemene, farnesene, germacrene B, guaia-1(10),11-diene, trans-2-pinanol, Selina-3,7(11)-diene, eudesm-7(11)-en-4-ol, and valencene.

In an embodiment, the invention provides a composition wherein myrcene is present at about 20-95 wt %; and alpha-pinene is present at about 5-35 wt %; and wherein the sum of all terpenes in the composition is 100 wt %.

In another embodiment, the composition comprises a modifier. The modifier (described in more detail below) may comprise a thiol, an ester, a ketone, an aldehyde, a cannabinoid, another compound, or any combination thereof.

In an exclusionary embodiment, the invention provides any of the above compositions, wherein the composition does not contain 3,3'-dihydroxy-5,4'dimethoxybibenzyl. In another exclusionary embodiment, the invention provides any of the above compositions, wherein the composition does not contain cellulose. In another exclusionary embodiment, the invention provides any of the above compositions, wherein the composition does not contain chlorophyll.

Also provided is any of the above compositions, wherein the each terpene is either purified from a natural source or is synthetic.

Also provided a composition wherein the terpene formulation consists of beta-caryophyllene, limonene, myrcene, alpha-pinene, and linalool. Also provided is the above composition, wherein the terpene formulation consists of beta-caryophyllene, limonene, myrcene, beta-pinene, and linalool. Also provided is the above composition, wherein the terpene formulation consists of beta-caryophyllene, limonene, myrcene, and terpinolene. Also provided is the above composition, wherein the terpene formulation consists of beta-caryophyllene, limonene, myrcene, terpinolene, and beta-pinene.

Also provided is the above composition, wherein the formulation consists of about 20% (wt./vol.) beta-caryophyllene, about 42% (wt./vol.) limonene, about 24% (wt./vol.) myrcene, and about 14% (wt./vol.) at least one other terpene, and wherein the sum of the equals 100%. Also provided is the above composition, wherein the formulation consists of about 20% (wt./vol.) beta-caryophyllene, about 42% (wt./vol.) limonene, about 24% (wt./vol.) myrcene, about 7% (wt./vol.) beta-pinene, and about 7% (wt./vol.) linalool, and wherein the sum of the % equals 100%.

Also provided is the above composition, wherein the terpene formulation consists of about 22% (wt./vol.) beta-caryophyllene, about 9% (wt. vol.), limonene, about 7% (wt./vol.) myrcene, and about 61% (wt./vol.) terpinolene, and that does not contain any linalool, and wherein the sum of the % equals 100%. In another aspect, what is provided is the above composition, wherein the terpene formulation consists of about 21% (wt./vol.) beta-caryophyllene, about 9% (wt./vol.), limonene, about 6% (wt./vol.) myrcene, about 7% beta-pinene, and about 57% (wt./vol.) terpinolene, and that does not contain any linalool, and wherein the sum of the % equals 100%.

Further embraced, is the above composition, wherein the terpene formulation consists of about 20% (wt./vol.) beta-caryophyllene, about 8% (wt. vol.) limonene, about 6% (wt./vol.) myrcene, about 7% beta-pinene, about 6% ocimene, and about 53% (wt./vol.) terpinolene, and that does not contain any linalool, and wherein the sum of the equals 100%. Moreover, what is also provided is the above composition, wherein the beta-caryophyllene, limonene, and myrcene together comprise at least 35% (wt./vol.) of the terpene formulation.

In another composition embodiment, what is provided is a composition comprising a terpene formulation, wherein the terpene formulation consists of myrcene, alpha-pinene, and at least one other terpene, wherein the composition does not contain 3,3'-dihydroxy-5,4'-dimethoxybibenzyl, wherein the terpene formulation is the only source of terpenes in the composition, wherein the myrcene and alpha-pinene together comprise at least 25% (wt./vol.) of the terpene formulation, or at least 30%, at least 35%, at least 40%, at least 45%, at least 50%, at least 55%, at least 60%, at least 65%, at least 70%, at least 75%, at least 80%, at least 85%, at least 90%, of the terpene composition. Also provided is the above composition, wherein the terpene formulation consists of myrcene, alpha-pinene, and: (i) beta-pinene, (ii) beta-caryophyllene, or (iii) beta-pinene and beta-caryophyllene. In another aspect, what is provided is the above composition, wherein the terpene formulation consists of about 94% (wt./vol.) myrcene, about 6% (wt./vol.) alpha-pinene, and wherein the sum of the % equals 100%. What is embraced, is the above composition, wherein the terpene formulation consists of about 91% (wt./vol.) myrcene, about 6% (wt./vol.) alpha-pinene, and about 3% (wt./vol.) beta-pinene, and wherein the sum of the % equals 100%.

Moreover, what is provided is the above wherein the terpene formulation consists of about 91% (wt./vol.) myrcene, about 6% (wt./vol.) alpha-pinene, and about 3% (wt./vol.) beta-caryophyllene, and wherein the sum of the % equals 100%. Also provided is the above composition, wherein the myrcene and alpha-pinene together comprise at least 35% (wt./vol.) of the terpene formulation.

In embodiments that refer to the tables, what is provided is a composition comprising a formulation that includes one of the terpene trios that are disclosed in Tables 2-37, wherein the terpene formulation is the only source of terpenes in the composition, wherein the terpene trio accounts for at least 40% of the terpenes of the formulation (or at least 45%, at least 50%, at least 55%, at least 60%, at least 65%, at least 70%, at least 75%, at least 80%, at least 85%, at least 90%, at least 95%), and wherein each terpene is either purified from a natural source or is synthetic. Also provided is the above composition, wherein the terpene trio accounts for at least 70% of the terpenes of the formulation. Further provided is the above composition, wherein the terpene trio accounts for at least 80% of the terpenes of the formulation.

Also provided is the above composition, wherein the formulation does not contain any terpene in addition to the terpenes in the terpene trio. Moreover, what is embraced is the above composition, wherein the terpene trio is beta-caryophyllene, limonene, and myrcene. In yet another embodiment, what is provided is the above composition, wherein the terpene trio is beta-caryophyllene, limonene, and myrcene, and wherein the formulation additionally comprises: (i) Beta-pinene, or (ii) Linalool, or (iii) Both beta-pinene and linalool.

Further provided is the above composition, wherein the terpene trio is beta-caryophyllene, limonene, and myrcene, and wherein the formulation additionally comprises beta-pinene and terpinolene, and does not include linalool. Further provided is the above composition, that comprises myrcene, alpha-pinene, and: (i) beta-pinene; or (ii) beta-caryophyllene; or (iii) both beta-pinene and beta-caryophyllene. In exclusionary embodiments, what is provided is the above composition that does not contain more than four terpenes. Moreover, what is provided is the above composition that does not contain more than five terpenes.

In device embodiments, what is provided is a device comprising one of the above-disclosed compositions. In other device embodiments, what is provided is the above device that is a wax candle, a container or wrapper that comprises a soap, a container that comprises a perfume, a container that comprises a cosmetic creme, an electronic cigarette, a scratch and sniff device, an edible substance, a tincture, or a container holding a pressurized composition that is configured for aerosol dispersal.

In a methods embodiment, what is provided is a method for applying a fragrance, the method comprising providing a composition of terpenes, contacting an olfactorily detectable quantity of the composition with the atmosphere, and causing a human olfactory system or electronic nose to detect the presence of the composition in the atmosphere. The method may further comprising contacting the olfactorily detectable quantity of composition with a carrier substance, which may comprise a perfume, incense, cosmetic, moisturizer, emollient, toiletry, edible substance, inhalable substance, electronic cigarette liquid, or candle.

In a methods embodiment, what is provided is a method for using one of the above compositions, comprising the step of contacting the composition with the atmosphere, the step of allowing a detectable quantity of vaporize and migrate into the atmosphere, and the step of inhaling by a human subject of at least a portion of the detectable quantity, wherein the detectable quantity can be detected by one or both of an olfactory system or by an electronic nose.

In other embodiments, what is provided is an apparatus for dispensing at least a fragranted terpene-based composition according to any claims, tables, and the specification, including said terpene-based fragranted composition disposed or effective to be emplaced therein. In a process embodiment, what is provided is a process to impart any terpene-based fragranted compositions in whole, or in part to a perfume, flavor material, incense, cosmetic or toiletry, according to any claims, tables, and the specification above. In a system embodiment, what is provided is a system for repelling or attracting olfactorily sentient organisms based upon the claims, tables, and the specification above. In another system embodiment, what is provided is a system for addressing masking of odors, according to any claims, tables, or disclosures herein comprised of at least one prepared version of a terpene-based composition. In products by process embodiments, what is provided is a products by processes of any claims herein. Moreover, what is provided is a product, according to the tables and specification herein, for treating mammals in need thereof.

What is provided is a composition comprising a terpene formulation, wherein the terpene formulation consists of beta-caryophyllene, limonene, myrcene, and at least one other terpene that is not alpha-pinene, wherein the composition does not contain 3,3'-dihydroxy-5,4'-dimethoxybibenzyl, and wherein the terpene formulation is the only source of terpenes in the composition.

In embodiments, what can be excluded is any composition, any formulation, any composition containing said formulation, and related methods, wherein the composition is a fluid (or comprises mainly fluid, or where about 80% of the entire composition is fluid, or where about 60% of the entire composition is fluid, or where about 40% of the entire composition is fluid), and wherein the fluid component of the composition contains less than 10% (wt./vol.), less than 1.0%, less than 0.5%, less than 0.2%, less than 0.1%, less than 0.05%, less than 0.02%, less than 0.01%, less than 0.005%, less than 0.002%, less than 0.001%, less than 0.0005%, less than 0.0002%, less than 0.0001%, less than 0.00001%, less than 0.000001%, less than 0.0000001%, and the like, 3,3'-dihydroxy-5,4'-dimethoxybibenzyl. Also, what can be excluded is a composition where the fluid component of the composition contains detectable 3,3'-dihydroxy-5,4'-dimethoxybibenzyl, and where the detectable 3,3'-dihydroxy-5,4'-dimethoxybibenzyl occurs at a concentration that is less than 1.0%, less than 0.5%, less than 0.2%, less than 0.1%, less than 0.05%, less than 0.02%, less than 0.01%, less than 0.005%, less than 0.002%, less than 0.001%, less than 0.0005%, less than 0.0002%, less than 0.0001%, less than 0.00001%, less than 0.000001%, less than 0.0000001%, and the like.

The above exclusionary embodiments can also apply to one or more other chemicals, such as terpenes or non-terpenes.

In other exclusionary embodiments, what can be excluded is any composition that is a fluid, where in the composition contains more than 10% (wt./vol.), more than 1.0%, more than 0.5%, more than 0.2%, more than 0.1%, more than 0.05%, more than 0.02%, more than 0.01%, more than 0.005%, more than 0.002%, more than 0.001%, more than 0.0005%, more than 0.0002%, more than 0.0001%, and the like, of 3,3'-dihydroxy-5,4'-dimethoxybibenzyl.

What is provided is a composition comprising a terpene formulation, wherein the terpene formulation consists of beta-caryophyllene, limonene, myrcene, and at least one other terpene that is not alpha-pinene, wherein the composition does not contain alpha-pinene, and wherein the terpene formulation is the only source of terpenes in the composition.

Also provided is the above composition, wherein each one of the terpenes is either purified from a natural source or is synthetic. Also provided is the above composition, wherein the terpene formulation consists of beta-caryophyllene, limonene, myrcene, beta-pinene, and linalool.

Also provided is the above composition, wherein the terpene formulation consists of beta-caryophyllene, limonene, myrcene, and terpinolene. Also provided is the above composition, wherein the terpene formulation consists of beta-caryophyllene, limonene, myrcene, terpinolene, and beta-pinene.

Also provided is the above composition, wherein the formulation consists of about 20% (wt./vol.) beta-caryophyllene, about 42% (wt./vol.) limonene, about 24% (wt./vol.) myrcene, and about 14% (wt./vol.) at least one other terpene, and wherein the sum of the % equals 100%.

Also provided is the above composition, wherein the formulation consists of about 20% (wt./vol.) beta-caryophyllene, about 42% (wt./vol.) limonene, about 24% (wt./vol.) myrcene, about 7% (wt./vol.) beta-pinene and about 7% (wt./vol.) linalool, and wherein the sum of the % equals 100%.

In embodiments not containing the term "about," what is provided is the above composition, wherein the formulation consists of 20% (wt./vol.) beta-caryophyllene, 42% (wt./vol.) limonene, 24% (wt./vol.) myrcene, 7% (wt./vol.) beta-pinene and 7% (wt./vol.) linalool, and wherein the sum of the % equals 100%.

Also provided is the above composition, wherein the terpene formulation consists of about 22% (wt./vol.) beta-caryophyllene, about 9% (wt. vol.), limonene, about 7% (wt./vol.) myrcene, and about 61% (wt./vol.) terpinolene, and that does not contain any linalool, and wherein the sum of the % equals 100%.

In embodiments not containing the term "about," what is also provided is the above composition, wherein the terpene formulation consists of 22% (wt./vol.) beta-caryophyllene, 9% (wt. vol.), limonene, 7% (wt./vol.) myrcene, and 61% (wt./vol.) terpinolene, and that does not contain any linalool, and wherein the sum of the % equals 100%.

Further contemplated is the above composition, wherein the terpene formulation consists of about 21% (wt./vol.) beta-caryophyllene, about 9% (wt. vol.), limonene, about 6% (wt./vol.) myrcene, about 7% beta-pinene, and about 57% (wt./vol.) terpinolene, and that does not contain any linalool, and wherein the sum of the % equals 100%.

In an alternate embodiment that does not contain the term "about," what is provided is the above composition, wherein the terpene formulation consists of 21% (wt./vol.) beta-caryophyllene, 9% (wt. vol.), limonene, about 6% (wt./vol.) myrcene, 7% beta-pinene, and 57% (wt./vol.) terpinolene, and that does not contain any linalool, and wherein the sum of the % equals 100%.

What is further embraced is the above composition, wherein the terpene formulation consists of about 20% (wt./vol.) beta-caryophyllene, about 8% (wt. vol.), limonene, about 6% (wt./vol.) myrcene, about 7% beta-pinene, about 6% ocimene, and about 53% (wt./vol.) terpinolene, and that does not contain any linalool, and wherein the sum of the % equals 100%.

Also encompassed is the following embodiment that does not contain the term "about," namely, the above composition, wherein the terpene formulation consists of 20% (wt./vol.) beta-caryophyllene, 8% (wt. vol.), limonene, 6% (wt./vol.) myrcene, 7% beta-pinene, 6% ocimene, and 53% (wt./vol.) terpinolene, and that does not contain any linalool, and wherein the sum of the % equals 100%.

In yet another embodiment, what is embraced is a composition comprising a terpene formulation, wherein the terpene formulation consists of myrcene, alpha-pinene, and at least one other terpene that is not limonene, wherein the composition does not contain limonene, and wherein the terpene formulation is the only source of terpenes in the composition.

In yet another embodiment, what is embraced is a composition comprising a terpene formulation, wherein the terpene formulation consists of myrcene, alpha-pinene, and at least one other terpene that is not limonene, wherein the composition does not contain 3,3'-dihydroxy-5,4'-dimethoxybibenzyl, and wherein the terpene formulation is the only source of terpenes in the composition.

In another aspect, what is provided is the above composition, wherein the terpene formulation consists of myrcene, alpha-pinene, and: (i) beta-pinene, (ii) beta-carophyllene, or (iii) beta-pinene and beta-carophyllene.

In yet another aspect, what is provided is the above composition, wherein the terpene formulation consists of about 94% (wt./vol.) myrcene, about 6% (wt./vol.) alpha-pinene, and wherein the sum of the % equals 100%.

In an embodiment not containing the term "about," what is embraced is the above composition, wherein the terpene formulation consists of 94% (wt./vol.) myrcene, 6% (wt./vol.) alpha-pinene, and wherein the sum of the % equals 100%.

In another aspect, what is provided is the above composition, wherein the terpene formulation consists of about 91% (wt./vol.) myrcene, about 6% (wt./vol.) alpha-pinene, and about 3% (wt./vol.) beta-pinene, and wherein the sum of the % equals 100%. Also provided is the above composition, wherein the terpene formulation consists of 91% (wt./vol.) myrcene, 6% (wt./vol.) alpha-pinene, and 3% (wt./vol.) beta-pinene, and wherein the sum of the % equals 100%.

Moreover, what is embraced is the above composition, wherein the terpene formulation consists of about 91% (wt./vol.) myrcene, about 6% (wt./vol.) alpha-pinene, and about 3% (wt./vol.) beta-caryophyllene, and wherein the sum of the % equals 100%. Also embraced is the above composition, comprising a formulation that includes one of the terpene trios that are disclosed in Tables 2-37, wherein the terpene formulation is the only source of terpenes in the composition, wherein the terpene trio accounts for at least 60% of the terpenes of the formulation, and wherein each terpene is either purified from a natural source or is synthetic. Table 1 is a legend that correlates the number used to refer to a terpene, with the actual name of the terpene.

Moreover, what is encompassed is the above composition, wherein the terpene trio accounts for at least 70% of the terpenes of the formulation. Also embraced is the above composition, wherein the terpene trio accounts for at least 80% of the terpenes of the formulation. Further provided is the above composition, wherein the formulation does not contain any terpene in addition to the terpenes in the terpene trio. Additionally encompassed is the above composition, wherein the terpene trio is beta-caryophyllene, limonene, and myrcene. Further provided is the above composition, wherein the terpene trio is beta-caryophyllene, limonene, and myrcene, and wherein the formulation additionally comprises: (i) Beta-pinene, or (ii) Linalool, or (iii) Both beta-pinene and linalool.

In another aspect, what is provided is the above composition, wherein the terpene trio is beta-caryophyllene, limonene, and myrcene, and wherein the formulation additionally comprises beta-pinene and terpinole, and does not include linalool. In another aspect, what is provided is the above composition, that comprises myrcene, alpha-pinene, and: (i) beta-pinene; or (ii) beta-caryophyllene; or (iii) both beta-pinene and beta-caryophyllene, In embodiments that limit the number of terpenes, what is provided is each and every one of the above compositions, wherein the composition does not contain more than four terpenes, wherein the composition does not contain more than five terpenes, wherein the composition does not contain more than six terpenes, and so on.

In device embodiments, what is provided for each of the above-disclosed compositions, that is, provided separately for each and every one of the above compositions, is a device that comprises the composition. The device can be a holder, a vial, a bottle, a canister, a paper wrapper, a foil wrapper, a plastic wrapper, and so on. The device can be a wax candle, a container or wrapper that comprises a soap, a container that comprises a perfume, a container that comprises a cosmetic creme, an electronic cigarette, a scratch and sniff device, an edible substance, a tincture, or a container holding a pressurized composition that is configured for aerosol dispersal.

Also provided is a process for generating a library of prepared terpene compositions, the process comprising: obtaining a sample; analyzing a chemical profile of the sample to identify terpenes in the sample; quantifying the terpenes identified; and preparing a blend of terpenes based on those quantities. The sample can be from any plant or other natural product, including *Cannabis sativa, Humulus lupulus*, or other plants. The analysis step may comprise separating substances from a mixture, genetic analysis, chemotaxonomic analysis, compound extraction, gas chromatography flame ionization detection, chemical formula identification, chromatography, or any other analytical chemistry technique known in the art. Terpenes identified can be those listed in Tables 1-37 below, or any other terpene. Terpenes may be quantified based on their mass fraction, percent weight, mole fraction, percentage by volume, or the like. The prepared blend may comprise all natural terpenes, all synthetic terpenes, or a combination thereof.

Also provided is a database or library of terpene compositions produced by the above process.

The present disclosure encompasses all possible combinations of the above embodiments, and encompasses all possible disclosures of each independent claim with its dependent claims. For example, what is encompassed is an invention that is the combination of: Claim 1+Claim 2; or the combination of: Claim 1+Claim 2+Claim 3; or the combination of Claim 1+Claim 3+Claim 4; or the combination of Claim 1+Claim 2+Claim 3+Claim 4; and the like.

As used herein, including the appended claims, the singular forms of words such as "a," "an," and "the" include their corresponding plural references unless the context clearly dictates otherwise. All references cited herein are incorporated by reference to the same extent as if each individual publication, patent, and published patent application, as well as figures and drawings in said publications and patent documents, was specifically and individually indicated to be incorporated by reference.

The terms "adapted to," "configured for," and "capable of," mean the same thing. Where more than one of these terms are used in a claim set, it is the case that each and every one of these terms, as they might occur, means, "capable of."

DETAILED DESCRIPTION OF THE SYSTEM

Definitions and Methods

Figure 1:
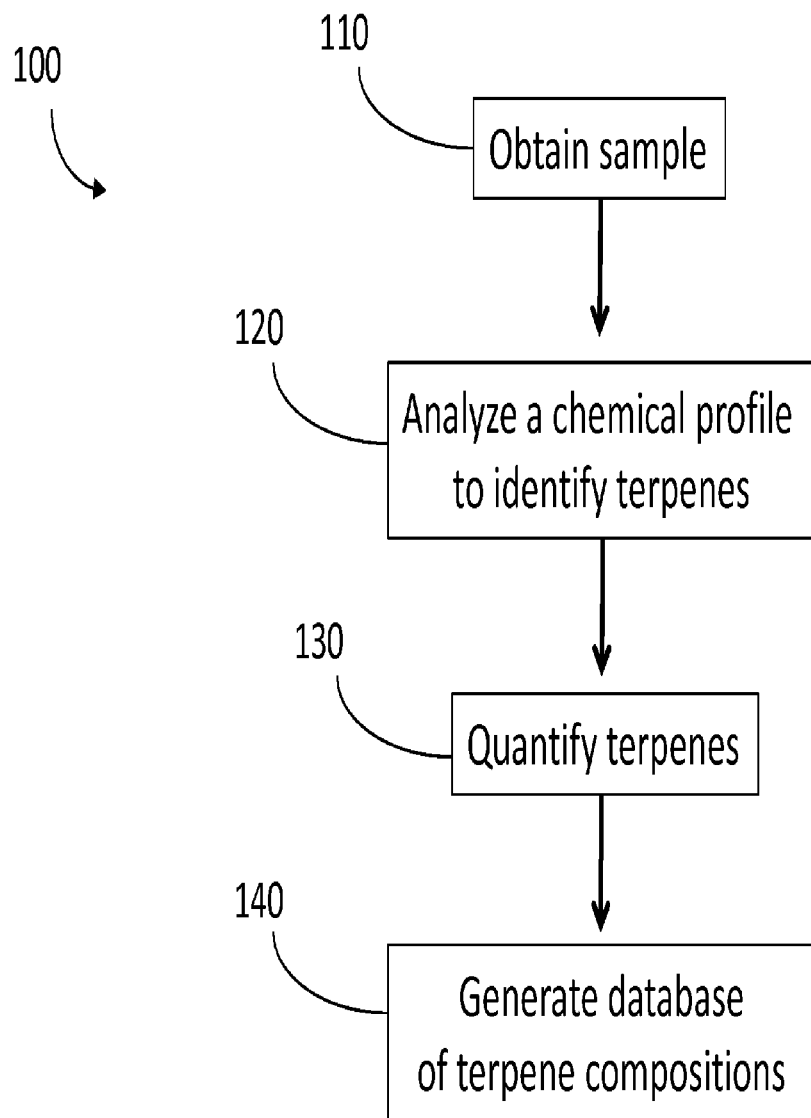
FIG. 1 shows a method for generating a library of prepared terpene compositions.

An "agonist" is a compound that stimulates an increase in a biochemical or physiological activity. The activity can be the rate of ion transport by an ion channel, rate of signal transmission by a receptor such as a G-protein-linked receptor, rate of secretion of a substance from a cell, enzymatic activity, genetic expression, and so on.

An "antagonist" is a compound that reduces or inhibits a biochemical or physiological activity. For a compound to be an antagonist, it is not necessary that there exist any known agonist, and it is not necessary that the antagonist work by reducing the activity of a corresponding agonist.

The cannabinoid receptors include $CB_1$ and $CB_2$. $CB_1$ and $CB_2$ are members of the G protein-coupled receptor family. The ligands of $CB_1$ include $\delta^9$-tetrahydrocannabinol ($\delta^9$-THC), as well as an endogenous ligand, N-arachidonyl ethanolamide (AEA; anandamide). In addition to $CB_1$ and $CB_2$, cannabinoids can bind to "receptors" such as various ion channels, such as vanilloid (TRPV) receptors, and to nuclear receptors, such as peroxisome proliferator-activated receptor (PPAR) (Console-Bram et al (2012) Prog. Neuropsychopharmacol. Biol. Psychiatry. 38:4-15). Biochemical properties of terpenes, including receptor binding, can be assessed using labeled terpenes and labeled ligands where a terpene influences binding properties of the labeled ligand. Useful labels include $^{32}P$, $^{33}P$, $^{35}S$, $^{14}C$, $^{3}H$, $^{125}I$, stable isotopes, epitope tags, fluorescent dyes, electron-dense reagents, substrates, or enzymes, e.g., as used in enzyme-linked immunoassays, or fluorettes (see, e.g., Rozinov and Nolan (1998) Chem. Biol. 5:713-728). Terpenes in *cannabis* have been described (see, e.g., Flores-Sanchez and Verpoorte (2008) Secondary metabolism in *cannabis* in Phytochem. Rev. DOI 10.1007/s11101-008-9094-4).

This concerns the terms, composition and formulation. In some embodiments, without implying any limitation, a composition is a solution, suspension, emulsion, slurry, gel, and so on, where the formulation is mixed within or dispersed within the composition. In this type of embodiment, the formulation can be evenly distributed throughout the composition. In other embodiments, the composition and formulation can be substantially different things, for example, the composition can be a matrix of fibers, where the formulation surrounds or coats the fibers. Also, the composition can be compartment that contains a fragrance that is not a terpene, while the formulation consists only of terpenes and that resides in a separate compartment. In some embodiments, the composition includes non-terpenes that float above the terpene formulation or, alternatively, that sink below the terpene formulation. In other embodiments, the non-terpene constituents of the composition can reside in beads or granules, while the terpene formulation can take the form of a solution. Alternatively, the terpene formulation can reside in beads or granules, while the non-terpene components of the terpene formulation can be configured as something that is not beads or granules.

"Synergy" refers to the phenomenon where a first compound stimulates a first level of a particular activity, where a second compound stimulates a second level of the same particular activity, and where the presence of both compounds results in a third level of the same particular activity, where the third level is greater than the additive sum of the first level and the second level. Synergy can occur where the first compound and second compound are used at the same time, or where the first compound and second compound are used sequentially.

"Entourage compound" is a compound that can increase the effects of one or more naturally-occurring ligands that bind to one or more receptors, but that has little or no affinity for the receptor. In a preferred, but non-limiting embodiment, an entourage compound increases the effects of a naturally-occurring ligand that binds to one or more cannabinoid receptors, but that has little or no affinity for the cannabinoid receptor.

Suppliers of terpenes that are pure and homogeneous, contract laboratories that synthesize terpenes, and contract laboratories that purify terpenes from natural products, e.g., essential oils, are available (see, e.g., Sigma-Aldrich, St. Louis, Mo.; TCI America, Portland, Oreg.; Arizona Chemical, Jacksonville, Fla.). Without implying any limitation, the term "pure" can refer to a terpene that is over 95% pure, over 98% pure, over 99% pure, over 99.5% pure, over 99.9% pure, over 99.99% pure, and the like. Generally, the term "pure" does not take into account any solvent that may be used for dissolving the terpene, such as a solvent that is ethanol, acetone, tetrahydrofuran, and so on. In other words, unless specified otherwise, either explicitly or by the context, any solvent that is present is not relevant to the characterization of a given terpene as pure and homogeneous.

Biochemical Assays for Entourage Compounds

The ability of a compound, such as a terpene, to serve as an agonist, an antagonist, to synergize with another compound, or to function as an entourage compound, can be assessed by a number of assay methods. Methods for determining binding to cells or subcellular particles that express a cannabinoid receptor have been described (Leggett et al (2004) Br. J. Pharmacol. 141:253-262). Leggett et al, supra, determined that a fatty acid amide (oleamide) can activate cannabinoid receptor CB1.

Human Sensory Panel for Odors; Correlating Odors with Chemical Quantitation of Odiferous Compounds At least the following methods are available for use in the present disclosure. Human panels have been trained to evaluate odors, such where the odors had the names, grassy green, green spicy, sweet, seasoned, sharp, soupy, mellow, metallic, fragrant fruity, cardboard-like, and complex (Kurobayashi et al (2006) Biosci. Biotechnol. Biochem. 70:958-965). The Kurobayashi et al, supra, study included detection of odor of terpenes, e.g., myrcene. Human panels have been trained to evaluate the level of odorants, including terpenes (linalool; L-carvone) on a scale of zero (extremely mild) to ten (extremely intense). Odorants were delivered to human subjects using an air stream. The subjects receiving the odorants, and providing subjective responses on odor intensity, also provided objective responses using electroolfactograms (EOG). The EOG test involved placing electrodes on the contralateral bridge of the nose, earlobe, and mastoids.

A variety of physiological parameters have been tested, in studies of subject response to terpenes, e.g., linalolol. These parameters include blood oxygen saturation, pulse rate, breathing rate, eye-blinks, skin conductance, skin temperature, and surface electromyogram (Neuberger et al (2004) Neuropsychopharmacology. 29:1925-1932). Various subjective parameters have also been tested, in subject response to terpenes, including subjective attentiveness, mood, cheerfulness, subjective relaxation, vigor, calmness, alertness (see, e.g., Neuberger et al (2004) Neuropsychopharmacology. 29:1925-1932; Diego et al (1998) Int. J. Neurosci. 96:217-224; Knasko (1992) Chem. Senses. 17:27-35). Sugawara's group (Sugawara et al (1998) J. Home Econ. Jpn. 49:1281-1290; Sugawara et al (2013) Molecules. 18:3312-3338; Satoh and Sugawara (2003) Analytical Sciences. 19:139-146), have used sensory tests for assessing subjective responses to a variety of terpene-containing oils. The terpene-containing oils were tested for subjective impressions, that is, fresh-stale, soothing-activating, airy-heavy, plain-rich, natural-unnatural, elegant-unrefined, soft-strong, pleasant-unpleasant, warm-cool, comfortable-uncomfortable, woodsy-not woodsy, floral-peppery, lively-dull. Sugawara's group also provided methods for the statistical analysis of data on subjective response, for example, calculation of the p value. These investigators also acquired electroencephalography data. Odorant was administered by a 300 mL inhaler flask, where 0.02 to 0.2 mL of odorant was applied to a strip of filter paper placed at the bottom of the flask.

Moss et al (2008) Intern. J. Neuroscience. 118:59-77, discloses tests for assessing various psychological responses to aromas such as peppermint odor. The tests include those for alertness, calmness, contentedness, immediate word recall, ability to match digits quickly, memory of details of a picture of a 3-dimensional house, and time to respond by pressing yes or no in order to match a screen that displays either "yes" or "no."

Fragrance Panels with Human Subjects

Odorants, volatile chemicals, and fragrances, can be administered by various devices, e.g., Aroma-Stream (Tisserand, Hove, Sussex, England), H2EO Aircare Ultrasonic Diffuser (Aromatics International, Lolo, Mont.), ZAQ NoorAir Aromatherapy Essential Oil Diffuser (Enovize, Inc., Skokie, Ill.).

Detecting the presence of odiferous chemicals, as well as the quantification of one or more odiferous chemicals, can be assessed by the human nose. Quantification can be in terms of, for example, micrograms/liter of air, nanograms/L of air, picograms/L of air, femtograms/L of air, attograms/L of air, and so on. Also, quantification can be in terms of micromoles/liter of air, nanomoles/L of air, picomoles/L of air, femtomoles/L of air, attomoles/L of air, and so on. The skilled artisan is able to quantify the concentrations of various volatile compounds, by way of odor. For example, 2,4,6-trichloroanisole (TCA) can be detected by way of smell, when it exists at a concentration of a few nanograms/L of air (H. Rudy. Gerstel Solutions Worldwide, No. 11, pages 9-11). To give another example, the lower limit of detection of formaldehyde in the air has been determined to be 0.03-1.0 milligrams formaldehyde per cubic meter of air (Salthammer et al (2010) Chem. Rev. 110:2536-2572).

Sensory panels with human subjects are used to identify odors, including odors of degradation products of polypropylene and polyethylene. These degradation products can include aldehydes, ketones, carboxylic acids, alcohols, and lactones. Studies have demonstrated the correlation of human odor perceptions with chemical quantitation by mass spectroscopy and gas chromatography (Hopfer et al (2012) Anal. Bioanal. Chem. 402:903-913). Human sensory panels have been used for detecting and quantifying a variety of organic chemicals (see, e.g., Johnson et al (2012) PLoS ONE. 7:e32693 (7 pages); Zhou et al (1999) J. Agric. Food Chem. 47:3941-3953; Brattoli et al (2011) Sensors (Basel). 11:5290-5322).

Synthetic Nasal Devices

Synthetic nasal devices, including electronic nose devices are available. See for example, Cyranose® 320, Sensigent, Baldwin Park, Calif.; Arshak et al (2004) Sensor Review. 24:181-198; Monge et al (2004) Comb. Chem. High Throughput Screen. 7:337-344; Ye et al (2011) J. Pharm. Biomed. 55:1239-1244; Hodgins et al (1995) J. Automat. Chem. 17:179-185.

Classification of a Chemical or Oil by Fragrance Notes

The present disclosure encompasses terpene formulations that can be characterized by one or more of the following sensory terms, that is, citrus, citrus peel, lemon, lemon rind, lime, grapefruit, grapefruit peel, fruity, creamy, nut-like, melon, berry, seedy, strawberry, cranberry, pineapple, floral, earthy, wood, pine, woody/pine, herbal, tea-like, musty and cheesy aromas, raspberry, orange, acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, musk, sweet, balsamic, spicy, woody, heavy floral, cheesy, mandarin, ugli fruit; anise, cinnamon clove, basil, mint, lavender, lavandin, thyme, rosemary, geranium, roses, citronella, cypress, eucalyptus, Peru balsam, camphor, sandalwood, ylang, cedarwood, Amyris oil, cedarwood oil, cocoa absolute, copaiba balsam, menthe oil pays, myrrh resin, patchouli oil, vanillin, vetiver oil. See, US 2010/0111880 of Chen, U.S. Pat. No. 7,534,460 of Dewis, US 2009/0257973 of Fraser, which are each incorporated herein by reference in their entirety. The disclosure also encompasses compositions with a fragrance that has, e.g., bewitching, warm, powdery, slightly animal and velvety connotation (see, RE38,659 of Williams, which is incorporated by reference). Also encompassed are compositions with a fragrance that has, e.g., a green note, floral note, fruity note, chypre note, oriental note, leather note, tobacco note.

The present disclosure provides a formulation that contains a top note terpene, middle note terpene, and bottom note terpene. U.S. Pat. No. 6,769,428 of Cronk identifies terpenes that are top note (e.g., citronellal, citronellol, citronellyl acetate, dihydrolinalool, dihydromyrcenol, eucalyptol, geraniol, geraniol, geranyl acetate, geranyl nitrile, hydroxycitronellal, d-limonene, linalool, linaool oxide, linalyl acetate, linalyl propionate, methyl anthranilate, alpha-methyl ionone, methyl nonyl acetaldehyde, menthone, iso-menthone, myrcene, myrcenyl acetate, myrocenol, nerol, neryl acetate, alpha-pinene, beta-pinene, gamma-terpinene, alpha-terpineol, beta-terpineol, terpinyl acetate), middle note (e.g., coumarin, ethyl vanillin, eugenol, iso-eugenol), and bottom note (e.g., hexyl cinamic aldehyde).

The present disclosure provides terpene compositions that contain individual terpenes with a high volatility and low substantivity. Chemicals with a high volatility and low substantivity are used to give an initial burst of characters, such as light, fresh, fruity, citrus, green or floral, which are detected soon after application. Such materials are referred to, by the artisan skilled in the field of fragrances as "top notes". Less volatile, and more substantive, chemicals, at least in perfumes, are used to give characters such as musk, sweet, balsamic, spicy, woody or heavy floral to the fragrance oil which, although may also be detected soon after application, also last for longer. The skilled artisan refers to these materials as "middle notes" or "base notes". The skilled artisan can blend perfume raw materials so that the resultant fragrance oils have the desired overall fragrance character profile (see U.S. Pat. No. 7,208,464 of Heltovics, which is incorporated herein by reference in its entirety). "Top note" fragrances are "fragrances having a high vapor pressure, and when applied to a paper sachet, vaporization takes place within 2 hours, and no scent remains. "Middle note" fragrances are "fragrances having a medium vapor pressure, and when applied to a paper sachet, the scent remains from about 2 to about 6 hours. "Base note" fragrances are fragrances having a low vapor pressure and high retentivity, and when applied to a paper sachet, the scent remains for more than about 6 hours. The terms "top note", "middle note", and "base note" are recognized by those skilled in the art of fragrance-containing compositions. See, U.S. Pat. No. 6,013,618 of Morelli, which is incorporated herein by reference in its entirety.

The present disclosure provides a formulation that comprises at least one terpene that provides a top note aroma, at least one terpene that provides a middle note aroma, and at least one terpene that provides a bottom note aroma. Also provided is a formulation that contains one or more terpenes that provides only a top note aroma. Also provided is a formulation that contains one or more terpenes that provides only a middle note aroma. Also provided is a formulation that contains one or more terpenes that provides only a bottom note aroma. Also provided is a formulation that contains only terpenes that provide a top note aroma and a bottom note aroma. Also provided is a formulation that contains only terpenes that provide a top note aroma and a middle note aroma. Also provided is a formulation that contains only terpenes that provide a middle note aroma and a bottom note aroma.

Modifiers

The present disclosure provides a composition that comprises a terpene formulation and one or more modifiers. As used herein, the term "modifier" refers to other classes of chemicals that are not terpenes. Chemicals such as thiols, esters, ketones, and aldehydes are potential modifiers. These compounds have distinct fragrances. The present invention contemplates using such other chemicals in conjunction with terpenes.

Thiols are organosulfur compounds that contain a carbon-bonded sulfhydryl group. They have pungent odors often resembling garlic.

Esters are organic compounds that occur naturally in fats and oils. They often have a pleasant fruity odor. They are responsible for the aromas of many fruits, including apples, bananas, and strawberries.

Some modifier compounds that are contemplated by the invention are 3-methyl-2-butene-1-thiol (sulfur compound) and hexanoic acid hexyl ester (pungent odor). Another modifier compound for use with the present invention is 2-heptanone, which is a naturally occurring compound in beer, bread, and some cheeses, and which has a banana-like odor.

Octanal and cis-4-decenal are aldehydes that have a fruit-like citrus odor. Either or both compounds can be used as modifiers within the compositions of the disclosed invention.

Cannabinoids are another class of modifiers contemplated by the invention. Cannabinoids are a class of diverse chemical compounds that act on cannabinoid receptors in the brain. Many are produced naturally in the human body. Others known as phytocannabinoids are found in and on plants. Some commonly known phytocannabinoids include tetrahydrocannabinol (THC) and cannabidiol (CBD). Cannabinoids can also be created synthetically.

The addition of cannabinoids of 60-99% purity to a composition of terpenes and propylene glycol emulsifies the terpenes in the mixture. Cannabinoids added at 10-70% act as an emulsifier.

Without implying any limitation, other modifiers can be selected from 4-hydroxy-2,5-dimethyl-3(2H)-furanone (strawberry), ethyl butyrate (apple, fruity), isoamyl acetate (banana), propyl hexanoate (pineapple, fruity), allyl hexanoate (pineapple, fruity), valencene (orange, fresh fruity), methyl anthranilate (also known as methyl 2-aminobenzoate) (grape), methyl butyrate (fruity, apple, pineapple), benzyl acetate (fruity, strawberry), p-mentha-8-thiol-3-one (grapefruit), (1S,4S)-trans-p-menthan-8-thiol-3-one acetate (black currant, exotic), (1R,4S)-cis-p-menthan-8-thiol-3-one acetate (fruity, sweet).

Without implying any limitation, a composition that comprises a formulation of terpenes and one or more modifiers, can consist of about 99.5% terpenes and about 0.5% modifiers, about 99% terpenes and about 1% modifiers, about 95% terpenes and about 5% modifiers, about 90% terpenes and about 10% modifiers, about 85% terpenes and about 15% modifiers, about 80% terpenes and about 20% modifiers, about 75% terpenes and about 25% modifiers, about 70% terpenes and about 30% modifiers, about 60% terpenes and about 40% modifiers, about 50% terpenes and about 50% modifiers, about 40% terpenes and about 60% modifiers, about 30% terpenes and about 70% modifiers, about 20% terpenes and about 80% modifiers, and so on, as expressed in weight/volume (wt./vol.).

Isolation and Analysis of Terpenes

Terpenes can be purified, analyzed, and identified, by various techniques, including high pressure liquid chromatography (HPLC), gas chromatography, and other chromatographic techniques (see, e.g., Musenga et al (2006) J. Sep. Sci. 29:1251-1258; Yang et al (2009) J. Nat. Prod. 72:484-487; Jella et al (1998) J. Agric. Food Chem. 46:242-247; Andrea et al (2003) J. Agric. Food Chem. 51:4978-4983; Villa et al (2007) J. Pharm. Biomed. Anal. 44:755-762).

Terpenes and other chemicals can be analyzed by mass spectrometry (Hendriks and Bruins (1983) Biol. Mass Spectrom. 10:377-381; gas chromatography-mass spectrometry (GC-MS) (Gadulo et al (2010) J. Food Sci. 75:C199-207), nuclear magnetic resonance (NMR) (Mucci et al (2013) Food Chem. 141:3167-3176; Zhang et al (2013) Food Chem. 138:208-213), mass spectroscopy, and Matrix-Assisted Laser Desorption/Ionization Time-of-Flight mass spectrometry (MALDI-TOF) (Scalarone et al (2005) J. Mass Spectrom. 40:1527-1535).

Creation of a Database of Terpenes

The present invention involves the isolation and analysis of naturally-occurring terpene compositions, and also the preparation of terpene compositions that mimic those compositions found in nature.

Methods of the inventions involve generating a library of prepared terpene compositions, the process comprising: obtaining a sample; analyzing a chemical profile of the sample to identify terpenes in the sample; quantifying the terpenes identified; and generating a library or database of terpene compositions based on those quantities. The method may further comprise preparing a blend of terpenes that mimics one or more of the compositions represented in the library.

The sample can be from any plant or other natural product, including *Cannabis sativa*, *Humulus lupulus*, or other plant strains. The analysis step may comprise separating substances from a mixture, genetic analysis, chemotaxonomic analysis, compound extraction, gas chromatography flame ionization detection, chemical formula identification, chromatography, or any other analytical chemistry technique described herein or otherwise known in the art. Terpenes can be identified based on their chromatography profiles or other chemical properties of the analyzed compounds. Terpenes identified can be those listed in Tables 1-37 below, or any other terpene. Terpenes may be quantified based on their mass fraction, percent weight, mole fraction, percentage by volume, or the like. The compositions and their quantities can be assembled as a library or database, or any other data management format known in the art. In embodiments that involve creating a prepared blend that mimics a naturally-occurring composition, the synthetic blend may comprise all naturally-occurring terpenes, all synthetic terpenes, or a combination thereof.

Also provided is a database or library of terpene compositions produced by the above process.

Fluids

In "comprising" embodiments, the present disclosure provides a formulation that comprises a fluid that is a transparent liquid, a translucent liquid, an opaque liquid, a slurry, an emulsion, a suspension, a gel, and the like. In "consisting" embodiments, the present disclosure provides a formulation that consists of a fluid that is a transparent liquid, a translucent liquid, an opaque liquid, a slurry, an emulsion, a suspension, a gel, and the like. The designation of liquid, slurry, emulsion, gel, and so on, refers to this characterization as determined at room temperature (about 23 degrees centigrade).

Solvents are encompassed, such triacetin, dipropylene glycol, diethyl phthalate, isoparaffins, paraffins, silicon oils, perfluorinated aliphatic ethers, glycol ethers, glycol ether esters, esters, or ketones, propylene glycol, ethanol, triacetin, dimethicone or cyclomethicone, and so on.

Solvents such as propylene glycol are commonly used in electronic cigarette (e-cigarette) formulations. As discussed above, the addition of 10-70% cannabinoids to a mixture of terpenes and propylene glycol creates an emulsified mixture ideal for use in e-cigarettes.

EXCLUSIONARY EMBODIMENTS

In embodiments, the present disclosure can exclude a composition that has any essential oil. Also, the disclosure can exclude a composition that contains one or more specific oils, such as ocimum oil, jasmine oil, cymbopogon oil (lemongrass), santalum oil, eucalyptus oil, bergamote oil, lemon oil, lavandin oil, spearmint oil, wintergreen oil, cardamom oil, neroli bigarade oil, rosemary oil, orange oil, petitgrain oil, cinnamon leaf oil, vetiver oil, patchouli oil, grapefruit oil, mandarine oil, mandarin oil, pepper oil, valerian oil, almond oil, citronella oil, anise oil, geranium oil, mint oil, verbena oil, clove oil, cajeput oil, fennel oil, girfole oil, myrtle oil, thyme oil, cypress oil, pine oil, armoise oil, and so on. What can be excluded is a composition that contains any kind of citrus fruit oil, e.g., from orange, lemon, grapefruit, and so on. Where applicable, the present disclosure encompasses an oil that is an "essential oil." Also, the present disclosure can encompass any formulation that includes one or more of the above oils.

In an exclusionary embodiment, the invention provides any of the above compositions, wherein the composition does not contain 3,3'-dihydroxy-5,4'-dimethoxybibenzyl. In another exclusionary embodiment, the invention provides any of the above compositions, wherein the composition does not contain cellulose. In another exclusionary embodiment, the invention provides any of the above compositions, wherein the composition does not contain chlorophyll.

Also, what can be excluded is any composition that contains a terpene that accounts for at least 20%, at least 30%, at least 40%, at least 50%, at least 60%, at least 70%, at least 80%, or at least 90%, of the terpenes in any one of the oils (or essential oils) disclosed herein. Moreover, what can be excluded is any composition that comprises one of the terpene trios that are identified in the tables herein. Each terpene trio is a group of three different terpenes that are explicitly identified by the three numbers in the trio (Table 1 is a key for each number).

Without implying any limitation, what can also be excluded from the present disclosure is any composition that includes one or more excipients, viscosity-imparting agents, solvents, binders, lubricants, preservatives, anti-oxidants, and the like. For example, what can be excluded from the present disclosure is, paraffin oil, isopropyl palmitate, cetryl alcohol, beeswax, polyethylene glycol, glycerol, pheoxyethanol, silica, sodium bicarbonate, sodium carbonate, cellulose, carboxymethyl cellulose, acacia agar, gums, hydrogels, alginic acid, a monosaccharide, a disaccharide, and so on. In embodiments, the present disclosure can include one or more excipients, viscosity-imparting agents, solvents, binders, lubricants, preservatives, and the like, such as one or more of those disclosed herein.

In other exclusionary embodiments, what can be excluded is a composition, where a fluid component of the composition, does not contain one or more of the following molecules (see, e.g., Flores-Sanchez and Verpoorte (2008) Secondary metabolism in *cannabis* in Phytochem. Rev. DOI 10.1007/s11101-008-9094-4): cannabigerol; cannabichromene; cannabitriol; cannabidiol; cannabicyclolol; cannabielsoin, cannabinodiol; cannabinol; delta8-tetrahydrocannabinol; delta9-tetrahydrocannabinol; cannabichromanone; cannabicoumaronone; cannabicitran; 10-oxo-delta6a10a-tetrahydrocannabinol; cannabiglendol; delta7-isotetrahydrocannabinol; CBLVA; CBV; CBEVA-B; CBCVA; delta9-THCVA; CBDVA; CBGVA; divarinolic acid; quercetin; kaemferol; dihydrokaempferol; dihydroquercetin; cannflavin B; isovitexin; apigenin; naringenin; eriodictyol; luteolin; orientin; cytisoside; vitexin; canniprene; 3,4'-dihydroxy-5-methoxybibenzyl; dihydroresveratrol; 3,4'dihydroxy-5,3'-dimethoxy-5'-isoprenyl; cannabistilbene 1; cannabistilbene 11a; cannabistilbene 11b; cannithrene 1; cannithrene 2; cannabispirone; iso-cannabispirone; cannabispirenon-A; cannabispirenone-B; cannabispiradienone; alpha-cannabispiranol; beta-cannabispiranol; acetyl-cannabispirol; 7-hydroxy-5-methoxyindan-1-spiro-cyclohexane; 5-hydroxy-7-methoxyindan-1-spiro cyclohexane; 5,7-dihydroxyindan-1-cyclohexane; cannabispiradienone; 3,4'-dihydroxy-5-methoxybibenzyl; canniprene; cannabispirone; cannithrene I; cannithrene 2; alpha-cannabispiranol; acetyl-cannabispirol; vomifoliol; dihydrovomifoliol; beta-ionone; dihydroactinidiolide; palustrine; palustridine; plus-cannabisativine; anhydrocannabisativine; dihydroperiphylline; cannabisin-A; cannabisin-B; cannabisin-C; cannabisin-D; grossamide; cannabisin-E; cannabisin-F; cannabisin-G; and so on.

The present disclosure provides a terpene formulation that comprises only one monoterpene. The present disclosure provides a terpene formulation that comprises only two monoterpenes. The present disclosure provides a terpene formulation that comprises only three monoterpenes. The present disclosure provides a terpene formulation that comprises only four monoterpenes.

The present disclosure provides a terpene formulation that comprises only one sesquiterpene. The present disclosure provides a terpene formulation that comprises only two sesquiterpenes. The present disclosure provides a terpene formulation that comprises only three sesquiterpenes. The present disclosure provides a terpene formulation that comprises only four sesquiterpenes.

In exclusionary embodiments, the present disclosure can exclude any composition, and can exclude any formulation that includes an essential oil. Also, the present disclosure can exclude any composition, and can exclude any formulation that includes one or more of salicyladlehyde, glycerol, polyethylene glycol, ionic detergent, non-ionic detergent, surfactant, phenylgycidate compound, calone, vanillin, jamunate, manzanate, verdox, vertoliff, furaneol, methyl cinnamate, butyl valerate, amyl acetate, furfural, ethyl vanillin, a lactone compound, any kind of aldehyde, methyl ionone, citrate, fumarate, amyl cinnamal, benzyl alcohol, free ions or salts of carbonate, free ions or salts of sulfate, free ions or salts of phosphate, cymene, any salicylate compound, anisyl alcohol, methyl heptin carbonate, any compound with a ketone group, any compound with a benzoate group, any sugar, dextrose, dextrate, silica, maltodextrin, sorbitol, and oil that is other than an essential oil, and the like. Other compounds, which can be excluded from the compositions and formulations of the present disclosure, or in the alternative, which can be included, are disclosed (see, e.g., US 2008/0194455 of Widder, U.S. Pat. No. 5,948,812 of Kraft, US 2003/0024997 of Welch, US 2009/0004303 of Perring each of which is incorporated herein by reference in its entirety).

The present disclosure provides a terpene formulation that comprises only one monoterpene. The present disclosure provides a terpene formulation that comprises only two monoterpenes. The present disclosure provides a terpene formulation that comprises only three monoterpenes. The present disclosure provides a terpene formulation that comprises only four monoterpenes.

The present disclosure provides a terpene formulation that comprises only one sesquiterpene. The present disclosure provides a terpene formulation that comprises only two sesquiterpenes. The present disclosure provides a terpene formulation that comprises only three sesquiterpenes. The present disclosure provides a terpene formulation that comprises only four sesquiterpenes.

In exclusionary embodiments, the present disclosure can exclude any composition, and can exclude any formulation that includes an essential oil. Also, the present disclosure can exclude any composition, and can exclude any formulation, that includes water, over 0.1% water (wt./vol.), over 0.2% water, over 0.5% water, over 1.0% water, over 2% water, over 5% water, and so on. Moreover, the present disclosure can exclude any composition, and can exclude any formulation, that includes one or more of salicyladlehyde, glycerol, polyethylene glycol, ionic detergent, non-ionic detergent, surfactant, phenylgycidate compound, calone, vanillin, jamunate, manzanate, verdox, vertoliff, furaneol, methyl cinnamate, butyl valerate, amyl acetate, furfural, ethyl vanillin, a lactone compound, any kind of aldehyde, methyl ionone, citrate, fumarate, amyl cinnamal, benzyl alcohol, free ions or salts of carbonate, free ions or salts of sulfate, free ions or salts of phosphate, cymene, any salicylate compound, anisyl alcohol, methyl heptin carbonate, any compound with a ketone group, any compound with a benzoate group, any sugar, dextrose, dextrate, silica, maltodextrin, sorbitol, and oil that is other than an essential oil, and the like. Other compounds, which can be excluded from the compositions and formulations of the present disclosure, or in the alternative, which can be included, are disclosed (see, e.g., US 2008/0194455 of Widder, U.S. Pat. No. 5,948,812 of Kraft, US 2003/0024997 of Welch, US 2009/0004303 of Perring, US 2009/0162308 of Kuhn, each of which is incorporated herein by reference in its entirety).

The present disclosure provides formulations that include one or more of these terpenes. In exclusionary embodiments, the present disclosure can also exclude one or more of any terpene that is disclosed herein.

Example 1

In a first example, a composition was provided comprising equal parts myrcene, limonene, linalool, alpha-pinene, and beta-caryophyllene. This particular composition of terpenes was designed to have a citrus scent. Three human subjects tested the organoleptic properties of the composition and reported the odor qualities of the composition. The first human subject reported a "sweet citrus" scent, with "woody earthen overtones." The second human subject described the composition as having a "light floral" aroma with a hint of "fruity citrus." The third human subject reported a "pleasant flowery scent" with notes of "lemony citrus."

Example 2

To create a database of terpene compositions like the database or library described herein, naturally occurring plant samples were analyzed for their chemical properties. FIG. 1 shows a method 100 for generating such a database. The method 100 involves obtaining a sample in step 110. The sample can be a naturally occurring plant product, such as a member of the *Cannabis* genus, or any other plant product. Step 120 of the method involves analyzing a chemical profile of the sample to identify terpenes therein. The analysis can be any of the chemical analyses described herein, including chromatography. The analysis step may further comprise other processes for extracting compounds or otherwise preparing the sample for analysis. The method further comprises quantifying terpenes in step 130. The terpenes can be quantified by mass fraction, percent weight, mole fraction, percentage by volume, or the like. The quantities can be used to determine a ratio of terpenes in the composition. In step 140, those quantities, ratios, or other chemical properties are entered into a database of terpene compositions. The database may comprise chromatography profiles or other chemical properties found in the terpene compositions.

Figure 2:
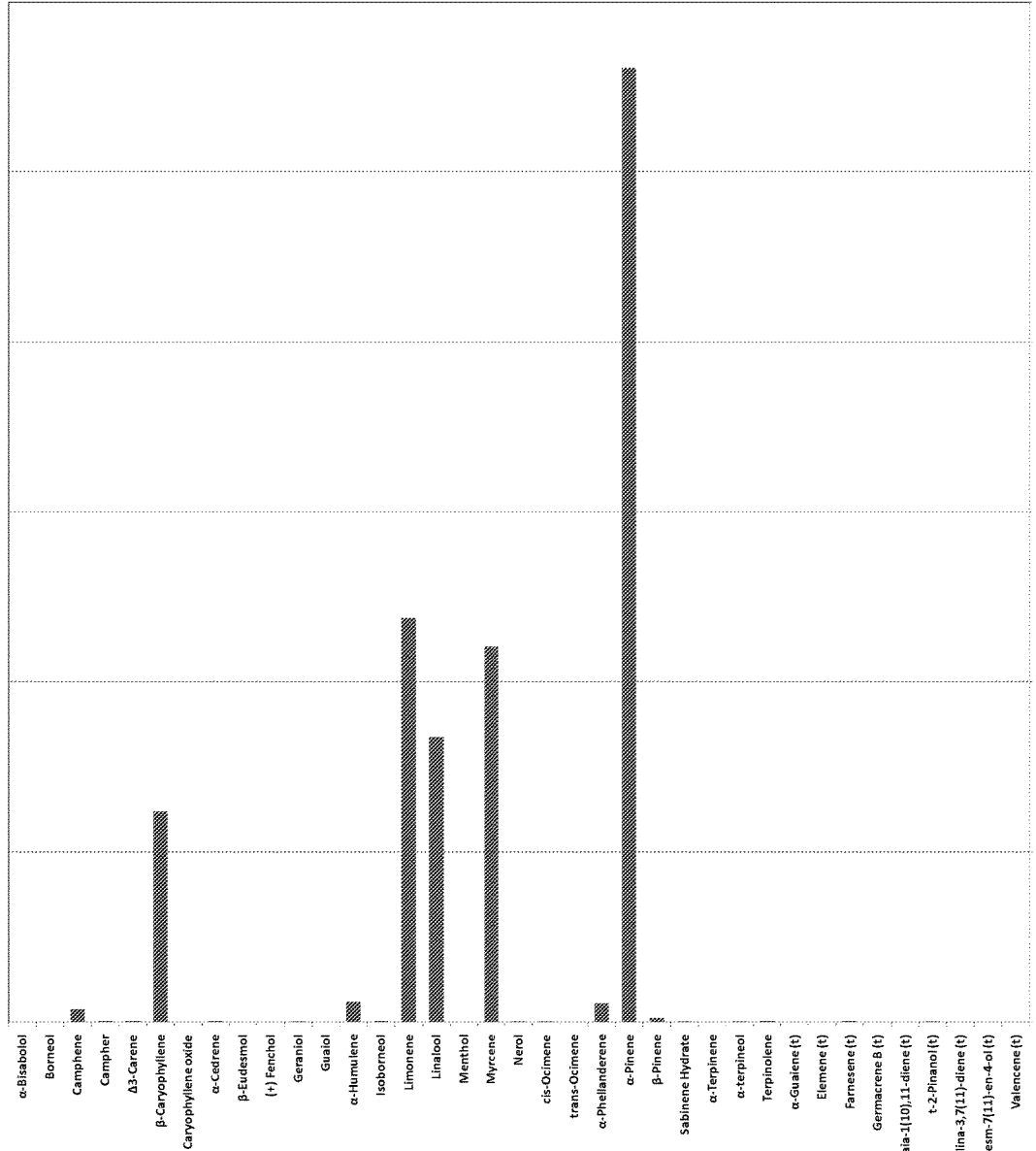
FIG. 2 shows the result of a chromatographic analysis of a typical blend or strain of plant by terpene content, according to the present inventions.

An example of one such analysis is shown in FIG. 2. A sample of a naturally occurring plant was isolated and analyzed using chromatography. The five most abundant terpenes in the composition were found to be beta-caryophyllene, limonene, linalool, myrcene, and alpha-pinene. These terpenes were determined to be present in quantities of 1.85 mg/g, 3.56 mg/g, 2.50 mg/g, 3.31 mg/g, and 8.40 mg/g, respectively. Other terpenese were found in trace quantities, including camphene, alpha-humulene, alpha-phellandrene, and beta-pinene. These quantities and chemical properties were entered into a database, like the one described herein.

Other Examples

Compositions of the present disclosure encompass, but are not limited to, combinations of terpenes from Tables 1-37.

TABLE 1

| Terpenes | |
|---|---|
| Table 1. Terpenes | |
| 1 | Alpha-bisabolol |
| 2 | Borneol |
| 3 | Camphene |
| 4 | Camphor |
| 5 | Delta-3-carene |
| 6 | Beta-caryophyllene |
| 7 | Caryophyllene oxide |
| 8 | Alpha-cedrene |
| 9 | Beta-eudesmol |
| 10 | (+)Fenchol |
| 11 | Geraniol |
| 12 | Guaiol |
| 13 | Alpha-humulene |
| 14 | Isoborneol |
| 15 | Limonene |
| 16 | Linalool |
| 17 | Menthol |
| 18 | Myrcene |
| 19 | Nerol |
| 20 | Cis-ocimene |
| 21 | Trans-ocimene |
| 22 | Alpha-phellandrene |
| 23 | Alpha-pinene |
| 24 | Beta-pinene |
| 25 | Sabinene |
| 26 | Alpha-terpinene |
| 27 | Alpha-terpineol |
| 28 | Terpinolene |
| 29 | Alpha-guaiene |
| 30 | Elemene |
| 31 | Farnesene |
| 32 | Germacrene B |
| 33 | Guaia-1(10),11-diene |
| 34 | Trans-2-pinanol |
| 35 | Selina-3,7(11)-diene |
| 36 | Eudesm-7(11)-en-4-ol |
| 37 | Valencene |

Terpene Combinations

The present disclosure provides terpene formulations that comprise the following combinations. Also, the present disclosure provides terpene formulations that include the following combinations of terpenes but that do not have any additional terpenes. Without implying any limitation, what is encompassed are the following combinations from Table 1:

Combination of alpha-bisabolol and borneol. This is the combination of terpene 1 and terpene 2 from Table 1. Also encompassed are terpene formulations that comprise, or alternatively, that consist if, the combinations shown in Table 2. Thirty-seven terpene families are listed. Each family includes the named terpene, plus additional terpenes as listed in adjacent columns in the table. The present disclosure provides formulations that comprise the listed mixtures of terpenes, but which may include additional terpenes. The present disclosure also provides formulations that comprise the listed mixtures of terpenes, but which may not include any additional terpenes. The terpene identified as "base terpene" refers to the terpene present in greatest abundance (weight/volume). Where two terpenes occur in roughly the same abundance (weight/volume), either of these two terpenes can be designated as the "base terpene."

Where a formulation includes the indicated mixture of three terpenes and additional terpenes, in various embodiments, what is included is only one additional terpene, or only two additional terpenes, or only three additional terpenes, or only 4, or only 5, or only 6, or only 7, or only 8, or only 9, or only 10, or only 11, or only 12, or only 13, or only 14, or only 15, or only 16, or only 17, or only 18, or only 19, or only 20 additional terpenes, or only 2-5 additional terpenes, or only 5-8 additional terpenes, or only 8-11 additional terpenes, or only 11-14 additional terpenes, or only 14-17 additional terpenes, or only 17-20 additional terpenes, and so on.

Where a formulation includes the indicated mixture of three terpenes and additional terpenes, in one embodiment, what is included is additional terpenes, where the three terpenes (trio) account for about 5% of the terpenes (wt./vol.), and where the remaining about 95% of the formulation can take the form of one or more other terpenes.

Where a formulation includes the indicated mixture of three terpenes and additional terpenes, in one embodiment, what is included is additional terpenes, where the three terpenes (trio) account for about 10% of the terpenes (wt./vol.), and where the remaining about 90% of the formulation can take the form of one or more other terpenes.

Where a formulation includes the indicated mixture of three terpenes and additional terpenes, in one embodiment, what is included is additional terpenes, where the three terpenes (trio) account for about 20% of the terpenes (wt./vol.), and where the remaining about 80% of the formulation can take the form of one or more other terpenes.

Where a formulation includes the indicated mixture of three terpenes and additional terpenes, in one embodiment, what is included is additional terpenes, where the three terpenes (trio) account for about 30% of the terpenes (wt./vol.), and where the remaining about 70% of the formulation can take the form of one or more other terpenes.

Where a formulation includes the indicated mixture of three terpenes and additional terpenes, in one embodiment, what is included is additional terpenes, where the three terpenes (trio) account for about 50% of the terpenes (wt./vol.), and where the remaining about 50% of the formulation can take the form of one or more other terpenes.

Where a formulation includes the indicated mixture of three terpenes and additional terpenes, in one embodiment, what is included is additional terpenes, where the three terpenes (trio) account for about 70% of the terpenes (wt./vol.), and where the remaining about 30% of the formulation can take the form of one or more other terpenes.

Where a formulation includes the indicated mixture of three terpenes and additional terpenes, in one embodiment, what is included is additional terpenes, where the three terpenes (trio) account for about 90% of the terpenes (wt./vol.), and where the remaining about 10% of the formulation can take the form of one or more other terpenes.

Where a formulation includes the indicated mixture of three terpenes and additional terpenes, in one embodiment, what is included is additional terpenes, where the three terpenes (trio) account for about 95% of the terpenes (wt./vol.), and where the remaining about 5% of the formulation can take the form of one or more other terpenes.

The present disclosure provides exclusionary embodiments, where what can be excluded is any formulation that contains one of the terpene trios, as disclosed in any one of the following tables. To provide an example, what is encompassed by the present disclosure is an exclusionary embodiment that excludes any composition or formulation that contains all three of the terpenes: 1, 2, and 3. To provide another example, what is encompassed is an exclusionary embodiment that excludes any composition or formulation that contains all three of the terpenes: 8, 11, and 12. Table 1 is the key that identifies the terpene associated with the number.

TABLE 2

Alpha-bisabolol family of terpene formulations.
Table 2. Alpha-bisabolol family of terpene formulations.
The numbers refer to the terpenes from Table 1.

| Subfamily | The designation "family" is only for convenience in presentation, as other tables also include formulations with alpha-bisabolol. |
|---|---|
| 2 | 1 + 2 + 3, 1 + 2 + 4, 1 + 2 + 5, 1 + 2 + 6, 1 + 2 + 7, 1 + 2 + 8, 1 + 2 + 9, 1 + 2 + 10, 1 + 2 + 11, 1 + 2 + 12, 1 + 2 + 13, 1 + 2 + 14, 1 + 2 + 15, 1 + 2 + 16, 1 + 2 + 17, 1 + 2 + 18, 1 + 2 + 19, 1 + 2 + 20, 1 + 2 + 21, 1 + 2 + 22, 1 + 2 + 23, 1 + 2 + 24, 1 + 2 + 25, 1 + 2 + 26, 1 + 2 + 27, 1 + 2 + 28, 1 + 2 + 29, 1 + 2 + 30, 1 + 2 + 31, 1 + 2 + 32, 1 + 2 + 33, 1 + 2 + 34, 1 + 2 + 35, 1 + 2 + 36, 1 + 2 + 37 |
| 3 | 1 + 3 + 4, 1 + 3 + 5, 1 + 3 + 6, 1 + 3 + 7, 1 + 3 + 8, 1 + 3 + 9, 1 + 3 + 10, 1 + 3 + 11, 1 + 3 + 12, 1 + 3 + 13, 1 + 3 + 14, 1 + 3 + 15, 1 + 3 + 16, 1 + 3 + 17, 1 + 3 + 18, 1 + 3 + 19, 20, 1 + 3 + 21, 1 + 3 + 22, 1 + 3 + 23, 1 + 3 + 24, 1 + 3 + 25, 1 + 3 + 26, 1 + 3 + 27, 1 + 3 + 28, 1 + 3 + 29, 1 + 3 + 30, 1 + 3 + 31, 1 + 3 + 32, 1 + 3 + 33, 1 + 3 + 34, 1 + 3 + 35, 1 + 3 + 36, 1 + 3 + 37. |
| 4 | 1 + 4 + 5, 1 + 4 + 6, 1 + 4 + 7, 1 + 4 + 8, 1 + 4 + 9, 1 + 4 + 10, 1 + 4 + 11, 1 + 4 + 12, 1 + 4 + 13, 1 + 4 + 14, 1 + 4 + 15, 1 + 4 + 16, 1 + 4 + 17, 1 + 4 + 18, 1 + 4 + 19, 1 + 4 + 20, 1 + 4 + 21, 1 + 4 + 22, 1 + 4 + 23, 1 + 4 + 24, 1 + 4 + 25, 1 + 4 + 26, 1 + 4 + 27, 1 + 4 + 28, 1 + 4 + 29, 1 + 4 + 30, 1 + 4 + 31, 1 + 4 + 32, 1 + 4 + 33, 1 + 4 + 34, 1 + 4 + 35, 1 + 4 + 36, 1 + 4 + 37. |

TABLE 2-continued

Alpha-bisabolol family of terpene formulations.
Table 2. Alpha-bisabolol family of terpene formulations.
The numbers refer to the terpenes from Table 1.

The designation "family" is only for convenience in presentation, as other tables also include formulations with alpha-bisabolol.

| Subfamily | Formulations |
|---|---|
| 5 | 1 + 5 + 6, 1 + 5 + 7, 1 + 5 + 8, 1 + 5 + 9, 1 + 5 + 10, 1 + 5 + 11, 1 + 5 + 12, 1 + 5 + 13, 1 + 5 + 14, 1 + 5 + 15, 1 + 5 + 16, 1 + 5 + 17, 1 + 5 + 18, 1 + 5 + 19, 1 + 5 + 20, 1 + 5 + 21, 1 + 5 + 22, 1 + 5 + 23, 1 + 5 + 24, 1 + 5 + 25, 1 + 5 + 26, 1 + 5 + 27, 1 + 5 + 28, 1 + 5 + 29, 1 + 5 + 30, 1 + 5 + 31, 1 + 5 + 32, 1 + 5 + 33, 1 + 5 + 34, 1 + 5 + 35, 1 + 5 + 36, 1 + 5 + 37. |
| 6 | 1 + 6 + 7, 1 + 6 + 8, 1 + 6 + 9, 1 + 6 + 10, 1 + 6 + 11, 1 + 6 + 12, 1 + 6 + 13, 1 + 6 + 14, 1 + 6 + 15, 1 + 6 + 16, 1 + 6 + 17, 1 + 6 + 18, 1 + 6 + 19, 1 + 6 + 20, 1 + 6 + 21, 1 + 6 + 22, 1 + 6 + 23, 1 + 6 + 24, 1 + 6 + 25, 1 + 6 + 26, 1 + 6 + 27, 1 + 6 + 28, 1 + 6 + 29, 1 + 6 + 30, 1 + 6 + 31, 1 + 6 + 32, 1 + 6 + 33, 1 + 6 + 34, 1 + 6 + 35, 1 + 6 + 36, 1 + 6 + 37 |
| 7 | 1 + 7 + 8, 1 + 7 + 9, 1 + 7 + 10, 1 + 7 + 11, 1 + 7 + 12, 1 + 7 + 13, 1 + 7 + 14, 1 + 7 + 15, 1 + 7 + 16, 1 + 7 + 17, 1 + 7 + 18, 1 + 7 + 19, 1 + 7 + 20, 1 + 7 + 21, 1 + 7 + 22, 1 + 7 + 23, 1 + 7 + 24, 1 + 7 + 25, 1 + 7 + 26, 1 + 7 + 27, 1 + 7 + 28, 1 + 7 + 29, 1 + 7 + 30, 1 + 7 + 31, 1 + 7 + 32, 1 + 7 + 33, 1 + 7 + 34, 1 + 7 + 35, 1 + 7 + 36, 1 + 7 + 37. |
| 8 | 1 + 8 + 9, 1 + 8 + 10, 1 + 8 + 11, 1 + 8 + 12, 1 + 8 + 13, 1 + 8 + 14, 1 + 8 + 15, 1 + 8 + 16, 1 + 8 + 17, 1 + 8 + 18, 1 + 8 + 19, 1 + 8 + 20, 1 + 8 + 21, 1 + 8 + 22, 1 + 8 + 23, 1 + 8 + 24, 1 + 8 + 25, 1 + 8 + 26, 1 + 8 + 27, 1 + 8 + 28, 1 + 8 + 29, 1 + 8 + 30, 1 + 8 + 31, 1 + 8 + 32, 1 + 8 + 33, 1 + 8 + 34, 1 + 8 + 35, 1 + 8 + 36, 1 + 8 + 37. |
| 9 | 1 + 9 + 10, 1 + 9 + 11, 1 + 9 + 12, 1 + 9 + 13, 1 + 9 + 14, 1 + 9 + 15, 1 + 9 + 16, 1 + 9 + 17, 1 + 9 + 18, 1 + 9 + 19, 1 + 9 + 20, 1 + 9 + 21, 1 + 9 + 22, 1 + 9 + 23, 1 + 9 + 24, 1 + 9 + 25, 1 + 9 + 26, 1 + 9 + 27, 1 + 9 + 28, 1 + 9 + 29, 1 + 9 + 30, 1 + 9 + 31, 1 + 9 + 32, 1 + 9 + 33, 1 + 9 + 34, 1 + 9 + 35, 1 + 9 + 36, 1 + 9 + 37. |
| 10 | 1 + 10 + 11, 1 + 10 + 12, 1 + 10 + 13, 1 + 10 + 14, 1 + 10 + 15, 1 + 10 + 16, 1 + 10 + 17, 1 + 10 + 18, 1 + 10 + 19, 1 + 10 + 20, 1 + 10 + 21, 1 + 10 + 22, 1 + 10 + 23, 1 + 10 + 24, 1 + 10 + 25, 1 + 10 + 26, 1 + 10 + 27, 1 + 10 + 28, 1 + 10 + 29, 1 + 10 + 30, 1 + 10 + 31, 1 + 10 + 32, 1 + 10 + 33, 1 + 10 + 34, 1 + 10 + 35, 1 + 10 + 36, 1 + 10 + 37. |
| 11 | 1 + 11 + 12, 1 + 11 + 13, 1 + 11 + 14, 1 + 11 + 15, 1 + 11 + 16, 1 + 11 + 17, 1 + 11 + 18, 1 + 11 + 19, 1 + 11 + 20, 1 + 11 + 21, 1 + 11 + 22, 1 + 11 + 23, 1 + 11 + 24, 1 + 11 + 25, 1 + 11 + 26, 1 + 11 + 27, 1 + 11 + 28, 1 + 11 + 29, 1 + 11 + 30, 1 + 11 + 31, 1 + 11 + 32, 1 + 11 + 33, 1 + 11 + 34, 1 + 11 + 35, 1 + 11 + 36, 1 + 11 + 37. |
| 12 | 1 + 12 + 13, 1 + 12 + 14, 1 + 12 + 15, 1 + 12 + 16, 1 + 12 + 17, 1 + 12 + 18, 1 + 12 + 19, 1 + 12 + 20, 1 + 12 + 21, 1 + 12 + 22, 1 + 12 + 23, 1 + 12 + 24, 1 + 12 + 25, 1 + 12 + 26, 1 + 12 + 27, 28, 1 + 12 + 29, 1 + 12 + 30, 1 + 12 + 31, 1 + 12 + 32, 1 + 12 + 33, 1 + 12 + 34, 1 + 12 + 35, 1 + 12 + 36, 1 + 12 + 37. |
| 13 | 1 + 13 + 14, 1 + 13 + 15, 1 + 13 + 16, 1 + 13 + 17, 1 + 13 + 18, 1 + 13 + 19, 1 + 13 + 20, 1 + 13 + 21, 1 + 13 + 22, 1 + 13 + 23, 1 + 13 + 24, 1 + 13 + 25, 1 + 13 + 26, 1 + 13 + 27, 1 + 13 + 28, 1 + 13 + 29, 1 + 13 + 30, 1 + 13 + 31, 1 + 13 + 32, 1 + 13 + 33, 1 + 13 + 34, 1 + 13 + 35, 1 + 13 + 36, 1 + 13 + 37. |
| 14 | 1 + 14 + 15, 1 + 14 + 16, 1 + 14 + 17, 1 + 14 + 18, 1 + 14 + 19, 1 + 14 + 20, 1 + 14 + 21, 1 + 14 + 22, 1 + 14 + 23, 1 + 14 + 24, 1 + 14 + 25, 1 + 14 + 26, 1 + 14 + 27, 1 + 14 + 28, 1 + 14 + 29, 1 + 14 + 30, 1 + 14 + 31, 1 + 14 + 32, 1 + 14 + 33, 1 + 14 + 34, 1 + 14 + 35, 1 + 14 + 36, 1 + 14 + 37. |
| 15 | 1 + 15 + 16, 1 + 15 + 17, 1 + 15 + 18, 1 + 15 + 19, 1 + 15 + 20, 1 + 15 + 21, 1 + 15 + 22, 1 + 15 + 23, 1 + 15 + 24, 1 + 15 + 25, 1 + 15 + 26, 1 + 15 + 27, 1 + 15 + 28, 1 + 15 + 29, 1 + 15 + 30, 1 + 15 + 31, 1 + 15 + 32, 1 + 15 + 33, 1 + 15 + 34, 1 + 15 + 35, 1 + 15 + 36, 1 + 15 + 37. |
| 16 | 1 + 16 + 17, 1 + 16 + 18, 1 + 16 + 19, 1 + 16 + 20, 1 + 16 + 21, 1 + 16 + 22, 1 + 16 + 23, 1 + 16 + 24, 1 + 16 + 25, 1 + 16 + 26, 1 + 16 + 27, 1 + 16 + 28, 1 + 16 + 29, 1 + 16 + 30, 1 + 16 + 31, 1 + 16 + 32, 1 + 16 + 33, 1 + 16 + 34, 1 + 16 + 35, 1 + 16 + 36, 1 + 16 + 37. |
| 17 | 1 + 17 + 18, 1 + 17 + 19, 1 + 17 + 20, 1 + 17 + 21, 1 + 17 + 22, 1 + 17 + 23, 1 + 17 + 24, 1 + 17 + 25, 1 + 17 + 26, 1 + 17 + 27, 1 + 17 + 28, 1 + 17 + 29, 1 + 17 + 30, 1 + 17 + 31, 1 + 17 + 32, 1 + 17 + 33, 1 + 17 + 34, 1 + 17 + 35, 1 + 17 + 36, 1 + 17 + 37. |
| 18 | 1 + 18 + 19, 1 + 18 + 20, 1 + 18 + 21, 1 + 18 + 22, 1 + 18 + 23, 1 + 18 + 24, 1 + 18 + 25, 1 + 18 + 26, 1 + 18 + 27, 1 + 18 + 28, 1 + 18 + 29, 1 + 18 + 30, 1 + 18 + 31, 1 + 18 + 32, 1 + 18 + 33, 1 + 18 + 34, 1 + 18 + 35, 1 + 18 + 36, 1 + 18 + 37. |
| 19 | 1 + 19 + 20, 1 + 19 + 21, 1 + 19 + 22, 1 + 19 + 23, 1 + 19 + 24, 1 + 19 + 25, 1 + 19 + 26, 1 + 19 + 27, 1 + 19 + 28, 1 + 19 + 29, 1 + 19 + 30, 1 + 19 + 31, 1 + 19 + 32, 1 + 19 + 33, 1 + 19 + 34, 1 + 19 + 35, 1 + 19 + 36, 1 + 19 + 37. |
| 20 | 1 + 20 + 21, 1 + 20 + 22, 1 + 20 + 23, 1 + 20 + 24, 1 + 20 + 25, 1 + 20 + 26, 1 + 20 + 27, 1 + 20 + 28, 1 + 20 + 29, 1 + 20 + 30, 1 + 20 + 31, 1 + 20 + 32, 1 + 20 + 33, 1 + 20 + 34, 1 + 20 + 35, 1 + 20 + 36, 1 + 20 + 37. |
| 21 | 1 + 21 + 22, 1 + 21 + 23, 1 + 21 + 24, 1 + 21 + 25, 1 + 21 + 26, 1 + 21 + 27, 1 + 21 + 28, 1 + 21 + 29, 1 + 21 + 30, 1 + 21 + 31, 1 + 21 + 32, 1 + 21 + 33, 1 + 21 + 34, 1 + 21 + 35, 1 + 21 + 36, 1 + 21 + 37. |

TABLE 2-continued

Alpha-bisabolol family of terpene formulations.
Table 2. Alpha-bisabolol family of terpene formulations.
The numbers refer to the terpenes from Table 1.

| Subfamily | The designation "family" is only for convenience in presentation, as other tables also include formulations with alpha-bisbolol. |
|---|---|
| 22 | 1 + 22 + 23, 1 + 22 + 24, 1 + 22 + 25, 1 + 22 + 26, 1 + 22 + 27, 1 + 22 + 28, 1 + 22 + 29, 1 + 22 + 30, 1 + 22 + 31, 1 + 22 + 32, 1 + 22 + 33, 1 + 22 + 34, 1 + 22 + 35, 1 + 22 + 36, 1 + 22 + 37. |
| 23 | 1 + 23 + 24, 1 + 23 + 25, 1 + 23 + 26, 1 + 23 + 27, 1 + 23 + 28, 1 + 23 + 29, 1 + 23 + 30, 1 + 23 + 31, 1 + 23 + 32, 1 + 23 + 33, 1 + 23 + 34, 1 + 23 + 35, 1 + 23 + 36, 1 + 23 + 37. |
| 24 | 1 + 24 + 25, 1 + 24 + 26, 1 + 24 + 27, 1 + 24 + 28, 1 + 24 + 29, 1 + 24 + 30, 1 + 24 + 31, 1 + 24 + 32, 1 + 24 + 33, 1 + 24 + 34, 1 + 24 + 35, 1 + 24 + 36, 1 + 24 + 37. |
| 25 | 1 + 25 + 26, 1 + 25 + 27, 1 + 25 + 28, 1 + 25 + 29, 1 + 25 + 30, 1 + 25 + 31, 1 + 25 + 32, 1 + 25 + 33, 1 + 25 + 34, 1 + 25 + 35, 1 + 25 + 36, 1 + 25 + 37. |
| 26 | 1 + 26 + 27, 1 + 26 + 28, 1 + 26 + 29, 1 + 26 + 30, 1 + 26 + 31, 1 + 26 + 32, 1 + 26 + 33, 1 + 26 + 34, 1 + 26 + 35, 1 + 26 + 36, 1 + 26 + 37. |
| 27 | 1 + 27 + 28, 1 + 27 + 29, 1 + 27 + 30, 1 + 27 + 31, 1 + 27 + 32, 1 + 27 + 33, 1 + 27 + 34, 1 + 27 + 35, 1 + 27 + 36, 1 + 27 + 37. |
| 28 | 1 + 28 + 29, 1 + 28 + 30, 1 + 28 + 31, 1 + 28 + 32, 1 + 28 + 33, 1 + 28 + 34, 1 + 28 + 35, 1 + 28 + 36, 1 + 28 + 37. |
| 29 | 1 + 29 + 30, 1 + 29 + 31, 1 + 29 + 32, 1 + 29 + 33, 1 + 29 + 34, 1 + 29 + 35, 1 + 29 + 36, 1 + 29 + 37. |
| 30 | 1 + 30 + 31, 1 + 30 + 32, 1 + 30 + 33, 1 + 30 + 34, 1 + 30 + 35, 1 + 30 + 36, 1 + 30 + 37. |
| 31 | 1 + 31 + 32, 1 + 31 + 33, 1 + 31 + 34, 1 + 31 + 35, 1 + 31 + 36, 1 + 31 + 37. |
| 32 | 1 + 32 + 33, 1 + 32 + 34, 1 + 32 + 35, 1 + 32 + 36, 1 + 32 + 37. |
| 33 | 1 + 33 + 34, 1 + 33 + 35, 1 + 33 + 36, 1 + 33 + 37. |
| 34 | 1 + 34 + 35, 1 + 34 + 36, 1 + 34 + 37. |
| 35 | 1 + 35 + 36, 1 + 35 + 37. |
| 36 | 1 + 36 + 37. |

TABLE 3

Borneol family of terpene formulations.

Table 3. Borneol family of terpene formulations. The numbers refer to the terpenes from Table 1. The designation "family" is only for convenience in presentation, as other tables also include formulations with borneol

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 3 | 2 + 3 + 4, 2 + 3 + 5, 2 + 3 + 6, 2 + 3 + 7, 2 + 3 + 8, 2 + 3 + 9, 2 + 3 + 10, 2 + 3 + 11, 2 + 3 + 12, 2 + 3 + 13, 2 + 3 + 14, 2 + 3 + 15, 2 + 3 + 16, 2 + 3 + 17, 2 + 3 + 18, 2 + 3 + 19, 2 + 3 + 20, 2 + 3 + 21, 2 + 3 + 22, 2 + 3 + 23, 2 + 3 + 24, 2 + 3 + 25, 2 + 3 + 26, 2 + 3 + 27, 2 + 3 + 28, 2 + 3 + 29, 2 + 3 + 30, 2 + 3 + 31, 2 + 3 + 32, 2 + 3 + 33, 2 + 3 + 34, 2 + 3 + 35, 2 + 3 + 36, 2 + 3 + 37 |
| 4 | 2 + 4 + 5, 2 + 4 + 6, 2 + 4 + 7, 2 + 4 + 8, 2 + 4 + 9, 2 + 4 + 10, 2 + 4 + 11, 2 + 4 + 12, 2 + 4 + 13, 2 + 4 + 4, 2 + 4 + 15, 2 + 4 + 16, 2 + 4 + 17, 2 + 4 + 18, 2 + 4 + 19, 2 + 4 + 20, 2 + 4 + 21, 2 + 4 + 22, 2 + 4 + 23, 2 + 4 + 24, 2 + 4 + 25, 2 + 4 + 26, 2 + 4 + 27, 2 + 4 + 28, 2 + 4 + 29, 2 + 4 + 30, 2 + 4 + 31, 2 + 4 + 32, 2 + 4 + 33, 2 + 4 + 34, 2 + 4 + 35, 2 + 4 + 36, 2 + 4 + 37 |
| 5 | 2 + 5 + 6, 2 + 5 + 7, 2 + 5 + 8, 2 + 5 + 9, 2 + 5 + 10, 2 + 5 + 11, 2 + 5 + 12, 2 + 5 + 13, 2 + 5 + 14, 2 + 5 + 15, 2 + 5 + 16, 2 + 5 + 17, 2 + 5 + 18, 2 + 5 + 19, 2 + 5 + 20, 2 + 5 + 21, 2 + 5 + 22, 2 + 5 + 23, 2 + 5 + 24, 2 + 5 + 25, 2 + 5 + 26, 2 + 5 + 27, 2 + 5 + 28, 2 + 5 + 29, 2 + 5 + 30, 2 + 5 + 31, 2 + 5 + 32, 2 + 5 + 33, 2 + 5 + 34, 2 + 5 + 35, 2 + 5 + 36, 2 + 5 + 37 |
| 6 | 2 + 6 + 7, 2 + 6 + 8, 2 + 6 + 9, 2 + 6 + 10, 2 + 6 + 11, 2 + 6 + 12, 2 + 6 + 13, 2 + 6 + 14, 2 + 6 + 15, 2 + 6 + 16, 2 + 6 + 17, 2 + 6 + 18, 2 + 6 + 19, 2 + 6 + 20, 2 + 6 + 21, 2 + 6 + 22, 2 + 6 + 23, 2 + 6 + 24, 2 + 6 + 25, 2 + 6 + 26, 2 + 6 + 27, 2 + 6 + 28, 2 + 6 + 29, 2 + 6 + 30, 2 + 6 + 31, 2 + 6 + 32, 2 + 6 + 33, 2 + 6 + 34, 2 + 6 + 35, 2 + 6 + 36, 2 + 6 + 37 |
| 7 | 2 + 7 + 8, 2 + 7 + 9, 2 + 7 + 10, 2 + 7 + 11, 2 + 7 + 12, 2 + 7 + 13, 2 + 7 + 14, 2 + 7 + 15, 2 + 7 + 16, 2 + 7 + 17, 2 + 7 + 18, 2 + 7 + 19, 2 + 7 + 20, 2 + 7 + 21, 2 + 7 + 22, 2 + 7 + 23, 2 + 7 + 24, 2 + 7 + 25, 2 + 7 + 26, 2 + 7 + 27, 2 + 7 + 28, 2 + 7 + 29, 2 + 7 + 30, 2 + 7 + 31, 2 + 7 + 32, 2 + 7 + 33, 2 + 7 + 34, 2 + 7 + 35, 2 + 7 + 36, 2 + 7 + 37 |

TABLE 3-continued

Borneol family of terpene formulations.

Table 3. Borneol family of terpene formulations. The numbers refer to the terpenes from Table 1. The designation "family" is only for convenience in presentation, as other tables also include formulations with borneol

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 8 | 2 + 8 + 9, 2 + 8 + 10, 2 + 8 + 11, 2 + 8 + 12, 2 + 8 + 13, 2 + 8 + 14, 2 + 8 + 15, 2 + 8 + 16, 2 + 8 + 17, 2 + 8 + 18, 2 + 8 + 19, 2 + 8 + 20, 2 + 8 + 21, 2 + 8 + 22, 2 + 8 + 23, 2 + 8 + 24, 2 + 8 + 25, 2 + 8 + 26, 2 + 8 + 27, 2 + 8 + 28, 2 + 8 + 29, 2 + 8 + 30, 2 + 8 + 31, 2 + 8 + 32, 2 + 8 + 33, 2 + 8 + 34, 2 + 8 + 35, 2 + 8 + 36, 2 + 8 + 37 |
| 9 | 2 + 9 + 10, 2 + 9 + 11, 2 + 9 + 12, 2 + 9 + 13, 2 + 9 + 14, 2 + 9 + 15, 2 + 9 + 16, 2 + 9 + 17, 2 + 9 + 18, 2 + 9 + 19, 2 + 9 + 20, 2 + 9 + 21, 2 + 9 + 22, 2 + 9 + 23, 2 + 9 + 24, 2 + 9 + 25, 2 + 9 + 26, 2 + 9 + 27, 2 + 9 + 28, 2 + 9 + 29, 2 + 9 + 30, 2 + 9 + 31, 2 + 9 + 32, 2 + 9 + 33, 2 + 9 + 34, 2 + 9 + 35, 2 + 9 + 36, 2 + 9 + 37 |
| 10 | 2 + 10 + 11, 2 + 10 + 12, 2 + 10 + 13, 2 + 10 + 14, 2 + 10 + 15, 2 + 10 + 16, 2 + 10 + 17, 2 + 10 + 18, 2 + 10 + 19, 2 + 10 + 20, 2 + 10 + 21, 2 + 10 + 22, 2 + 10 + 23, 2 + 10 + 24, 2 + 10 + 25, 2 + 10 + 26, 2 + 10 + 27, 2 + 10 + 28, 2 + 10 + 29, 2 + 10 + 30, 2 + 10 + 31, 2 + 10 + 32, 2 + 10 + 33, 2 + 10 + 34, 2 + 10 + 35, 2 + 10 + 36, 2 + 10 + 37 |
| 11 | 2 + 11 + 12, 2 + 11 + 13, 2 + 11 + 14, 2 + 11 + 15, 2 + 11 + 16, 2 + 11 + 17, 2 + 11 + 18, 2 + 11 + 19, 2 + 11 + 20, 2 + 11 + 21, 2 + 11 + 22, 2 + 11 + 23, 2 + 11 + 24, 2 + 11 + 25, 2 + 11 + 26, 2 + 11 + 27, 2 + 11 + 28, 2 + 11 + 29, 2 + 11 + 30, 2 + 11 + 31, 2 + 11 + 32, 2 + 11 + 33, 2 + 11 + 34, 2 + 11 + 35, 2 + 11 + 36, 2 + 11 + 37 |
| 12 | 2 + 12 + 13, 2 + 12 + 14, 2 + 12 + 15, 2 + 12 + 16, 2 + 12 + 17, 2 + 12 + 18, 2 + 12 + 19, 2 + 12 + 20, 2 + 12 + 21, 2 + 12 + 22, 2 + 12 + 23, 2 + 12 + 24, 2 + 12 + 25, 2 + 12 + 26, 2 + 12 + 27, 2 + 12 + 28, 2 + 12 + 29, 2 + 12 + 30, 2 + 12 + 31, 2 + 12 + 32, 2 + 12 + 33, 2 + 12 + 34, 2 + 12 + 35, 2 + 12 + 36, 2 + 12 + 37 |
| 13 | 2 + 13 + 14, 2 + 13 + 15, 2 + 13 + 16, 2 + 13 + 17, 2 + 13 + 18, 2 + 13 + 19, 2 + 13 + 20, 2 + 13 + 21, 2 + 13 + 22, 2 + 13 + 23, 2 + 13 + 24, 2 + 13 + 25, 2 + 13 + 26, 2 + 13 + 27, 2 + 13 + 28, 2 + 13 + 29, 2 + 13 + 30, 2 + 13 + 31, 2 + 13 + 32, 2 + 13 + 33, 2 + 13 + 34, 2 + 13 + 35, 2 + 13 + 36, 2 + 13 + 37 |
| 14 | 2 + 14 + 15, 2 + 14 + 16, 2 + 14 + 17, 2 + 14 + 18, 2 + 14 + 19, 2 + 14 + 20, 2 + 14 + 21, 2 + 14 + 22, 2 + 14 + 23, 2 + 14 + 24, 2 + 14 + 25, 2 + 14 + 26, 2 + 14 + 27, 2 + 14 + 28, 2 + 14 + 29, 2 + 14 + 30, 2 + 14 + 31, 2 + 14 + 32, 2 + 14 + 33, 2 + 14 + 34, 2 + 14 + 35, 2 + 14 + 36, 2 + 14 + 37 |
| 15 | 2 + 15 + 16, 2 + 15 + 17, 2 + 15 + 18, 2 + 15 + 19, 2 + 15 + 20, 2 + 15 + 21, 2 + 15 + 22, 2 + 15 + 23, 2 + 15 + 24, 2 + 15 + 25, 2 + 15 + 26, 2 + 15 + 27, 2 + 15 + 28, 2 + 15 + 29, 2 + 15 + 30, 2 + 15 + 31, 2 + 15 + 32, 2 + 15 + 33, 2 + 15 + 34, 2 + 15 + 35, 2 + 15 + 36, 2 + 15 + 37 |
| 16 | 2 + 16 + 17, 2 + 16 + 18, 2 + 16 + 19, 2 + 16 + 20, 2 + 16 + 21, 2 + 16 + 22, 2 + 16 + 23, 2 + 16 + 24, 2 + 16 + 25, 2 + 16 + 26, 2 + 16 + 27, 2 + 16 + 28, 2 + 16 + 29, 2 + 16 + 30, 2 + 16 + 31, 2 + 16 + 32, 2 + 16 + 33, 2 + 16 + 34, 2 + 16 + 35, 2 + 16 + 36, 2 + 16 + 37 |
| 17 | 2 + 17 + 18, 2 + 17 + 19, 2 + 17 + 20, 2 + 17 + 21, 2 + 17 + 22, 2 + 17 + 23, 2 + 17 + 24, 2 + 17 + 25, 2 + 17 + 26, 2 + 17 + 27, 2 + 17 + 28, 2 + 17 + 29, 2 + 17 + 30, 2 + 17 + 31, 2 + 17 + 32, 2 + 17 + 33, 2 + 17 + 34, 2 + 17 + 35, 2 + 17 + 37 |
| 18 | 2 + 18 + 19, 2 + 18 + 20, 2 + 18 + 21, 2 + 18 + 22, 2 + 18 + 23, 2 + 18 + 24, 2 + 18 + 25, 2 + 18 + 26, 2 + 18 + 27, 2 + 18 + 28, 2 + 18 + 29, 2 + 18 + 30, 2 + 18 + 31, 2 + 18 + 32, 2 + 18 + 33, 2 + 18 + 34, 2 + 18 + 35, 2 + 18 + 36, 2 + 18 + 37 |
| 19 | 2 + 19 + 20, 2 + 19 + 21, 2 + 19 + 22, 2 + 19 + 232 + 19 + 24, 2 + 19 + 25, 2 + 19 + 26, 2 + 19 + 27, 2 + 19 + 28, 2 + 19 + 29, 2 + 19 + 30, 2 + 19 + 31, 2 + 19 + 32, 2 + 19 + 33, 2 + 19 + 34, 2 + 19 + 35, 2 + 19 + 36, 2 + 19 + 37 |
| 20 | 2 + 20 + 21, 2 + 20 + 22, 2 + 20 + 23, 2 + 20 + 24, 2 + 20 + 25, 2 + 20 + 26, 2 + 20 + 27, 2 + 20 + 28, 2 + 20 + 29, 2 + 20 + 30, 2 + 20 + 31, 2 + 20 + 32, 2 + 20 + 33, 2 + 20 + 34, 2 + 20 + 35, 2 + 20 + 36, 2 + 20 + 37 |
| 21 | 2 + 21 + 22, 2 + 21 + 23, 2 + 21 + 24, 2 + 21 + 25, 2 + 21 + 26, 2 + 21 + 27, 2 + 21 + 28, 2 + 21 + 29, 2 + 21 + 30, 2 + 21 + 31, 2 + 21 + 32, 2 + 21 + 33, 2 + 21 + 34, 2 + 21 + 35, 2 + 21 + 36, 2 + 21 + 37 |

TABLE 3-continued

Borneol family of terpene formulations.

Table 3. Borneol family of terpene formulations. The numbers refer to the terpenes from Table 1. The designation "family" is only for convenience in presentation, as other tables also include formulations with borneol

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 22 | 2 + 22 + 23, 2 + 22 + 24, 2 + 22 + 25, 2 + 22 + 26, 2 + 22 + 27, 2 + 22 + 28, 2 + 22 + 29, 2 + 22 + 30, 2 + 22 + 31, 2 + 22 + 32, 2 + 22 + 33, 2 + 22 + 34, 2 + 22 + 35, 2 + 22 + 36, 2 + 22 + 37 |
| 23 | 2 + 23 + 24, 2 + 23 + 25, 2 + 23 + 26, 2 + 23 + 27, 2 + 23 + 28, 2 + 23 + 29, 2 + 23 + 30, 2 + 23 + 31, 2 + 23 + 32, 2 + 23 + 33, 2 + 23 + 34, 2 + 23 + 35, 2 + 23 + 36, 2 + 23 + 37 |
| 24 | 2 + 24 + 25, 2 + 24 + 26, 2 + 24 + 27, 2 + 24 + 28, 2 + 24 + 29, 2 + 24 + 30, 2 + 24 + 31, 2 + 24 + 32, 2 + 24 + 33, 2 + 24 + 34, 2 + 24 + 35, 2 + 24 + 36, 2 + 24 + 37 |
| 25 | 2 + 25 + 26, 2 + 25 + 27, 2 + 25 + 28, 2 + 25 + 29, 2 + 25 + 30, 2 + 25 + 31, 2 + 25 + 32, 2 + 25 + 33, 2 + 25 + 34, 2 + 25 + 35, 2 + 25 + 36, 2 + 25 + 37 |
| 26 | 2 + 26 + 27, 2 + 26 + 28, 2 + 26 + 29, 2 + 26 + 30, 2 + 26 + 31, 2 + 26 + 32, 2 + 26 + 33, 2 + 26 + 34, 2 + 26 + 35, 2 + 26 + 36, 2 + 26 + 37 |
| 27 | 2 + 27 + 28, 2 + 27 + 29, 2 + 27 + 30, 2 + 27 + 31, 2 + 27 + 32, 2 + 27 + 33, 2 + 27 + 34, 2 + 27 + 35, 2 + 27 + 36, 2 + 27 + 37 |
| 28 | 2 + 28 + 29, 2 + 28 + 30, 2 + 28 + 31, 2 + 28 + 32, 2 + 28 + 33, 2 + 28 + 34, 2 + 28 + 35, 2 + 28 + 36, 2 + 28 + 37 |
| 29 | 2 + 29 + 30, 2 + 29 + 31, 2 + 29 + 32, 2 + 29 + 33, 2 + 29 + 34, 2 + 29 + 35, 2 + 29 + 36, 2 + 29 + 37 |
| 30 | 2 + 30 + 31, 2 + 30 + 32, 2 + 30 + 33, 2 + 30 + 34, 2 + 30 + 35, 2 + 30 + 36, 2 + 30 + 37 |
| 31 | 2 + 31 + 32, 2 + 31 + 33, 2 + 31 + 34, 2 + 31 + 35, 2 + 31 + 36, 2 + 31 + 37 |
| 32 | 2 + 32 + 33, 2 + 32 + 34, 2 + 32 + 35, 2 + 32 + 36, 2 + 32 + 37 |
| 33 | 2 + 33 + 34, 2 + 33 + 35, 2 + 33 + 36, 2 + 33 + 37 |
| 34 | 2 + 34 + 35, 2 + 34 + 36, 2 + 34 + 37 |
| 35 | 2 + 35 + 36, 2 + 35 + 37 |
| 36 | 2 + 36 + 37 |

TABLE 4

Camphene family of terpene formulations.

Table 4. Camphene family of terpene formulations. The numbers refer to the terpenes from Table 1.

| Subfamily | Each disclosure of three terpenes represents a distinct formulation. In one embodiment, the formulation that is described by the indicated mixture of the three terpenes does not include any addition terpenes. In other embodiments, it does include additional terpenes. |
|---|---|
| 4 | 3 + 4 + 5, 3 + 4 + 6, 3 + 4 + 7, 3 + 4 + 8, 3 + 4 + 9, 3 + 4 + 10, 3 + 4 + 11, 3 + 4 + 12, 3 + 4 + 13, 3 + 4 + 14, 3 + 4 + 15, 3 + 4 + 16, 3 + 4 + 17, 3 + 4 + 18, 3 + 4 + 18, 3 + 4 + 19, 3 + 4 + 20, 3 + 4 + 21, 3 + 4 + 22, 3 + 4 + 23, 3 + 4 + 24, 3 + 4 + 25, 3 + 4 + 26, 3 + 4 + 27, 3 + 4 + 28, 3 + 4 + 29, 3 + 4 + 30, 3 + 4 + 31, 3 + 4 + 32, 3 + 4 + 33, 3 + 4 + 34, 3 + 4 + 35, 3 + 4 + 36, 3 + 4 + 37 |
| 5 | 3 + 5 + 6, 3 + 5 + 7, 3 + 5 + 8, 3 + 5 + 9, 3 + 5 + 10, 3 + 5 + 11, 3 + 5 + 12, 3 + 5 + 13, 3 + 5 + 14, 3 + 5 + 15, 3 + 5 + 16, 3 + 5 + 17, 3 + 5 + 18, 3 + 5 + 19, 3 + 5 + 20, 3 + 5 + 21, 3 + 5 + 22, 3 + 5 + 23, 3 + 5 + 24, 3 + 5 + 24, 3 + 5 + 25, 3 + 5 + 26, 3 + 5 + 27, 3 + 5 + 28, 3 + 5 + 29, 3 + 5 + 30, 3 + 5 + 31, 3 + 5 + 32, 3 + 5 + 33, 3 + 5 + 34, 3 + 5 + 35, 3 + 5 + 36, 3 + 5 + 37 |
| 6 | 3 + 6 + 7, 3 + 6 + 8, 3 + 6 + 9, 3 + 6 + 10, 3 + 6 + 11, 3 + 6 + 12, 3 + 6 + 13, 3 + 6 + 14, 3 + 6 + 15, 3 + 6 + 16, 3 + 6 + 17, 3 + 6 + 18, 3 + 6 + 19, 3 + 6 + 20, 3 + 6 + 21, 3 + 6 + 22, 3 + 6 + 23, 3 + 6 + 24, 3 + 6 + 25, 3 + 6 + 26, 3 + 6 + 27, 3 + 6 + 28, 3 + 6 + 29, 3 + 6 + 30, 3 + 6 + 31, 3 + 6 + 32, 3 + 6 + 33, 3 + 6 + 34, 3 + 6 + 35, 3 + 6 + 36, 3 + 6 + 37 |
| 7 | 3 + 7 + 8, 3 + 7 + 9, 3 + 7 + 10, 3 + 7 + 11, 3 + 7 + 12, 3 + 7 + 13, 3 + 7 + 14, 3 + 7 + 15, 3 + 7 + 16, 3 + 7 + 17, 3 + 7 + 18, 3 + 7 + 19, 3 + 7 + 20, 3 + 7 + 21, 3 + 7 + 22, 3 + 7 + 23, 3 + 7 + 24, 3 + 7 + 25, 3 + 7 + 26, 3 + 7 + 27, 3 + 7 + 28, 3 + 7 + 29, 3 + 7 + 30, 3 + 7 + 31, 3 + 7 + 32, 3 + 7 + 33, 3 + 7 + 34, 3 + 7 + 35, 3 + 7 + 36, 3 + 7 + 37 |

TABLE 4-continued

Camphene family of terpene formulations.

Table 4. Camphene family of terpene formulations. The numbers refer to the terpenes from Table 1.

Each disclosure of three terpenes represents a distinct formulation. In one embodiment, the formulation that is described by the indicated mixture of the three terpenes does not include any addition terpenes. In other embodiments, it does include additional terpenes.

| Subfamily | |
|---|---|
| 8 | 3 + 8 + 9, 3 + 8 + 10, 3 + 8 + 11, 3 + 8 + 12, 3 + 8 + 13, 3 + 8 + 14, 3 + 8 + 15, 3 + 8 + 16, 3 + 8 + 17, 3 + 8 + 18, 3 + 8 + 19, 3 + 8 + 20, 3 + 8 + 21, 3 + 8 + 22, 3 + 8 + 23, 3 + 8 + 24, 3 + 8 + 25, 3 + 8 + 26, 3 + 8 + 27, 3 + 8 + 28, 3 + 8 + 29, 3 + 8 + 30, 3 + 8 + 31, 3 + 8 + 32, 3 + 8 + 33, 3 + 8 + 34, 3 + 8 + 35, 3 + 8 + 36, 3 + 8 + 37 |
| 9 | 3 + 9 + 10, 3 + 9 + 11, 3 + 9 + 12, 3 + 9 + 13, 3 + 9 + 14, 3 + 9 + 15, 3 + 9 + 16, 3 + 9 + 17, 3 + 9 + 18, 3 + 9 + 19, 3 + 9 + 20, 3 + 9 + 21, 3 + 9 + 22, 3 + 9 + 23, 3 + 9 + 24, 3 + 9 + 25, 3 + 9 + 26, 3 + 9 + 27, 3 + 9 + 28, 3 + 9 + 29, 3 + 9 + 30, 3 + 9 + 31, 3 + 9 + 32, 3 + 9 + 33, 3 + 9 + 34, 3 + 9 + 35, 3 + 9 + 36, 3 + 9 + 37 |
| 10 | 3 + 10 + 11, 3 + 10 + 12, 3 + 10 + 13, 3 + 10 + 14, 3 + 10 + 15, 3 + 10 + 16, 3 + 10 + 17, 3 + 10 + 18, 3 + 10 + 19, 3 + 10 + 20, 3 + 10 + 21, 3 + 10 + 22, 3 + 10 + 23, 3 + 10 + 24, 3 + 10 + 25, 3 + 10 + 26, 3 + 10 + 27, 3 + 10 + 28, 3 + 10 + 29, 3 + 10 + 30, 3 + 10 + 31, 3 + 10 + 32, 3 + 10 + 33, 3 + 10 + 34, 3 + 10 + 35, 3 + 10 + 36, 3 + 10 + 37 |
| 11 | 3 + 11 + 12, 3 + 11 + 13, 3 + 11 + 11 + 15, 3 + 16, 3 + 14, 3 + 11 + 11 + 17, 3 + 11 + 18, 3 + 11 + 19, 3 + 11 + 20, 3 + 11 + 21, 3 + 11 + 22, 3 + 11 + 23, 3 + 11 + 24, 3 + 11 + 25, 3 + 11 + 26, 3 + 11 + 27, 3 + 11 + 28, 3 + 11 + 29, 3 + 11 + 29, 3 + 11 + 30, 3 + 11 + 31, 3 + 11 + 32, 3 + 11 + 33, 3 + 11 + 34, 3 + 11 + 35, 3 + 11 + 36, 3 + 11 + 36, 3 + 11 + 37 |
| 12 | 3 + 12 + 13, 3 + 12 + 14, 3 + 12 + 15, 3 + 12 + 16, 3 + 12 + 17, 3 + 12 + 18, 3 + 12 + 19, 3 + 12 + 20, 3 + 12 + 21, 3 + 12 + 22, 3 + 12 + 23, 3 + 12 + 24, 3 + 12 + 25, 3 + 12 + 26, 3 + 12 + 27, 3 + 12 + 28, 3 + 12 + 29, 3 + 12 + 29, 3 + 12 + 30, 3 + 12 + 31, 3 + 12 + 32, 3 + 12 + 33, 3 + 12 + 34, 3 + 12 + 35, 3 + 12 + 36, 3 + 12 + 37 |
| 13 | 3 + 13 + 14, 3 + 13 + 15, 3 + 13 + 16, 3 + 13 + 17, 3 + 13 + 18, 3 + 13 + 19, 3 + 13 + 20, 2 + 13 + 21, 3 + 13 + 22, 3 + 13 + 23, 3 + 13 + 24, 3 + 13 + 25, 3 + 13 + 26, 3 + 13 + 27, 3 + 13 + 28, 3 + 13 + 29, 3 + 13 + 30, 3 + 13 + 31, 3 + 13 + 32, 3 + 13 + 33, 3 + 13 + 33, 3 + 13 + 34, 3 + 13 + 35, 3 + 13 + 36, 3 + 13 + 37 |
| 14 | 3 + 14 + 15, 3 + 14 + 16, 3 + 14 + 17, 3 + 14 + 18, 3 + 14 + 19, 3 + 14 + 20, 3 + 14 + 21, 3 + 14 + 22, 3 + 14 + 23, 3 + 14 + 24, 3 + 14 + 25, 3 + 14 + 26, 3 + 14 + 27, 3 + 14 + 28, 3 + 14 + 29, 3 + 14 + 30, 3 + 14 + 31, 3 + 14 + 32, 3 + 14 + 33, 3 + 14 + 34, 3 + 14 + 35, 3 + 14 + 36, 3 + 14 + 37 |
| 15 | 3 + 15 + 16, 3 + 15 + 17, 3 + 15 + 18, 3 + 15 + 19, 3 + 15 + 20, 3 + 15 + 21, 3 + 15 + 22, 3 + 15 + 23, 3 + 15 + 24, 3 + 15 + 25, 3 + 15 + 26, 3 + 15 + 27, 3 + 15 + 28, 3 + 15 + 29, 3 + 15 + 30, 3 + 15 + 31, 3 + 15 + 32, 3 + 15 + 33, 3 + 15 + 34, 3 + 15 + 35, 3 + 15 + 36, 3 + 15 + 37 |
| 16 | 3 + 16 + 17, 3 + 16 + 18, 3 + 16 + 19, 3 + 16 + 20, 3 + 16 + 21, 3 + 16 + 22, 3 + 16 + 23, 3 + 16 + 24, 3 + 16 + 25, 3 + 16 + 26, 3 + 16 + 27, 3 + 16 + 28, 3 + 16 + 29, 3 + 16 + 30, 3 + 16 + 31, 3 + 16 + 32, 3 + 16 + 33, 3 + 16 + 34, 3 + 16 + 35, 3 + 16 + 36, 3 + 16 + 37 |
| 17 | 3 + 17 + 18, 3 + 17 + 19, 3 + 17 + 20, 3 + 17 + 21, 3 + 17 + 22, 3 + 17 + 23, 3 + 17 + 24, 3 + 17 + 25, 3 + 17 + 26, 3 + 17 + 27, 3 + 17 + 28, 3 + 17 + 29, 3 + 17 + 30, 3 + 17 + 31, 3 + 17 + 32, 3 + 17 + 33, 3 + 17 + 34, 3 + 17 + 35, 3 + 17 + 37 |
| 18 | 3 + 18 + 19, 3 + 18 + 20, 3 + 18 + 21, 3 + 18 + 22, 3 + 18 + 23, 3 + 18 + 24, 3 + 18 + 25, 3 + 18 + 26, 3 + 18 + 27, 3 + 18 + 28, 3 + 18 + 29, 3 + 18 + 30, 3 + 18 + 31, 3 + 18 + 32, 3 + 18 + 33, 3 + 18 + 34 + 18 + 35, 3 + 18 + 36, 3 + 18 + 37 |
| 19 | 3 + 19 + 20, 3 + 19 + 21, 3 + 19 + 22, 3 + 19 + 23, 3 + 19 + 24, 3 + 19 + 25, 3 + 19 + 26, 3 + 19 + 27, 3 + 19 + 28, 3 + 19 + 29, 3 + 19 + 30, 3 + 19 + 31, 3 + 19 + 32, 3 + 19 + 33, 3 + 19 + 34, 3 + 19 + 35, 3 + 19 + 36, 3 + 19 + 37 |
| 20 | 3 + 20 + 21, 3 + 20 + 22, 3 + 20 + 23, 3 + 20 + 24, 3 + 20 + 25, 3 + 20 + 26, 3 + 20 + 27, 3 + 20 + 28, 3 + 20 + 29, 3 + 20 + 30, 3 + 20 + 31, 3 + 20 + 32, 3 + 20 + 33, 3 + 20 + 34, 3 + 20 + 35, 3 + 20 + 36, 3 + 20 + 37 |
| 21 | 3 + 21 + 22, 3 + 21 + 23, 3 + 21 + 24, 3 + 21 + 25, 3 + 21 + 26, 3 + 21 + 27, 3 + 21 + 28, 3 + 21 + 29, 3 + 21 + 30, 3 + 21 + 31, 3 + 21 + 32, 3 + 21 + 33, 3 + 21 + 34, 3 + 21 + 35, 3 + 21 + 36, 3 + 21 + 37 |
| 22 | 3 + 22 + 23, 3 + 22 + 24, 3 + 22 + 25, 3 + 22 + 26, 3 + 22 + 27, 3 + 22 + 28, 3 + 22 + 29, 3 + 22 + 30, 3 + 22 + 31, 3 + 22 + 32, 3 + 22 + 33, 3 + 22 + 34, 3 + 22 + 35, 3 + 22 + 36, 3 + 22 + 37 |
| 23 | 3 + 23 + 24, 3 + 23 + 25, 3 + 23 + 26, 3 + 23 + 27, 3 + 23 + 28, 3 + 23 + 29, 3 + 23 + 30, 3 + 23 + 31, 3 + 23 + 32, 3 + 23 + 33, 3 + 23 + 34, 3 + 23 + 35, 3 + 23 + 36, 3 + 23 + 37 |
| 24 | 3 + 24 + 25, 3 + 24 + 26, 3 + 24 + 27, 3 + 24 + 28, 3 + 24 + 29, 3 + 24 + 30, 3 + 24 + 31, 3 + 24 + 32, 3 + 24 + 33, 3 + 24 + 34, 3 + 24 + 35, 3 + 24 + 36, 3 + 24 + 37 |
| 25 | 3 + 25 + 26, 3 + 25 + 27, 3 + 25 + 28, 3 + 25 + 29, 3 + 25 + 30, 3 + 25 + 31, 3 + 25 + 32, 3 + 25 + 33, 3 + 25 + 34, 3 + 25 + 35, 3 + 25 + 36, 3 + 25 + 37 |

TABLE 4-continued

Camphene family of terpene formulations.

Table 4. Camphene family of terpene formulations. The numbers refer to the terpenes from Table 1.

| Subfamily | Each disclosure of three terpenes represents a distinct formulation. In one embodiment, the formulation that is described by the indicated mixture of the three terpenes does not include any addition terpenes. In other embodiments, it does include additional terpenes. |
|---|---|
| 26 | 3 + 26 + 27, 3 + 26 + 28, 3 + 26 + 29, 3 + 26 + 30, 3 + 26 + 31, 3 + 26 + 32, 3 + 26 + 33, 3 + 26 + 34, 3 + 26 + 35, 3 + 26 + 36, 3 + 26 + 37 |
| 27 | 3 + 27 + 28, 3 + 27 + 29, 3 + 27 + 30, 3 + 27 + 31, 3 + 27 + 32, 3 + 27 + 33, 3 + 27 + 34, 3 + 27 + 35, 3 + 27 + 36, 3 + 27 + 37 |
| 28 | 3 + 28 + 29, 3 + 28 + 30, 3 + 28 + 31, 3 + 28 + 32, 3 + 28 + 33, 3 + 28 + 34, 3 + 28 + 35, 3 + 28 + 36, 3 + 28 + 37 |
| 29 | 3 + 29 + 30, 3 + 29 + 31, 3 + 29 + 32, 3 + 29 + 33, 3 + 29 + 34, 3 + 29 + 35, 3 + 29 + 36, 3 + 29 + 37 |
| 30 | 3 + 30 + 31, 3 + 30 + 32, 3 + 30 + 33, 3 + 30 + 34, 3 + 30 + 35, 3 + 30 + 36, 3 + 30 + 37, 31 3 + 31 + 32, 3 + 31 + 33, 3 + 31 + 34, 3 + 31 + 35, 3 + 31 + 36, 3 + 31 + 37 |
| 32 | 3 + 32 + 33, 3 + 32 + 34, 3 + 32 + 35, 3 + 32 + 36, 3 + 32 + 37 |
| 33 | 3 + 33 + 34, 3 + 33 + 35, 3 + 33 + 36, 3 + 33 + 37 |
| 34 | 3 + 34 + 35, 3 + 34 + 36, 3 + 34 + 37 |
| 35 | 3 + 35 + 36, 3 + 35 + 37 |

TABLE 5

Camphor family of terpene formulations.

Table 5. Camphor family of terpene formulations. The numbers refer to the terpenes from Table 1. The designation "family" is only for convenience in presentation, as other tables also include formulations with camphor.

| Subfamily | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 5 | 4 + 5 + 6, 4 + 5 + 7, 4 + 5 + 8, 4 + 5 + 9, 4 + 5 + 10, 4 + 5 + 11, 4 + 5 + 12, 4 + 5 + 13, 4 + 5 + 14, 4 + 5 + 15, 4 + 5 + 16, 4 + 5 + 17, 4 + 5 + 18, 4 + 5 + 19, 4 + 5 + 20, 4 + 5 + 21, 4 + 5 + 22, 4 + 5 + 23, 4 + 5 + 24, 4 + 5 + 25, 4 + 5 + 26, 4 + 5 + 27, 4 + 5 + 28, 4 + 5 + 29, 4 + 5 + 30, 4 + 5 + 31, 4 + 5 + 32, 4 + 5 + 33, 4 + 5 + 34, 4 + 5 + 35, 4 + 5 + 36, 4 + 5 + 37 |
| 6 | 4 + 6 + 7, 4 + 6 + 8, 4 + 6 + 9, 4 + 6 + 10, 4 + 6 + 11, 4 + 6 + 12, 4 + 6 + 13, 4 + 6 + 14, 4 + 6 + 15, 4 + 6 + 16, 4 + 6 + 17, 4 + 6 + 18, 4 + 6 + 19, 4 + 6 + 20, 4 + 6 + 21, 4 + 6 + 22, 4 + 6 + 23, 4 + 6 + 24, 4 + 6 + 25, 4 + 6 + 26, 4 + 6 + 27, 4 + 6 + 28, 4 + 6 + 29, 4 + 6 + 30, 4 + 6 + 31, 4 + 6 + 32, 4 + 6 + 33, 4 + 6 + 34, 4 + 6 + 36, 4 + 6 + 37 |
| 7 | 4 + 7 + 8, 4 + 7 + 9, 4 + 7 + 10, 4 + 7 + 11, 4 + 7 + 12, 4 + 7 + 13, 4 + 7 + 14, 4 + 7 + 15, 4 + 7 + 16, 4 + 7 + 17, 4 + 7 + 18, 4 + 7 + 19, 4 + 7 + 20, 4 + 7 + 21, 4 + 7 + 22, 4 + 7 + 23, 4 + 7 + 24, 4 + 7 + 25, 4 + 7 + 26, 4 + 7 + 27, 4 + 7 + 28, 4 + 7 + 29, 4 + 7 + 30, 4 + 7 + 31, 4 + 7 + 32, 4 + 7 + 33, 4 + 7 + 34, 4 + 7 + 35, 4 + 7 + 36, 4 + 7 + 37 |
| 8 | 4 + 8 + 9, 4 + 8 + 10, 4 + 8 + 11, 4 + 8 + 12, 4 + 8 + 13, 4 + 8 + 14, 4 + 8 + 15, 4 + 8 + 16, 4 + 8 + 17, 4 + 8 + 18, 4 + 8 + 19, 4 + 8 + 20, 4 + 8 + 21, 4 + 8 + 22, 4 + 8 + 23, 4 + 8 + 24, 4 + 8 + 25, 4 + 8 + 26, 4 + 8 + 27, 4 + 8 + 28, 4 + 8 + 29, 4 + 8 + 30, 4 + 8 + 31, 4 + 8 + 32, 4 + 8 + 33, 4 + 8 + 34, 4 + 8 + 35, 4 + 8 + 36, 4 + 8 + 37 |

TABLE 5-continued

Camphor family of terpene formulations.

Table 5. Camphor family of terpene formulations. The numbers refer to the terpenes from Table 1. The designation "family" is only for convenience in presentation, as other tables also include formulations with camphor.

| Subfamily | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 9 | 4 + 9 + 10, 4 + 9 + 11, 4 + 9 + 12, 4 + 9 + 13, 4 + 9 + 14, 4 + 9 + 15, 4 + 9 + 16, 4 + 9 + 17, 4 + 9 + 18, 4 + 9 + 19, 4 + 9 + 20, 4 + 9 + 21, 4 + 9 + 22, 4 + 9 + 23, 4 + 9 + 24, 4 + 9 + 25, 4 + 9 + 26, 4 + 9 + 27, 4 + 9 + 28, 4 + 9 + 29, 4 + 9 + 30, 4 + 9 + 31, 4 + 9 + 32, 4 + 9 + 33, 4 + 9 + 34, 4 + 9 + 35, 4 + 9 + 36, 4 + 9 + 37 |
| 10 | 4 + 10 + 11, 4 + 10 + 12, 4 + 10 + 13, 4 + 10 + 14, 4 + 10 + 15, 4 + 10 + 16, 4 + 10 + 17, 4 + 10 + 18, 4 + 10 + 19, 4 + 10 + 20, 4 + 10 + 21, 4 + 10 + 22, 4 + 10 + 23, 4 + 10 + 24, 4 + 10 + 25, 4 + 10 + 26, 4 + 10 + 27, 4 + 10 + 28, 4 + 10 + 29, 4 + 10 + 30, 4 + 10 + 31, 4 + 10 + 32, 4 + 10 + 33, 4 + 10 + 34, 4 + 10 + 35, 4 + 10 + 36, 4 + 10 + 37 |
| 11 | 4 + 11 + 12, 4 + 11 + 13, 4 + 11 + 14, 4 + 11 + 15, 4 + 11 + 16, 4 + 11 + 17, 4 + 11 + 18, 4 + 11 + 19, 4 + 11 + 20, 4 + 11 + 21, 4 + 11 + 22, 4 + 11 + 23, 4 + 11 + 24, 4 + 11 + 25, 4 + 11 + 26, 4 + 11 + 27, 4 + 11 + 28, 4 + 11 + 29, 4 + 11 + 30, 4 + 11 + 31, 4 + 11 + 32, 4 + 11 + 33, 4 + 11 + 34, 4 + 11 + 35, 4 + 11 + 36, 4 + 11 + 37 |
| 12 | 4 + 12 + 13, 4 + 12 + 14, 4 + 12 + 15, 4 + 12 + 16, 4 + 12 + 17, 4 + 12 + 18, 4 + 12 + 19, 4 + 12 + 20, 4 + 12 + 21, 4 + 12 + 22, 4 + 12 + 23, 4 + 12 + 24, 4 + 12 + 25, 4 + 12 + 26, 4 + 12 + 27, 4 + 12 + 28, 4 + 12 + 29, 4 + 12 + 30, 4 + 12 + 31, 4 + 12 + 32, 4 + 12 + 33, 4 + 12 + 34, 4 + 12 + 35, 4 + 12 + 36, 4 + 12 + 37 |
| 13 | 4 + 13 + 14, 4 + 13 + 15, 4 + 13 + 16, 4 + 13 + 17, 4 + 13 + 18, 4 + 13 + 19, 4 + 13 + 20, 4 + 13 + 20, 4 + 13 + 21, 4 + 13 + 22, 4 + 13 + 23, 4 + 13 + 24, 4 + 13 + 25, 4 + 13 + 6, 4 + 13 + 27, 4 + 13 + 28, 4 + 13 + 29, 4 + 13 + 30, 4 + 13 + 31, 4 + 13 + 32, 4 + 13 + 33, 4 + 13 + 34, 4 + 13 + 35, 4 + 13 + 36, 4 + 13 + 37 |
| 14 | 4 + 14 + 15, 4 + 14 + 16, 4 + 14 + 17, 4 + 14 + 18, 4 + 14 + 19, 4 + 14 + 20, 4 + 14 + 21, 4 + 14 + 22, 4 + 14 + 23, 4 + 14 + 24, 4 + 14 + 25, 4 + 14 + 26, 4 + 14 + 27, 4 + 14 + 28, 4 + 14 + 29, 4 + 14 + 30, 4 + 14 + 31, 4 + 14 + 32, 4 + 14 + 33, 4 + 14 + 34, 4 + 14 + 35, 4 + 14 + 36, 4 + 14 + 37 |
| 15 | 4 + 15 + 16, 4 + 15 + 17, 4 + 15 + 18, 4 + 15 + 19, 4 + 15 + 20, 4 + 15 + 21, 4 + 15 + 22, 4 + 15 + 23, 4 + 15 + 24, 4 + 15 + 25, 4 + 15 + 26, 4 + 15 + 27, 4 + 15 + 28, 4 + 15 + 29, 4 + 15 + 30, 4 + 15 + 31, 4 + 15 + 32, 4 + 15 + 33, 4 + 15 + 34, 4 + 15 + 35, 4 + 15 + 36, 4 + 15 + 37 |
| 16 | 4 + 16 + 17, 4 + 16 + 18, 4 + 16 + 19, 4 + 16 + 20, 4 + 16 + 21, 4 + 16 + 22, 4 + 16 + 23, 4 + 16 + 24, 4 + 16 + 25, 4 + 16 + 26, 4 + 16 + 27, 4 + 16 + 28, 4 + 16 + 29, 4 + 16 + 30, 4 + 16 + 31, 4 + 16 + 32, 4 + 16 + 33, 4 + 16 + 34, 4 + 16 + 35, 4 + 16 + 36, 4 + 16 + 37 |

TABLE 5-continued

Camphor family of terpene formulations.

Table 5. Camphor family of terpene formulations. The numbers refer to the terpenes from Table 1. The designation "family" is only for convenience in presentation, as other tables also include formulations with camphor.

| Subfamily | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 17 | 4 + 17 + 18, 4 + 17 + 19, 4 + 17 + 20, 4 + 17 + 21, 4 + 17 + 22, 4 + 17 + 23, 4 + 17 + 24, 4 + 17 + 25, 4 + 17 + 26, 4 + 17 + 27, 4 + 17 + 28, 4 + 17 + 29, 4 + 17 + 30, 4 + 17 + 31, 4 + 17 + 32, 4 + 17 + 33, 4 + 17 + 34, 4 + 17 + 35, 4 + 17 + 36, 4 + 17 + 37 |
| 18 | 4 + 18 + 19, 4 + 18 + 20, 4 + 18 + 21, 4 + 18 + 22, 4 + 18 + 23, 4 + 18 + 24, 4 + 18 + 25, 4 + 18 + 26, 4 + 18 + 27, 4 + 18 + 28, 4 + 18 + 29, 4 + 18 + 30, 4 + 18 + 31, 4 + 18 + 32, 4 + 18 + 33, 4 + 18 + 34, 4 + 18 + 35, 4 + 18 + 36, 4 + 18 + 37 |
| 19 | 4 + 19 + 20, 4 + 19 + 21, 4 + 19 + 22, 4 + 19 + 23, 4 + 19 + 24, 4 + 19 + 25, 4 + 19 + 26, 4 + 19 + 27, 4 + 19 + 28, 4 + 19 + 29, 4 + 19 + 30, 4 + 19 + 31, 4 + 19 + 32, 4 + 19 + 33, 4 + 19 + 34, 4 + 19 + 35, 4 + 19 + 36, 4 + 19 + 37 |
| 20 | 4 + 20 + 21, 4 + 20 + 22, 4 + 20 + 23, 4 + 20 + 24, 4 + 20 + 25, 4 + 20 + 26, 4 + 20 + 27, 4 + 20 + 28, 4 + 20 + 29, 4 + 20 + 30, 4 + 20 + 31, 4 + 20 + 32, 4 + 20 + 33, 4 + 20 + 34, 4 + 20 + 35, 4 + 20 + 36, 4 + 20 + 37 |
| 21 | 4 + 21 + 22, 4 + 21 + 23, 4 + 21 + 24, 4 + 21 + 25, 4 + 21 + 26, 4 + 21 + 27, 4 + 21 + 28, 4 + 21 + 29, 4 + 21 + 30, 4 + 21 + 31, 4 + 21 + 32, 4 + 21 + 33, 4 + 21 + 34, 4 + 21 + 35, 4 + 21 + 36, 4 + 21 + 37 |
| 22 | 4 + 22 + 23, 4 + 22 + 24, 4 + 22 + 25, 4 + 22 + 26, 4 + 22 + 27, 4 + 22 + 28, 4 + 22 + 29, 4 + 22 + 30, 4 + 22 + 31, 4 + 22 + 32, 4 + 22 + 33, 4 + 22 + 34, 4 + 22 + 35, 4 + 22 + 36, 4 + 22 + 37 |
| 23 | 4 + 23 + 24, 4 + 23 + 25, 4 + 23 + 26, 4 + 23 + 27, 4 + 23 + 28, 4 + 23 + 29, 4 + 23 + 30, 4 + 23 + 31, 4 + 23 + 32, 4 + 23 + 33, 4 + 23 + 34, 4 + 23 + 35, 4 + 23 + 36, 4 + 23 + 37 |
| 24 | 4 + 24 + 25, 4 + 24 + 26, 4 + 24 + 27, 4 + 24 + 28, 4 + 24 + 29, 4 + 24 + 30, 4 + 24 + 31, 4 + 24 + 32, 4 + 24 + 33, 4 + 24 + 34, 4 + 24 + 35, 4 + 24 + 36, 4 + 24 + 37 |
| 25 | 4 + 25 + 26, 4 + 25 + 27, 4 + 25 + 28, 4 + 25 + 29, 4 + 25 + 30, 4 + 25 + 31, 4 + 25 + 32, 4 + 25 + 33, 4 + 25 + 34, 4 + 25 + 35, 4 + 25 + 36, 4 + 25 + 37 |
| 26 | 4 + 26 + 27, 4 + 26 + 28, 4 + 26 + 29, 4 + 26 + 30, 4 + 26 + 31, 4 + 26 + 32, 4 + 26 + 33, 4 + 26 + 34, 4 + 26 + 35, 4 + 26 + 36, 4 + 26 + 37 |
| 27 | 4 + 27 + 28, 4 + 27 + 29, 4 + 27 + 30, 4 + 27 + 31, 4 + 27 + 32, 4 + 27 + 33, 4 + 27 + 34, 4 + 27 + 35, 4 + 27 + 36, 4 + 27 + 37 |
| 28 | 4 + 28 + 29, 4 + 28 + 30, 4 + 28 + 31, 4 + 28 + 32, 4 + 28 + 33, 4 + 28 + 34, 4 + 28 + 35, 4 + 28 + 36, 4 + 28 + 37 |
| 29 | 4 + 29 + 30, 4 + 29 + 31, 4 + 29 + 32, 4 + 29 + 33, 4 + 29 + 34, 4 + 29 + 35, 4 + 29 + 36, 4 + 29 + 37 |
| 30 | 4 + 30 + 31, 4 + 30 + 32, 4 + 30 + 33, 4 + 30 + 34, 4 + 30 + 35, 4 + 30 + 36, 4 + 30 + 37 |
| 31 | 4 + 31 + 32, 4 + 31 + 33, 4 + 31 + 34, 4 + 31 + 35, 4 + 31 + 36, 4 + 31 + 37 |
| 32 | 4 + 32 + 33, 4 + 32 + 34, 4 + 32 + 35, 4 + 32 + 36, 4 + 32 + 37 |

TABLE 5-continued

Camphor family of terpene formulations.

Table 5. Camphor family of terpene formulations. The numbers refer to the terpenes from Table 1. The designation "family" is only for convenience in presentation, as other tables also include formulations with camphor.

| Subfamily | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 33 | 4 + 33 + 34, 4 + 33 + 35, 4 + 33 + 36, 4 + 33 + 37 |
| 34 | 4 + 34 + 35, 4 + 34 + 36, 4 + 34 + 37 |
| 35 | 4 + 35 + 36, 4 + 35 + 37 |
| 36 | 4 + 36 + 37 |

TABLE 6

Delta-3-carene family of terpene formulations.

Table 6. Delta-3-carene family of terpene formulations. The numbers refer to the terpenes from Table 1. The designation "family" is only for convenience in presentation, as other tables also include formulations with delta-3-carene.

| Subfamily | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 6 | 5 + 6 + 7, 5 + 6 + 8, 5 + 6 + 9, 5 + 6 + 10, 5 + 6 + 11, 5 + 6 + 12, 5 + 6 + 13, 5 + 6 + 14, 5 + 6 + 15, 5 + 6 + 16, 5 + 6 + 17, 5 + 6 + 18, 5 + 6 + 19, 5 + 6 + 20, 5 + 6 + 21, 5 + 6 + 22, 5 + 6 + 23, 5 + 6 + 24, 5 + 6 + 25, 5 + 6 + 26, 5 + 6 + 27, 5 + 6 + 28, 5 + 6 + 29, 5 + 6 + 30, 5 + 6 + 31, 5 + 6 + 32, 5 + 6 + 33, 5 + 6 + 34, 5 + 6 + 35, 5 + 6 + 36, 5 + 6 + 37 |
| 7 | 5 + 7 + 8, 5 + 7 + 9, 5 + 7 + 10, 5 + 7 + 11, 5 + 7 + 12, 5 + 7 + 13, 5 + 7 + 14, 5 + 7 + 15, 5 + 7 + 16, 5 + 7 + 17, 5 + 7 + 18, 5 + 7 + 19, 5 + 7 + 20, 5 + 7 + 21, 5 + 7 + 22, 5 + 7 + 23, 5 + 7 + 24, 5 + 7 + 25, 5 + 7 + 26, 5 + 7 + 27, 5 + 7 + 28, 5 + 7 + 29, 5 + 7 + 30, 5 + 7 + 31, 5 + 7 + 32, 5 + 7 + 33, 5 + 7 + 34, 5 + 7 + 35, 5 + 7 + 36, 5 + 7 + 37 |
| 8 | 5 + 8 + 9, 5 + 8 + 10, 5 + 8 + 11, 5 + 8 + 12, 5 + 8 + 13, 5 + 8 + 14, 5 + 8 + 15, 5 + 8 + 16, 5 + 8 + 17, 5 + 8 + 18, 5 + 8 + 19, 5 + 8 + 20, 5 + 8 + 21, 5 + 8 + 22, 5 + 8 + 23, 5 + 8 + 24, 5 + 8 + 25, 5 + 8 + 26, 5 + 8 + 27, 5 + 8 + 28, 5 + 8 + 29, 5 + 8 + 30, 5 + 8 + 31, 5 + 8 + 32, 5 + 8 + 33, 5 + 8 + 34, 5 + 8 + 35, 5 + 8 + 36, 5 + 8 + 37 |
| 9 | 5 + 9 + 10, 5 + 9 + 11, 5 + 9 + 12, 5 + 9 + 13, 5 + 9 + 14, 5 + 9 + 15, 5 + 9 + 16, 5 + 9 + 17, 5 + 9 + 18, 5 + 9 + 19, 5 + 9 + 20, 5 + 9 + 21, 5 + 9 + 22, 5 + 9 + 23, 5 + 9 + 24, 5 + 9 + 25, 5 + 9 + 26, 5 + 9 + 27, 5 + 9 + 28, 5 + 9 + 29, 5 + 9 + 30, 5 + 9 + 31, 5 + 9 + 32, 5 + 9 + 33, 5 + 9 + 34, 5 + 9 + 35, 5 + 9 + 36, 5 + 9 + 37 |
| 10 | 5 + 10 + 11, 5 + 10 + 12, 5 + 10 + 13, 5 + 10 + 14, 5 + 10 + 15, 5 + 10 + 16, 5 + 10 + 17, 5 + 10 + 18, 5 + 10 + 19, 5 + 10 + 20, 5 + 10 + 21, 5 + 10 + 22, 5 + 10 + 23, 5 + 10 + 24, 5 + 10 + 25, 5 + 10 + 26, 5 + 10 + 27, 5 + 10 + 28, 5 + 10 + 29, 5 + 10 + 30, 5 + 10 + 31, 5 + 10 + 32, 5 + 10 + 33, 5 + 10 + 34, 5 + 10 + 35, 5 + 10 + 36, 5 + 10 + 37 |
| 11 | 5 + 11 + 12, 5 + 11 + 13, 5 + 11 + 14, 5 + 11 + 15, 5 + 11 + 16, 5 + 11 + 17, 5 + 11 + 18, 5 + 11 + 19, 5 + 11 + 20, 5 + 11 + 21, 5 + 11 + 22, 5 + 11 + 23, 5 + 11 + 24, 5 + 11 + 25, 5 + 11 + 26, 5 + 11 + 27, 5 + 11 + 28, 5 + 11 + 29, 5 + 11 + 30, 5 + 11 + 31, 5 + 11 + 32, 5 + 11 + 33, 5 + 11 + 34, 5 + 11 + 35, 5 + 11 + 36, 5 + 11 + 37 |
| 12 | 5 + 12 + 13, 5 + 12 + 14, 5 + 12 + 15, 5 + 12 + 16, 5 + 12 + 17, 5 + 12 + 18, 5 + 12 + 19, 5 + 12 + 20, 5 + 12 + 21, 5 + 12 + 22, 5 + 12 + 23, 5 + 12 + 24, 5 + 12 + 25, 5 + 12 + 26, 5 + 12 + 27, 5 + 12 + 28, 5 + 12 + 29, 5 + 12 + 30, 5 + 12 + 31, 5 + 12 + 32, 5 + 12 + 33, 5 + 12 + 34, 5 + 12 + 35, 5 + 12 + 36, 5 + 12 + 37 |
| 13 | 5 + 13 + 14, 5 + 13 + 15, 5 + 13 + 16, 5 + 13 + 17, 5 + 13 + 18, 5 + 13 + 19, 5 + 13 + 20, 5 + 13 + 21, 5 + 13 + 22, 5 + 13 + 23, 5 + 13 + 24, 5 + 13 + 25, 5 + 13 + 26, 5 + 13 + 27, 5 + 13 + 28, 5 + 13 + 29, 5 + 13 + 30, 5 + 13 + 31, 5 + 13 + 32, 5 + 13 + 33, 5 + 13 + 34, 5 + 13 + 35, 5 + 13 + 36, 5 + 13 + 37 |
| 14 | 5 + 14 + 15, 5 + 14 + 16, 5 + 14 + 17, 5 + 14 + 18, 5 + 14 + 19, 5 + 14 + 20, 5 + 14 + 21, 5 + 14 + 22, 5 + 14 + 23, 5 + 14 + 24, 5 + 14 + 25, 5 + 14 + 26, 5 + 14 + 27, 5 + 14 + 28, 5 + 14 + 29, 5 + 14 + 30, 5 + 14 + 31, 5 + 14 + 32, 5 + 14 + 33, 5 + 14 + 34, 5 + 14 + 35, 5 + 14 + 36, 5 + 14 + 37 |

TABLE 6-continued

Delta-3-carene family of terpene formulations.

Table 6. Delta-3-carene family of terpene formulations. The numbers refer to the terpenes from Table 1. The designation "family" is only for convenience in presentation, as other tables also include formulations with delta-3-carene.

| Subfamily | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 15 | 5 + 15 + 16, 5 + 15 + 17, 5 + 15 + 18, 5 + 15 + 19, 5 + 15 + 20, 5 + 15 + 21, 5 + 15 + 22, 5 + 15 + 23, 5 + 15 + 24, 5 + 15 + 25, 5 + 15 + 26, 5 + 15 + 27, 5 + 15 + 28, 5 + 15 + 29, 5 + 15 + 30, 5 + 15 + 31, 5 + 15 + 32, 5 + 15 + 33, 5 + 15 + 34, 5 + 15 + 35, 5 + 15 + 36, 5 + 15 + 37 |
| 16 | 5 + 16 + 17, 5 + 16 + 18, 5 + 16 + 19, 5 + 16 + 20, 5 + 16 + 21, 5 + 16 + 22, 5 + 16 + 23, 5 + 16 + 24, 5 + 16 + 25, 5 + 16 + 26, 5 + 16 + 27, 5 + 16 + 28, 5 + 16 + 29, 5 + 16 + 30, 5 + 16 + 31, 5 + 16 + 32, 5 + 16 + 33, 5 + 16 + 34, 5 + 16 + 35, 5 + 16 + 36, 5 + 16 + 37 |
| 17 | 5 + 17 + 18, 5 + 17 + 19, 5 + 17 + 20, 5 + 17 + 20, 5 + 17 + 21, 5 + 17 + 22, 5 + 17 + 23, 5 + 17 + 24, 5 + 17 + 25, 5 + 17 + 26, 5 + 17 + 27, 5 + 17 + 28, 5 + 17 + 29, 5 + 17 + 30, 5 + 17 + 31, 5 + 17 + 32, 5 + 17 + 33, 5 + 17 + 34, 5 + 17 + 35, 5 + 17 + 36, 5 + 17 + 37 |
| 18 | 5 + 18 + 19, 5 + 18 + 20, 5 + 18 + 21, 5 + 18 + 22, 5 + 18 + 23, 5 + 18 + 24, 5 + 18 + 25, 5 + 18 + 26, 5 + 18 + 27, 5 + 18 + 28, 5 + 18 + 29, 5 + 18 + 30, 5 + 18 + 31, 5 + 18 + 32, 5 + 18 + 33, 5 + 18 + 34, 5 + 18 + 35, 5 + 18 + 36, 5 + 18 + 37 |
| 19 | 5 + 19 + 20, 5 + 19 + 21, 5 + 19 + 22, 5 + 19 + 23, 5 + 19 + 24, 5 + 19 + 25, 5 + 19 + 26, 5 + 19 + 27, 5 + 19 + 28, 5 + 19 + 29, 5 + 19 + 30, 5 + 19 + 31, 5 + 19 + 32, 5 + 19 + 33, 5 + 19 + 34, 5 + 19 + 35, 5 + 19 + 36, 5 + 19 + 37 |
| 20 | 5 + 20 + 21, 5 + 20 + 22, 5 + 20 + 23, 5 + 20 + 24, 5 + 20 + 25, 5 + 20 + 26, 5 + 20 + 27, 5 + 20 + 28, 5 + 20 + 29, 5 + 20 + 30, 5 + 20 + 31, 5 + 20 + 32, 5 + 20 + 33, 5 + 20 + 34, 5 + 20 + 35, 5 + 20 + 36, 5 + 20 + 37 |
| 21 | 5 + 21 + 22, 5 + 21 + 23, 5 + 21 + 24, 5 + 21 + 25, 5 + 21 + 26, 5 + 21 + 27, 5 + 21 + 28, 5 + 21 + 29, 5 + 21 + 30, 5 + 21 + 31, 5 + 21 + 32, 5 + 21 + 33, 5 + 21 + 34, 5 + 21 + 35, 5 + 21 + 36, 5 + 21 + 37 |
| 22 | 5 + 22 + 23, 5 + 22 + 24, 5 + 22 + 25, 5 + 22 + 26, 5 + 22 + 27, 5 + 22 + 28, 5 + 22 + 29, 5 + 22 + 30, 5 + 22 + 31, 5 + 22 + 32, 5 + 22 + 33, 5 + 22 + 34, 5 + 22 + 35, 5 + 22 + 36, 5 + 22 + 37 |
| 23 | 5 + 23 + 24, 5 + 23 + 25, 5 + 23 + 26, 5 + 23 + 27, 5 + 23 + 28, 5 + 23 + 29, 5 + 23 + 30, 5 + 23 + 31, 5 + 23 + 32, 5 + 23 + 33, 5 + 23 + 34, 5 + 23 + 35, 5 + 23 + 36, 5 + 23 + 37 |
| 24 | 5 + 24 + 25, 5 + 24 + 26, 5 + 24 + 27, 5 + 24 + 28, 5 + 24 + 28, 5 + 24 + 29, 5 + 24 + 30, 5 + 24 + 31, 5 + 24 + 32, 5 + 24 + 33, 5 + 24 + 34, 5 + 24 + 35, 5 + 24 + 36, 5 + 24 + 37 |
| 25 | 5 + 25 + 26, 5 + 25 + 27, 5 + 25 + 28, 5 + 25 + 29, 5 + 25 + 30, 5 + 25 + 31, 5 + 25 + 32, 5 + 25 + 33, 5 + 25 + 34, 5 + 25 + 35, 5 + 25 + 36, 5 + 25 + 37 |
| 26 | 5 + 26 + 27, 5 + 26 + 28, 5 + 26 + 29, 5 + 26 + 30, 5 + 26 + 31, 5 + 26 + 32, 5 + 26 + 33, 5 + 26 + 34, 5 + 26 + 35, 5 + 26 + 36, 5 + 26 + 37 |
| 27 | 5 + 27 + 28, 5 + 27 + 29, 5 + 27 + 30, 5 + 27 + 31, 5 + 27 + 32, 5 + 27 + 33, 5 + 27 + 34, 5 + 27 + 35, 5 + 27 + 36, 5 + 27 + 37 |
| 28 | 5 + 28 + 29, 5 + 28 + 30, 5 + 28 + 31, 5 + 28 + 32, 5 + 28 + 33, 5 + 28 + 34, 5 + 28 + 35, 5 + 28 + 36, 5 + 28 + 37 |
| 29 | 5 + 29 + 30, 5 + 29 + 31, 5 + 29 + 32, 5 + 29 + 33, 5 + 29 + 34, 5 + 29 + 35, 5 + 29 + 36, 5 + 29 + 37 |
| 30 | 5 + 30 + 31, 5 + 30 + 32, 5 + 30 + 33, 5 + 30 + 34, 5 + 30 + 35, 5 + 30 + 36, 5 + 30 + 37 |
| 31 | 5 + 31 + 32, 5 + 31 + 33, 5 + 31 + 34, 5 + 31 + 35, 5 + 31 + 36, 5 + 31 + 37 |
| 32 | 5 + 32 + 33, 5 + 32 + 34, 5 + 32 + 35, 5 + 32 + 36, 5 + 32 + 37 |
| 33 | 5 + 33 + 34, 5 + 33 + 35, 5 + 33 + 36, 5 + 33 + 37 |
| 34 | 5 + 34 + 35, 5 + 34 + 36, 5 + 34 + 37 |
| 35 | 5 + 35 + 36, 5 + 35 + 37 |
| 36 | 5 + 36 + 37 |

TABLE 7

Beta-caryophyllene family of terpene formulations.

Table 7. Beta-caryophyllene family of terpene formulations. The numbers refer to the terpenes from Table 1. The designation "family" is only for convenience in presentation, as other tables also include formulations with beta-caryophyllene.

Each disclosure of three terpenes represents a distinct formulation. In one embodiment, the formulation that is described by the indicated mixture of the three terpenes does not include any additional terpenes. In other embodiments, it does include additional terpenes

| Subfamily | |
|---|---|
| 7 | 6 + 7 + 8, 6 + 7 + 9, 6 + 7 + 10, 6 + 7 + 11, 6 + 7 + 12, 6 + 7 + 13, 6 + 7 + 14, 6 + 7 + 15, 6 + 7 + 16, 6 + 7 + 17, 6 + 7 + 18, 6 + 7 + 19, 6 + 7 + 20, 6 + 7 + 21, 6 + 7 + 22, 6 + 7 + 23, 6 + 7 + 24, 6 + 7 + 25, 6 + 7 + 26, 6 + 7 + 27, 6 + 7 + 28, 6 + 7 + 29, 6 + 7 + 30, 6 + 7 + 31, 6 + 7 + 32, 6 + 7 + 33, 6 + 7 + 34, 6 + 7 + 35, 6 + 7 + 36, 6 + 7 + 37 |
| 8 | 6 + 8 + 9, 6 + 8 + 10, 6 + 8 + 11, 6 + 8 + 12, 6 + 8 + 13, 6 + 8 + 14, 6 + 8 + 15, 6 + 8 + 16, 6 + 8 + 17, 6 + 8 + 18, 6 + 8 + 19, 6 + 8 + 20, 6 + 8 + 21, 6 + 8 + 22, 6 + 8 + 23, 6 + 8 + 24, 6 + 8 + 25, 6 + 8 + 26, 6 + 8 + 27, 6 + 8 + 28, 6 + 8 + 29, 6 + 8 + 30, 6 + 8 + 31, 6 + 8 + 32, 6 + 8 + 33, 6 + 8 + 34, 6 + 8 + 35, 6 + 8 + 36, 6 + 8 + 37 |
| 9 | 6 + 9 + 10, 6 + 9 + 11, 6 + 9 + 12, 6 + 9 + 13, 6 + 9 + 14, 6 + 9 + 15, 6 + 9 + 16, 6 + 9 + 17, 6 + 9 + 18, 6 + 9 + 19, 6 + 9 + 20, 6 + 9 + 21, 6 + 9 + 22, 6 + 9 + 23, 6 + 9 + 24, 6 + 9 + 25, 6 + 9 + 26, 6 + 9 + 27, 6 + 9 + 28, 6 + 9 + 29, 6 + 9 + 30, 6 + 9 + 31, 6 + 9 + 32, 6 + 9 + 33, 6 + 9 + 34, 6 + 9 + 35, 6 + 9 + 36, 6 + 9 + 37 |
| 10 | 6 + 10 + 11, 6 + 10 + 12, 6 + 10 + 13, 6 + 10 + 14, 6 + 10 + 15, 6 + 10 + 16, 6 + 10 + 17, 6 + 10 + 18, 6 + 10 + 19, 6 + 10 + 20, 6 + 10 + 21, 6 + 10 + 22, 6 + 10 + 23, 6 + 10 + 24, 6 + 10 + 25, 6 + 10 + 26, 6 + 10 + 27, 6 + 10 + 28, 6 + 10 + 29, 6 + 10 + 30, 6 + 10 + 31, 6 + 10 + 32, 6 + 10 + 33, 6 + 10 + 34, 6 + 10 + 35, 6 + 10 + 36, 6 + 10 + 37 |
| 11 | 6 + 11 + 12, 6 + 11 + 13, 6 + 11 + 14, 6 + 11 + 15, 6 + 11 + 16, 6 + 11 + 17, 6 + 11 + 18, 6 + 11 + 19, 6 + 11 + 20, 6 + 11 + 21, 6 + 11 + 22, 6 + 11 + 23, 6 + 11 + 24, 6 + 11 + 25, 6 + 11 + 26, 6 + 11 + 27, 6 + 11 + 28, 6 + 11 + 29, 6 + 11 + 30, 6 + 11 + 31, 6 + 11 + 32, 6 + 11 + 33, 6 + 11 + 34, 6 + 11 + 35, 6 + 11 + 36, 6 + 11 + 37 |
| 12 | 6 + 12 + 13, 6 + 12 + 14, 6 + 12 + 15, 6 + 12 + 16, 6 + 12 + 17, 6 + 12 + 18, 6 + 12 + 19, 6 + 12 + 20, 6 + 12 + 21, 6 + 12 + 22, 6 + 12 + 23, 6 + 12 + 24, 6 + 12 + 25, 6 + 12 + 26, 6 + 12 + 27, 6 + 12 + 28, 6 + 12 + 29, 6 + 12 + 30, 6 + 12 + 31, 6 + 12 + 32, 6 + 12 + 33, 6 + 12 + 34, 6 + 12 + 35, 6 + 12 + 36, 6 + 12 + 37 |
| 13 | 6 + 13 + 14, 6 + 13 + 15, 6 + 13 + 16, 6 + 13 + 17, 6 + 13 + 18, 6 + 13 + 19, 6 + 13 + 20, 6 + 13 + 21, 6 + 13 + 22, 6 + 13 + 23, 6 + 13 + 24, 6 + 13 + 25, 6 + 13 + 26, 6 + 13 + 27, 6 + 13 + 28, 6 + 13 + 29, 6 + 13 + 30, 6 + 13 + 31, 6 + 13 + 32, 6 + 13 + 33, 6 + 13 + 34, 6 + 13 + 35, 6 + 13 + 36, 6 + 13 + 37 |
| 14 | 6 + 14 + 15, 6 + 14 + 16, 6 + 14 + 17, 6 + 14 + 18, 6 + 14 + 19, 6 + 14 + 20, 6 + 14 + 21, 6 + 14 + 22, 6 + 14 + 23, 6 + 14 + 24, 6 + 14 + 25, 6 + 14 + 26, 6 + 14 + 27, 6 + 14 + 28, 6 + 14 + 29, 6 + 14 + 30, 6 + 14 + 31, 6 + 14 + 32, 6 + 14 + 33, 6 + 14 + 34, 6 + 14 + 35, 6 + 14 + 36, 6 + 14 + 37 |
| 15 | 6 + 15 + 16, 6 + 15 + 17, 6 + 15 + 18, 6 + 15 + 19, 6 + 15 + 20, 6 + 15 + 21, 6 + 15 + 22, 6 + 15 + 23, 6 + 15 + 24, 6 + 15 + 25, 6 + 15 + 26, 6 + 15 + 27, 6 + 15 + 28, 6 + 15 + 29, 6 + 15 + 30, 6 + 15 + 31, 6 + 15 + 32, 6 + 15 + 33, 6 + 15 + 34, 6 + 15 + 35, 6 + 15 + 36, 6 + 15 + 37 |
| 16 | 6 + 16 + 17, 6 + 16 + 18, 6 + 16 + 19, 6 + 16 + 20, 6 + 16 + 21, 6 + 16 + 22, 6 + 16 + 23, 6 + 16 + 24, 6 + 16 + 25, 6 + 16 + 26, 6 + 16 + 27, 6 + 16 + 28, 6 + 16 + 29, 6 + 16 + 30, 6 + 16 + 31, 6 + 16 + 32, 6 + 16 + 33, 6 + 16 + 34, 6 + 16 + 35, 6 + 16 + 36, 6 + 16 + 37 |
| 17 | 6 + 17 + 18, 6 + 17 + 19, 6 + 17 + 20, 6 + 17 + 21, 6 + 17 + 22, 6 + 17 + 23, 6 + 17 + 24, 6 + 17 + 25, 6 + 17 + 26, 6 + 17 + 27, 6 + 17 + 28, 6 + 17 + 29, 6 + 17 + 30, 6 + 17 + 31, 6 + 17 + 32, 6 + 17 + 33, 6 + 17 + 34, 6 + 17 + 35, 6 + 17 + 36, 6 + 17 + 37 |
| 18 | 6 + 18 + 19, 6 + 18 + 20, 6 + 18 + 21, 6 + 18 + 22, 6 + 18 + 23, 6 + 18 + 24, 6 + 18 + 25, 6 + 18 + 26, 6 + 18 + 27, 6 + 18 + 28, 6 + 18 + 29, 6 + 18 + 30, 6 + 18 + 31, 6 + 18 + 32, 6 + 18 + 33, 6 + 18 + 34, 6 + 18 + 35, 6 + 18 + 36, 6 + 18 + 37 |
| 19 | 6 + 19 + 20, 6 + 19 + 21, 6 + 19 + 22, 6 + 19 + 23, 6 + 19 + 24, 6 + 19 + 25, 6 + 19 + 26, 6 + 19 + 27, 6 + 19 + 28, 6 + 19 + 29, 6 + 19 + 30, 6 + 19 + 31, 6 + 19 + 32, 6 + 19 + 33, 6 + 19 + 34, 6 + 19 + 35, 6 + 19 + 36, 6 + 19 + 37 |
| 20 | 6 + 20 + 21, 6 + 20 + 22, 6 + 20 + 23, 6 + 20 + 24, 6 + 20 + 25, 6 + 20 + 26, 6 + 20 + 27, 6 + 20 + 28, 6 + 20 + 29, 6 + 20 + 30, 6 + 20 + 31, 6 + 20 + 32, 6 + 20 + 33, 6 + 20 + 34, 6 + 20 + 35, 6 + 20 + 36, 6 + 20 + 37 |
| 21 | 6 + 21 + 22, 6 + 21 + 23, 6 + 21 + 24, 6 + 21 + 25, 6 + 21 + 26, 6 + 21 + 27, 6 + 21 + 28, 6 + 21 + 29, 6 + 21 + 30, 6 + 21 + 31, 6 + 21 + 32, 6 + 21 + 33, 6 + 21 + 34, 6 + 21 + 35, 6 + 21 + 36, 6 + 21 + 37 |
| 22 | 6 + 22 + 23, 6 + 22 + 24, 6 + 22 + 25, 6 + 22 + 26, 6 + 22 + 27, 6 + 22 + 28, 6 + 22 + 29, 6 + 22 + 30, 6 + 22 + 31, 6 + 22 + 32, 6 + 22 + 33, 6 + 22 + 34, 6 + 22 + 35, 6 + 22 + 36, 6 + 22 + 37 |

TABLE 7-continued

Beta-caryophyllene family of terpene formulations.

Table 7. Beta-caryophyllene family of terpene formulations. The numbers refer to the terpenes from Table 1. The designation "family" is only for convenience in presentation, as other tables also include formulations with beta-caryophyllene.

Each disclosure of three terpenes represents a distinct formulation. In one embodiment, the formulation that is described by the indicated mixture of the three terpenes does not include any additional terpenes. In other embodiments, it does include additional terpenes

| Subfamily | |
|---|---|
| 23 | 6 + 23 + 24, 6 + 23 + 25, 6 + 23 + 26, 6 + 23 + 27, 6 + 23 + 28, 6 + 23 + 29, 6 + 23 + 30, 6 + 23 + 31, 6 + 23 + 32, 6 + 23 + 33, 6 + 23 + 34, 6 + 23 + 35, 6 + 23 + 36, 6 + 23 + 37 |
| 24 | 6 + 24 + 25, 6 + 24 + 26, 6 + 24 + 27, 6 + 24 + 28, 6 + 24 + 29, 6 + 24 + 30, 6 + 24 + 31, 6 + 24 + 32, 6 + 24 + 33, 6 + 24 + 34, 6 + 24 + 35, 6 + 24 + 36, 6 + 24 + 37 |
| 25 | 6 + 25 + 26, 6 + 25 + 27, 6 + 25 + 28, 6 + 25 + 29, 6 + 25 + 30, 6 + 25 + 31, 6 + 25 + 32, 6 + 25 + 33, 6 + 25 + 34, 6 + 25 + 35, 6 + 25 + 36, 6 + 25 + 37 |
| 26 | 6 + 26 + 27, 6 + 26 + 28, 6 + 26 + 29, 6 + 26 + 30, 6 + 26 + 31, 6 + 26 + 32, 6 + 26 + 33, 6 + 26 + 34, 6 + 26 + 35, 6 + 26 + 36, 6 + 26 + 37 |
| 27 | 6 + 27 + 28, 6 + 27 + 29, 6 + 27 + 30, 6 + 27 + 31, 6 + 27 + 32, 6 + 27 + 33, 6 + 27 + 34, 6 + 27 + 35, 6 + 27 + 36, 6 + 27 + 37 |
| 28 | 6 + 28 + 29, 6 + 28 + 30, 6 + 28 + 31, 6 + 28 + 32, 6 + 28 + 33, 6 + 28 + 34, 6 + 28 + 35, 6 + 28 + 36, 6 + 28 + 37 |
| 29 | 6 + 29 + 30, 6 + 29 + 31, 6 + 29 + 32, 6 + 29 + 33, 6 + 29 + 34, 6 + 29 + 35, 6 + 29 + 36, 6 + 29 + 37 |
| 30 | 6 + 30 + 31, 6 + 30 + 32, 6 + 30 + 33, 6 + 30 + 34, 6 + 30 + 35, 6 + 30 + 36, 6 + 30 + 37 |
| 31 | 6 + 31 + 32, 6 + 31 + 33, 6 + 31 + 34, 6 + 31 + 35, 6 + 31 + 36, 6 + 31 + 37 |
| 32 | 6 + 32 + 33, 6 + 32 + 34, 6 + 32 + 35, 6 + 32 + 36, 6 + 32 + 37 |
| 33 | 6 + 33 + 34, 6 + 33 + 35, 6 + 33 + 36, 6 + 33 + 37 |
| 34 | 6 + 34 + 35, 6 + 34 + 36, 6 + 34 + 37 |
| 35 | 6 + 35 + 36, 6 + 35 + 37 |
| 36 | 6 + 36 + 37 |

TABLE 8

Alpha-Cedrene family of terpene formulations.
Table 8. Alpha-Cedrene family of terpene formulations. The numbers refer to the terpenes from Table 1. The designation "family" is only for convenience in presentation, as other tables also include formulations with alpha-Cedrene.

Each disclosure of three terpenes represents a distinct formulation. In one embodiment, the formulation that is described by the indicated mixture of the three terpenes does not include any additional terpenes. In other embodiments, it does include additional terpenes.

| Subfamily | |
|---|---|
| 9 | 8 + 9 + 10, 8 + 9 + 11, 8 + 9 + 12, 8 + 9 + 13, 8 + 9 + 14, 8 + 9 + 15, 8 + 9 + 16, 8 + 9 + 17, 8 + 9 + 18, 8 + 9 + 19, 8 + 9 + 20, 8 + 9 + 21, 8 + 9 + 22, 8 + 9 + 23, 8 + 9 + 24, 8 + 9 + 25, 8 + 9 + 26, 8 + 9 + 27, 8 + 9 + 28, 8 + 9 + 29, 8 + 9 + 30, 8 + 9 + 31, 8 + 9 + 32, 8 + 9 + 33, 8 + 9 + 34, 8 + 9 + 35, 8 + 9 + 36, 8 + 9 + 37 |
| 10 | 8 + 10 + 11, 8 + 10 + 12, 8 + 10 + 13, 8 + 10 + 14, 8 + 10 + 15, 8 + 10 + 16, 8 + 10 + 17, 8 + 10 + 18, 8 + 10 + 19, 8 + 10 + 20, 8 + 10 + 21, 8 + 10 + 22, 8 + 10 + 23, 8 + 10 + 24, 8 + 10 + 25, 8 + 10 + 26, 8 + 10 + 27, 8 + 10 + 28, 8 + 10 + 29, 8 + 10 + 30, 8 + 10 + 31, 8 + 10 + 32, 8 + 10 + 33, 8 + 10 + 34, 8 + 10 + 35, 8 + 10 + 36, 8 + 10 + 37 |
| 11 | 8 + 11 + 12, 8 + 11 + 13, 8 + 11 + 14, 8 + 11 + 15, 8 + 11 + 16, 8 + 11 + 17, 8 + 11 + 18, 8 + 11 + 19, 8 + 11 + 20, 8 + 11 + 21, 8 + 11 + 22, 8 + 11 + 23, 8 + 11 + 24, 8 + 11 + 25, 8 + 11 + 26, 8 + 11 + 27, 8 + 11 + 28, 8 + 11 + 29, 8 + 11 + 30, 8 + 11 + 31, 8 + 11 + 32, 8 + 11 + 33, 8 + 11 + 34, 8 + 11 + 35, 8 + 11 + 36, 8 + 11 + 37 |
| 12 | 8 + 12 + 13, 8 + 12 + 14, 8 + 12 + 15, 8 + 12 + 16, 8 + 12 + 17, 8 + 12 + 18, 8 + 12 + 19, 8 + 12 + 20, 8 + 12 + 21, 8 + 12 + 22, 8 + 12 + 23, 8 + 12 + 24, 8 + 12 + 25, 8 + 12 + 26, 8 + 12 + 27, 8 + 12 + 28, 8 + 12 + 29, 8 + 12 + 30, 8 + 12 + 31, 8 + 12 + 32, 8 + 12 + 33, 8 + 12 + 34, 8 + 12 + 35, 8 + 12 + 36, 8 + 12 + 37 |
| 13 | 8 + 13 + 14, 8 + 13 + 15, 8 + 13 + 16, 8 + 13 + 17, 8 + 13 + 18, 8 + 13 + 19, 8 + 13 + 20, 8 + 13 + 21, 8 + 13 + 22, 8 + 13 + 23, 8 + 13 + 24, 8 + 13 + 25, 8 + 13 + 26, 8 + 13 + 27, 8 + 13 + 28, 8 + 13 + 29, 8 + 13 + 30, 8 + 13 + 31, 8 + 13 + 32, 8 + 13 + 33, 8 + 13 + 34, 8 + 13 + 35, 8 + 13 + 36, 8 + 13 + 37 |
| 14 | 8 + 14 + 15, 8 + 14 + 16, 8 + 14 + 17, 8 + 14 + 18, 8 + 14 + 19, 8 + 14 + 20, 8 + 14 + 21, 8 + 14 + 22, 8 + 14 + 23, 8 + 14 + 24, 8 + 14 + 25, 8 + 14 + 26, 8 + 14 + 27, 8 + 14 + 28, 8 + 14 + 29, 8 + 14 + 30, 8 + 14 + 31, 8 + 14 + 32, 8 + 14 + 33, 8 + 14 + 34, 8 + 14 + 35, 8 + 14 + 36, 8 + 14 + 37 |
| 15 | 8 + 15 + 16, 8 + 15 + 17, 8 + 15 + 18, 8 + 15 + 19, 8 + 15 + 20, 8 + 15 + 21, 8 + 15 + 22, 8 + 15 + 23, 8 + 15 + 24, 8 + 15 + 25, 8 + 15 + 26, 8 + 15 + 27, 8 + 15 + 28, 8 + 15 + 29, 8 + 15 + 30, 8 + 15 + 31, 8 + 15 + 32, 8 + 15 + 33, 8 + 15 + 34, 8 + 15 + 35, 8 + 15 + 36, 8 + 15 + 37 |
| 16 | 8 + 16 + 17, 8 + 16 + 18, 8 + 16 + 19, 8 + 16 + 20, 8 + 16 + 21, 8 + 16 + 22, 8 + 16 + 23, 8 + 16 + 24, 8 + 16 + 25, 8 + 16 + 26, 8 + 16 + 27, 8 + 16 + 28, 8 + 16 + 29, 8 + 16 + 30, 8 + 16 + 31, 8 + 16 + 32, 8 + 16 + 33, 8 + 16 + 34, 8 + 16 + 35, 8 + 16 + 36, 8 + 16 + 37 |

TABLE 8-continued

Alpha-Cedrene family of terpene formulations.
Table 8. Alpha-Cedrene family of terpene formulations. The numbers refer to the terpenes from Table 1. The designation "family" is only for convenience in presentation, as other tables also include formulations with alpha-Cedrene.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 17 | 8 + 17 + 18, 8 + 17 + 19, 8 + 17 + 20, 8 + 17 + 21, 8 + 17 + 22, 8 + 17 + 23, 8 + 17 + 24, 8 + 17 + 25, 8 + 17 + 26, 8 + 17 + 27, 8 + 17 + 28, 8 + 17 + 29, 8 + 17 + 30, 8 + 17 + 31, 8 + 17 + 32, 8 + 17 + 33, 8 + 17 + 34, 8 + 17 + 35, 8 + 17 + 36, 8 + 17 + 37 |
| 18 | 8 + 18 + 19, 8 + 18 + 20, 8 + 18 + 21, 8 + 18 + 22, 8 + 18 + 23, 8 + 18 + 24, 8 + 18 + 25, 8 + 18 + 26, 8 + 18 + 27, 8 + 18 + 28, 8 + 18 + 29, 8 + 18 + 30, 8 + 18 + 31, 8 + 18 + 32, 8 + 18 + 33, 8 + 18 + 34, 8 + 18 + 35, 8 + 18 + 36, 8 + 18 + 37 |
| 19 | 8 + 19 + 20, 8 + 19 + 21, 8 + 19 + 22, 8 + 19 + 23, 8 + 19 + 24, 8 + 19 + 25, 8 + 19 + 26, 8 + 19 + 27, 8 + 19 + 28, 8 + 19 + 29, 8 + 19 + 30, 8 + 19 + 31, 8 + 19 + 32, 8 + 19 + 33, 8 + 19 + 34, 8 + 19 + 35, 8 + 19 + 36, 8 + 19 + 37 |
| 20 | 8 + 20 + 21, 8 + 20 + 22, 8 + 20 + 23, 8 + 20 + 24, 8 + 20 + 25, 8 + 20 + 26, 8 + 20 + 27, 8 + 20 + 28, 8 + 20 + 29, 8 + 20 + 30, 8 + 20 + 31, 8 + 20 + 32, 8 + 20 + 33, 8 + 20 + 34, 8 + 20 + 35, 8 + 20 + 36, 8 + 20 + 37 |
| 21 | 8 + 21 + 22, 8 + 21 + 23, 8 + 21 + 24, 8 + 21 + 25, 8 + 21 + 26, 8 + 21 + 27, 8 + 21 + 28, 8 + 21 + 29, 8 + 21 + 30, 8 + 21 + 31, 8 + 21 + 32, 8 + 21 + 33, 8 + 21 + 34, 8 + 21 + 35, 8 + 21 + 36, 8 + 21 + 37 |
| 22 | 8 + 22 + 23, 8 + 22 + 24, 8 + 22 + 25, 8 + 22 + 26, 8 + 22 + 27, 8 + 22 + 28, 8 + 22 + 29, 8 + 22 + 30, 8 + 22 + 31, 8 + 22 + 32, 8 + 22 + 33, 8 + 22 + 34, 8 + 22 + 35, 8 + 22 + 36, 8 + 22 + 37 |
| 23 | 8 + 23 + 24, 8 + 23 + 25, 8 + 23 + 26, 8 + 23 + 27, 8 + 23 + 28, 8 + 23 + 29, 8 + 23 + 30, 8 + 23 + 31, 8 + 23 + 32, 8 + 23 + 33, 8 + 23 + 34, 8 + 23 + 35, 8 + 23 + 36, 8 + 23 + 37 |
| 24 | 8 + 24 + 25, 8 + 24 + 26, 8 + 24 + 27, 8 + 24 + 28, 8 + 24 + 29, 8 + 24 + 30, 8 + 24 + 31, 8 + 24 + 32, 8 + 24 + 33, 8 + 24 + 34, 8 + 24 + 35, 8 + 24 + 36, 8 + 24 + 37 |
| 25 | 8 + 25 + 26, 8 + 25 + 27, 8 + 25 + 28, 8 + 25 + 29, 8 + 25 + 30, 8 + 25 + 31, 8 + 25 + 32, 8 + 25 + 33, 8 + 25 + 34, 8 + 25 + 35, 8 + 25 + 36, 8 + 25 + 37 |
| 26 | 8 + 26 + 27, 8 + 26 + 28, 8 + 26 + 29, 8 + 26 + 30, 8 + 26 + 31, 8 + 26 + 32, 8 + 26 + 33, 8 + 26 + 34, 8 + 26 + 35, 8 + 26 + 36, 8 + 26 + 37 |
| 27 | 8 + 27 + 28, 8 + 27 + 29, 8 + 27 + 30, 8 + 27 + 31, 8 + 27 + 32, 8 + 27 + 33, 8 + 27 + 34, 8 + 27 + 35, 8 + 27 + 36, 8 + 27 + 37 |
| 28 | 8 + 28 + 29, 8 + 28 + 30, 8 + 28 + 31, 8 + 28 + 32, 8 + 28 + 33, 8 + 28 + 34, 8 + 28 + 35, 8 + 28 + 36, 8 + 28 + 37 |
| 29 | 8 + 29 + 30, 8 + 29 + 31, 8 + 29 + 32, 8 + 29 + 33, 8 + 29 + 34, 8 + 29 + 35, 8 + 29 + 36, 8 + 29 + 37 |
| 30 | 8 + 30 + 31, 8 + 30 + 32, 8 + 30 + 33, 8 + 30 + 34, 8 + 30 + 35, 8 + 30 + 36, 8 + 30 + 37 |
| 31 | 8 + 31 + 32, 8 + 31 + 33, 8 + 31 + 34, 8 + 31 + 35, 8 + 31 + 36, 8 + 31 + 37 |
| 32 | 8 + 32 + 33, 8 + 32 + 34, 8 + 32 + 35, 8 + 32 + 36, 8 + 32 + 37 |
| 33 | 8 + 33 + 34, 8 + 33 + 35, 8 + 33 + 36, 8 + 33 + 37 |
| 34 | 8 + 34 + 35, 8 + 34 + 36, 8 + 34 + 37 |
| 35 | 8 + 35 + 36, 8 + 35 + 37 |
| 36 | 8 + 36 + 37 |

TABLE 9

Beta-eudesmol family of terpene formulations.
Table 9. Beta-eudesmol family of terpene formulations. The numbers refer to the terpenes from Table 1. The designation "family" is only for convenience in presentation, as other tables also include formulations with beta-eudesmol.

| Sub-family | Each disclosure of three terpenes represents a distinct formulation. In one embodiment, the formulation that is described by the indicated mixture of the three terpenes does not include any addition terpenes. In other embodiments, it does include additional terpenes. |
|---|---|
| 10 | 9 + 10 + 11; 9 + 10 + 12; 9 + 10 + 13; 9 + 10 + 14; 9 + 10 + 15; 9 + 10 + 16; 9 + 10 + 17; 9 + 10 + 18; 9 + 10 + 19; 9 + 10 + 20; 9 + 10 + 21; 9 + 10 + 22; 9 + 10 + 23; 9 + 10 + 24; 9 + 10 + 25; 9 + 10 + 26; 9 + 10 + 27; 9 + 10 + 28; 9 + 10 + 29; 9 + 10 + 30; 9 + 10 + 31; 9 + 10 + 32; 9 + 10 + 33; 9 + 10 + 34; 9 + 10 + 35; 9 + 10 + 36; 9 + 10 + 37 |
| 11 | 9 + 11 + 12; 9 + 11 + 13; 9 + 11 + 14; 9 + 11 + 15; 9 + 11 + 16; 9 + 11 + 17; 9 + 11 + 18; 9 + 11 + 19; 9 + 11 + 20; 9 + 11 + 21; 9 + 11 + 22; 9 + 11 + 23; 9 + 11 + 24; 9 + 11 + 25; 9 + 11 + 26; 9 + 11 + 27; 9 + 11 + 28; 9 + 11 + 29; 9 + 11 + 30; 9 + 11 + 31; 9 + 11 + 32; 9 + 11 + 33; 9 + 11 + 34; 9 + 11 + 35; 9 + 11 + 36; 9 + 11 + 37 |
| 12 | 9 + 12 + 13; 9 + 12 + 14; 9 + 12 + 15; 9 + 12 + 16; 9 + 12 + 17; 9 + 12 + 18; 9 + 12 + 19; 9 + 12 + 20; 9 + 12 + 21; 9 + 12 + 22; 9 + 12 + 23; 9 + 12 + 24; 9 + 12 + 25; 9 + 12 + 26; 9 + 12 + 27; 9 + 12 + 28; 9 + 12 + 29; 9 + 12 + 30; 9 + 12 + 31; 9 + 12 + 32; 9 + 12 + 33; 9 + 12 + 34; 9 + 12 + 35; 9 + 12 + 36; 9 + 12 + 37 |
| 13 | 9 + 13 + 14; 9 + 13 + 15; 9 + 13 + 16; 9 + 13 + 17; 9 + 13 + 18; 9 + 13 + 19; 9 + 13 + 20; 9 + 13 + 21; 9 + 13 + 22; 9 + 13 + 23; 9 + 13 + 24; 9 + 13 + 25; 9 + 13 + 26; 9 + 13 + 27; 9 + 13 + 28; 9 + 13 + 29; 9 + 13 + 30; 9 + 13 + 31; 9 + 13 + 32; 9 + 13 + 33; 9 + 13 + 34; 9 + 13 + 35; 9 + 13 + 36; 9 + 13 + 37 |
| 14 | 9 + 14 + 15; 9 + 14 + 16; 9 + 14 + 17; 9 + 14 + 18; 9 + 14 + 19; 9 + 14 + 20; 9 + 14 + 21; 9 + 14 + 22; 9 + 14 + 23; 9 + 14 + 24; 9 + 14 + 25; 9 + 14 + 26; 9 + 14 + 27; 9 + 14 + 28; 9 + 14 + 29; 9 + 14 + 30; 9 + 14 + 31; 9 + 14 + 32; 9 + 14 + 33; 9 + 14 + 34; 9 + 14 + 35; 9 + 14 + 36; 9 + 14 + 37 |
| 15 | 9 + 15 + 16; 9 + 15 + 17; 9 + 15 + 18; 9 + 15 + 19; 9 + 15 + 20; 9 + 15 + 21; 9 + 15 + 22; 9 + 15 + 23; 9 + 15 + 24; 9 + 15 + 25; 9 + 15 + 26; 9 + 15 + 27; 9 + 15 + 28; 9 + 15 + 29; 9 + 15 + 30; 9 + 15 + 31; 9 + 15 + 32; 9 + 15 + 33; 9 + 15 + 34; 9 + 15 + 35; 9 + 15 + 36; 9 + 15 + 37 |
| 16 | 9 + 16 + 17; 9 + 16 + 18; 9 + 16 + 19; 9 + 16 + 20; 9 + 16 + 21; 9 + 16 + 22; 9 + 16 + 23; 9 + 16 + 24; 9 + 16 + 25; 9 + 16 + 26; 9 + 16 + 27; 9 + 16 + 28; 9 + 16 + 29; 9 + 16 + 30; 9 + 16 + 31; 9 + 16 + 32; 9 + 16 + 33; 9 + 16 + 34; 9 + 16 + 35; 9 + 16 + 36; 9 + 16 + 37 |
| 17 | 9 + 17 + 18; 9 + 17 + 19; 9 + 17 + 20; 9 + 17 + 21; 9 + 17 + 22; 9 + 17 + 23; 9 + 17 + 24; 9 + 17 + 25; 9 + 17 + 26; 9 + 17 + 27; 9 + 17 + 28; 9 + 17 + 29; 9 + 17 + 30; 9 + 17 + 31; 9 + 17 + 32; 9 + 17 + 33; 9 + 17 + 34; 9 + 17 + 35; 9 + 17 + 36; 9 + 17 + 37 |
| 18 | 9 + 18 + 19; 9 + 18 + 20; 9 + 18 + 21; 9 + 18 + 22; 9 + 18 + 23; 9 + 18 + 24; 9 + 18 + 25; 9 + 18 + 26; 9 + 18 + 27; 9 + 18 + 28; 9 + 18 + 29; 9 + 18 + 30; 9 + 18 + 31; 9 + 18 + 32; 9 + 18 + 33; 9 + 18 + 34; 9 + 18 + 35; 9 + 18 + 36; 9 + 18 + 37 |
| 19 | 9 + 19 + 20; 9 + 19 + 21; 9 + 19 + 22; 9 + 19 + 23; 9 + 19 + 24; 9 + 19 + 25; 9 + 19 + 26; 9 + 19 + 27; 9 + 19 + 28; 9 + 19 + 29; 9 + 19 + 30; 9 + 19 + 31; 9 + 19 + 32; 9 + 19 + 33; 9 + 19 + 34; 9 + 19 + 35; 9 + 19 + 36; 9 + 19 + 37 |
| 20 | 9 + 20 + 21; 9 + 20 + 22; 9 + 20 + 23; 9 + 20 + 24; 9 + 20 + 25; 9 + 20 + 26; 9 + 20 + 27; 9 + 20 + 28; 9 + 20 + 29; 9 + 20 + 30; 9 + 20 + 31; 9 + 20 + 32; 9 + 20 + 33; 9 + 20 + 34; 9 + 20 + 35; 9 + 20 + 36; 9 + 20 + 37 |
| 21 | 9 + 21 + 22; 9 + 21 + 23; 9 + 21 + 24; 9 + 21 + 25; 9 + 21 + 26; 9 + 21 + 27; 9 + 21 + 28; 9 + 21 + 29; 9 + 21 + 30; 9 + 21 + 31; 9 + 21 + 32; 9 + 21 + 33; 9 + 21 + 34; 9 + 21 + 35; 9 + 21 + 36; 9 + 21 + 37 |
| 22 | 9 + 22 + 23; 9 + 22 + 24; 9 + 22 + 25; 9 + 22 + 26; 9 + 22 + 27; 9 + 22 + 28; 9 + 22 + 29; 9 + 22 + 30; 9 + 22 + 31; 9 + 22 + 32; 9 + 22 + 33; 9 + 22 + 34; 9 + 22 + 35; 9 + 22 + 36; 9 + 22 + 37 |

TABLE 9-continued

Beta-eudesmol family of terpene formulations.
Table 9. Beta-eudesmol family of terpene formulations. The numbers refer to the terpenes from Table 1. The designation "family" is only for convenience in presentation, as other tables also include formulations with beta-eudesmol.

| Sub-family | Each disclosure of three terpenes represents a distinct formulation. In one embodiment, the formulation that is described by the indicated mixture of the three terpenes does not include any addition terpenes. In other embodiments, it does include additional terpenes. |
|---|---|
| 23 | 9 + 23 + 24; 9 + 23 + 25; 9 + 23 + 26; 9 + 23 + 27; 9 + 23 + 28; 9 + 23 + 29; 9 + 23 + 30; 9 + 23 + 31; 9 + 23 + 32; 9 + 23 + 33; 9 + 23 + 34; 9 + 23 + 35; 9 + 23 + 36; 9 + 23 + 37 |
| 24 | 9 + 24 + 25; 9 + 24 + 26; 9 + 24 + 27; 9 + 24 + 28; 9 + 24 + 29; 9 + 24 + 30; 9 + 24 + 31; 9 + 24 + 32; 9 + 24 + 33; 9 + 24 + 34; 9 + 24 + 35; 9 + 24 + 36; 9 + 24 + 37 |
| 25 | 9 + 25 + 26; 9 + 25 + 27; 9 + 25 + 28; 9 + 25 + 29; 9 + 25 + 30; 9 + 25 + 31; 9 + 25 + 32; 9 + 25 + 33; 9 + 25 + 34; 9 + 25 + 35; 9 + 25 + 36; 9 + 25 + 37 |
| 26 | 9 + 26 + 27; 9 + 26 + 28; 9 + 26 + 29; 9 + 26 + 30; 9 + 26 + 31; 9 + 26 + 32; 9 + 26 + 33; 9 + 26 + 34; 9 + 26 + 35; 9 + 26 + 36; 9 + 26 + 37 |
| 27 | 9 + 27 + 28; 9 + 27 + 29; 9 + 27 + 30; 9 + 27 + 31; 9 + 27 + 32; 9 + 27 + 33; 9 + 27 + 34; 9 + 27 + 35; 9 + 27 + 36; 9 + 27 + 37 |
| 28 | 9 + 28 + 29; 9 + 28 + 30; 9 + 28 + 31; 9 + 28 + 32; 9 + 28 + 33; 9 + 28 + 34; 9 + 28 + 35; 9 + 28 + 36; 9 + 28 + 37 |
| 29 | 9 + 29 + 30; 9 + 29 + 31; 9 + 29 + 32; 9 + 29 + 33; 9 + 29 + 34; 9 + 29 + 35; 9 + 29 + 36; 9 + 29 + 37 |
| 30 | 9 + 30 + 31; 9 + 30 + 32; 9 + 30 + 33; 9 + 30 + 34; 9 + 30 + 35; 9 + 30 + 36; 9 + 30 + 37 |
| 31 | 9 + 31 + 32; 9 + 31 + 33; 9 + 31 + 34; 9 + 31 + 35; 9 + 31 + 36; 9 + 31 + 37 |
| 32 | 9 + 32 + 33; 9 + 32 + 34; 9 + 32 + 35; 9 + 32 + 36; 9 + 32 + 37 |
| 33 | 9 + 33 + 34; 9 + 33 + 35; 9 + 33 + 36; 9 + 33 + 37 |
| 34 | 9 + 34 + 35; 9 + 34 + 36; 9 + 34 + 37 |
| 35 | 9 + 35 + 36; 9 + 35 + 37 |
| 36 | 9 + 36 + 37 |

TABLE 10

(+)Fenchol family of terpene formulations.
Table 10. (+)Fenchol family of terpene formulations. The numbers refer to the terpenes from Table 1. The designation "family" is only for convenience in presentation, as other tables also include formulations with (+)fenchol.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 11 | 10 + 11 + 12; 10 + 11 + 13; 10 + 11 + 14; 10 + 11 + 15; 10 + 11 + 16; 10 + 11 + 17; 10 + 11 + 18; 10 + 11 + 20; 10 + 11 + 21; 10 + 11 + 22; 10 + 11 + 23; 10 + 11 + 24; 10 + 11 + 25; 10 + 11 + 26; 10 + 11 + 27; 10 + 11 + 28; 10 + 11 + 29; 10 + 11 + 30; 10 + 11 + 31; 10 + 11 + 32; 10 + 11 + 33; 10 + 11 + 34; 10 + 11 + 35; 10 + 11 + 36; 10 + 11 + 37 |
| 12 | 10 + 12 + 13; 10 + 12 + 14; 10 + 12 + 15; 10 + 12 + 16; 10 + 12 + 17; 10 + 12 + 18; 10 + 12 + 19; 10 + 12 + 20; 10 + 12 + 21; 10 + 12 + 22; 10 + 12 + 23; 10 + 12 + 24; 10 + 12 + 25; 10 + 12 + 26; 10 + 12 + 27; 10 + 12 + 28; 10 + 12 + 29; 10 + 12 + 30; 10 + 12 + 31; 10 + 12 + 32; 10 + 12 + 33; 10 + 12 + 34; 10 + 12 + 35; 10 + 12 + 36; 10 + 12 + 37 |
| 13 | 10 + 13 + 14; 10 + 13 + 15; 10 + 13 + 16; 10 + 13 + 17; 10 + 13 + 18; 10 + 13 + 19; 10 + 13 + 20; 10 + 13 + 21; 10 + 13 + 22; 10 + 13 + 23; 10 + 13 + 24; 10 + 13 + 25; 10 + 13 + 26; 10 + 13 + 27; 10 + 13 + 28; 10 + 13 + 29; 10 + 13 + 30; 10 + 13 + 31; 10 + 13 + 32; 10 + 13 + 33; 10 + 13 + 34; 10 + 13 + 35; 10 + 13 + 36; 10 + 13 + 37 |
| 14 | 10 + 14 + 15; 10 + 14 + 16; 10 + 14 + 17; 10 + 14 + 18; 10 + 14 + 19; 10 + 14 + 20; 10 + 14 + 21; 10 + 14 + 22; 10 + 14 + 23; 10 + 14 + 24; 10 + 14 + 25; 10 + 14 + 26; 10 + 14 + 27; 10 + 14 + 28; 10 + 14 + 29; 10 + 14 + 30; 10 + 14 + 31; 10 + 14 + 32; 10 + 14 + 33; 10 + 14 + 34; 10 + 14 + 35; 10 + 14 + 36; 10 + 14 + 37 |
| 15 | 10 + 15 + 16; 10 + 15 + 17; 10 + 15 + 18; 10 + 15 + 19; 10 + 15 + 20; 10 + 15 + 21; 10 + 15 + 22; 10 + 15 + 23; 10 + 15 + 24; 10 + 15 + 25; 10 + 15 + 26; 10 + 15 + 27; 10 + 15 + 28; 10 + 15 + 29; 10 + 15 + 30; 10 + 15 + 31; 10 + 15 + 32; 10 + 15 + 33; 10 + 15 + 34; 10 + 15 + 35; 10 + 15 + 36; 10 + 15 + 37 |
| 16 | 10 + 16 + 17; 10 + 16 + 18; 10 + 16 + 19; 10 + 16 + 20; 10 + 16 + 21; 10 + 16 + 22; 10 + 16 + 23; 10 + 16 + 24; 10 + 16 + 25; 10 + 16 + 26; 10 + 16 + 27; 10 + 16 + 28; 10 + 16 + 29; 10 + 16 + 30; 10 + 16 + 31; 10 + 16 + 32; 10 + 16 + 33; 10 + 16 + 34; 10 + 16 + 35; 10 + 16 + 36; 10 + 16 + 37 |
| 17 | 10 + 17 + 18; 10 + 17 + 19; 10 + 17 + 20; 10 + 17 + 21; 10 + 17 + 22; 10 + 17 + 23; 10 + 17 + 24; 10 + 17 + 25; 10 + 17 + 26; 10 + 17 + 27; 10 + 17 + 28; 10 + 17 + 29; 10 + 17 + 30; 10 + 17 + 31; 10 + 17 + 32; 10 + 17 + 33; 10 + 17 + 34; 10 + 17 + 35; 10 + 17 + 36; 10 + 17 + 37 |
| 18 | 10 + 18 + 19; 10 + 18 + 20; 10 + 18 + 21; 10 + 18 + 22; 10 + 18 + 23; 10 + 18 + 24; 10 + 18 + 25; 10 + 18 + 26; 10 + 18 + 27; 10 + 18 + 28; 10 + 18 + 29; 10 + 18 + 30; 10 + 18 + 31; 10 + 18 + 32; 10 + 18 + 33; 10 + 18 + 34; 10 + 18 + 35; 10 + 18 + 36; 10 + 18 + 37 |
| 19 | 10 + 19 + 20; 10 + 19 + 21; 10 + 19 + 22; 10 + 19 + 23; 10 + 19 + 24; 10 + 19 + 25; 10 + 19 + 26; 10 + 19 + 27; 10 + 19 + 28; 10 + 19 + 29; 10 + 19 + 30; 10 + 19 + 31; 10 + 19 + 32; 10 + 19 + 33; 10 + 19 + 34; 10 + 19 + 35; 10 + 19 + 36; 10 + 19 + 37 |
| 20 | 10 + 20 + 21; 10 + 20 + 22; 10 + 20 + 23; 10 + 20 + 24; 10 + 20 + 25; 10 + 20 + 26; 10 + 20 + 27; 10 + 20 + 28; 10 + 20 + 29; 10 + 20 + 30; 10 + 20 + 31; 10 + 20 + 32; 10 + 20 + 33; 10 + 20 + 34; 10 + 20 + 35; 10 + 20 + 36; 10 + 20 + 37 |
| 21 | 10 + 21 + 22; 10 + 21 + 23; 10 + 21 + 24; 10 + 21 + 25; 10 + 21 + 26; 10 + 21 + 27; 10 + 21 + 28; 10 + 21 + 29; 10 + 21 + 30; 10 + 21 + 31; 10 + 21 + 32; 10 + 21 + 33; 10 + 21 + 34; 10 + 21 + 35; 10 + 21 + 36; 10 + 21 + 37 |
| 22 | 10 + 22 + 23; 10 + 22 + 24; 10 + 22 + 25; 10 + 22 + 26; 10 + 22 + 27; 10 + 22 + 28; 10 + 22 + 29; 10 + 22 + 30; 10 + 22 + 31; 10 + 22 + 32; 10 + 22 + 33; 10 + 22 + 34; 10 + 22 + 35; 10 + 22 + 36; 10 + 22 + 37 |
| 23 | 10 + 23 + 24; 10 + 23 + 25; 10 + 23 + 26; 10 + 23 + 27; 10 + 23 + 28; 10 + 23 + 29; 10 + 23 + 30; 10 + 23 + 31; 10 + 23 + 32; 10 + 23 + 33; 10 + 23 + 34; 10 + 23 + 35; 10 + 23 + 36; 10 + 23 + 37 |
| 24 | 10 + 24 + 25; 10 + 24 + 26; 10 + 24 + 27; 10 + 24 + 28; 10 + 24 + 29; 10 + 24 + 30; 10 + 24 + 31; 10 + 24 + 32; 10 + 24 + 33; 10 + 24 + 34; 10 + 24 + 35; 10 + 24 + 36; 10 + 24 + 37 |
| 25 | 10 + 25 + 26; 10 + 25 + 27; 10 + 25 + 28; 10 + 25 + 29; 10 + 25 + 30; 10 + 25 + 31; 10 + 25 + 32; 10 + 25 + 33; 10 + 25 + 34; 10 + 25 + 35; 10 + 25 + 36; 10 + 25 + 37 |
| 26 | 10 + 26 + 27; 10 + 26 + 28; 10 + 26 + 29; 10 + 26 + 30; 10 + 26 + 31; 10 + 26 + 32; 10 + 26 + 33; 10 + 26 + 34; 10 + 26 + 35; 10 + 26 + 36; 10 + 26 + 37 |

TABLE 10-continued (+)Fenchol family of terpene formulations.
Table 10. (+)Fenchol family of terpene formulations. The
numbers refer to the terpenes from Table 1. The
designation "family" is only for convenience in presentation,
as other tables also include formulations with (+)fenchol.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 27 | 10 + 27 + 28; 10 + 27 + 29; 10 + 27 + 30; 10 + 27 + 31; 10 + 27 + 32; 10 + 27 + 33; 10 + 27 + 34; 10 + 27 + 35; 10 + 27 + 36; 10 + 27 + 37 |
| 28 | 10 + 28 + 29; 10 + 28 + 30; 10 + 28 + 31; 10 + 28 + 32; 10 + 28 + 33; 10 + 28 + 34; 10 + 28 + 35; 10 + 28 + 36; 10 + 28 + 37 |
| 29 | 10 + 29 + 30; 10 + 29 + 31; 10 + 29 + 32; 10 + 29 + 33; 10 + 29 + 34; 10 + 29 + 35; 10 + 29 + 36; 10 + 29 + 37 |
| 30 | 10 + 30 + 31; 10 + 30 + 32; 10 + 30 + 33; 10 + 30 + 34; 10 + 30 + 35; 10 + 30 + 36; 10 + 30 + 37 |
| 31 | 10 + 31 + 32; 10 + 31 + 33; 10 + 31 + 34; 10 + 31 + 35; 10 + 31 + 36; 10 + 31 + 37 |
| 32 | 10 + 32 + 33; 10 + 32 + 34; 10 + 32 + 35; 10 + 32 + 36; 10 + 32 + 37 |
| 33 | 10 + 33 + 34; 10 + 33 + 35; 10 + 33 + 36; 10 + 33 + 37 |
| 34 | 10 + 34 + 35; 10 + 34 + 36; 10 + 34 + 37 |
| 35 | 10 + 35 + 36; 10 + 35 + 37 |
| 36 | 10 + 36 + 37 |

TABLE 11

Geraniol family of terpene formulations.
Table 11. Geraniol family of terpene formulations. The numbers
refer to the terpenes from Table 1. The designation "family"
is only for convenience in presentation, as other tables
also include formulations with geraniol.

| Sub-family | Each disclosure of three terpenes represents a distinct formulation. In one embodiment, the formulation that is described by the indicated mixture of the three terpenes does not include any addition terpenes. In other embodiments, it does include additional terpenes. |
|---|---|
| 12 | 11 + 12 + 13, 11 + 12 + 14, 11 + 12 + 15, 11 + 12 + 16, 11 + 12 + 17, 11 + 12 + 18, 11 + 12 + 19, 11 + 12 + 20, 11 + 12 + 21, 11 + 12 + 22, 11 + 12 + 23, 11 + 12 + 24, 11 + 12 + 25, 11 + 12 + 26, 11 + 12 + 27, 11 + 12 + 28, 11 + 12 + 29, 11 + 12 + 30, 11 + 12 + 31, 11 + 12 + 32, 11 + 12 + 33, 11 + 12 + 34, 11 + 12 + 35, 11 + 12 + 36, 11 + 12 + 37 |
| 13 | 11 + 13 + 14, 11 + 13 + 15, 11 + 13 + 16, 11 + 13 + 17, 11 + 13 + 18, 11 + 13 + 19, 11 + 13 + 20, 11 + 13 + 21, 11 + 13 + 22, 11 + 13 + 23, 11 + 13 + 24, 11 + 13 + 25, 11 + 13 + 26, 11 + 13 + 27, 11 + 13 + 28, 11 + 13 + 29, 11 + 13 + 30, 11 + 13 + 31, 11 + 13 + 32, 11 + 13 + 33, 11 + 13 + 34, 11 + 13 + 35, 11 + 13 + 36, 11 + 13 + 37 |
| 14 | 11 + 14 + 15, 11 + 14 + 16, 11 + 14 + 17, 11 + 14 + 18, 11 + 14 + 19, 11 + 14 + 20, 11 + 14 + 21, 11 + 14 + 22, 11 + 14 + 23, 11 + 14 + 24, 11 + 14 + 25, 11 + 14 + 26, 11 + 14 + 27, 11 + 14 + 28, 11 + 14 + 29, 11 + 14 + 30, 11 + 14 + 31, 11 + 14 + 32, 11 + 14 + 33, 11 + 14 + 34, 11 + 14 + 35, 11 + 14 + 36, 11 + 14 + 37 |
| 15 | 11 + 15 + 16, 11 + 15 + 17, 11 + 15 + 18, 11 + 15 + 19, 11 + 15 + 20, 11 + 15 + 21, 11 + 15 + 22, 11 + 15 + 23, 11 + 15 + 24, 11 + 15 + 25, 11 + 15 + 26, 11 + 15 + 27, 11 + 15 + 28, 11 + 15 + 29, 11 + 15 + 30, 11 + 15 + 31, 11 + 15 + 32, 11 + 15 + 33, 11 + 15 + 34, 11 + 15 + 35, 11 + 15 + 36, 11 + 15 + 37 |
| 16 | 11 + 16 + 17, 11 + 16 + 18, 11 + 16 + 19, 11 + 16 + 20, 11 + 16 + 21, 11 + 16 + 22, 11 + 16 + 23, 11 + 16 + 24, 11 + 16 + 25, 11 + 16 + 26, 11 + 16 + 27, 11 + 16 + 28, 11 + 16 + 29, 11 + 16 + 30, 11 + 16 + 31, 11 + 16 + 32, 11 + 16 + 33, 11 + 16 + 34, 11 + 16 + 35, 11 + 16 + 36, 11 + 16 + 37 |

TABLE 11-continued

Geraniol family of terpene formulations.
Table 11. Geraniol family of terpene formulations. The numbers
refer to the terpenes from Table 1. The designation "family"
is only for convenience in presentation, as other tables
also include formulations with geraniol.

| Sub-family | Each disclosure of three terpenes represents a distinct formulation. In one embodiment, the formulation that is described by the indicated mixture of the three terpenes does not include any addition terpenes. In other embodiments, it does include additional terpenes. |
|---|---|
| 17 | 11 + 17 + 18, 11 + 17 + 19, 11 + 17 + 20, 11 + 17 + 21, 11 + 17 + 22, 11 + 17 + 23, 11 + 17 + 24, 11 + 17 + 25, 11 + 17 + 26, 11 + 17 + 27, 11 + 17 + 28, 11 + 17 + 29, 11 + 17 + 30, 11 + 17 + 31, 11 + 17 + 32, 11 + 17 + 33, 11 + 17 + 34, 11 + 17 + 35, 11 + 17 + 36, 11 + 17 + 37 |
| 18 | 11 + 18 + 19, 11 + 18 + 20, 11 + 18 + 21, 11 + 18 + 22, 11 + 18 + 23, 11 + 18 + 24, 11 + 18 + 25, 11 + 18 + 26, 11 + 18 + 27, 11 + 18 + 28, 11 + 18 + 29, 11 + 18 + 30, 11 + 18 + 31, 11 + 18 + 32, 11 + 18 + 33, 11 + 18 + 34, 11 + 18 + 35, 11 + 18 + 36, 11 + 18 + 37 |
| 19 | 11 + 19 + 20, 11 + 19 + 21, 11 + 19 + 22, 11 + 19 + 23, 11 + 19 + 24, 11 + 19 + 25, 11 + 19 + 26, 11 + 19 + 27, 11 + 19 + 28, 11 + 19 + 29, 11 + 19 + 30, 11 + 19 + 31, 11 + 19 + 32, 11 + 19 + 33, 11 + 19 + 34, 11 + 19 + 35, 11 + 19 + 36, 11 + 19 + 37 |
| 20 | 11 + 20 + 21, 11 + 20 + 22, 11 + 20 + 23, 11 + 20 + 24, 11 + 20 + 25, 11 + 20 + 26, 11 + 20 + 27, 11 + 20 + 28, 11 + 20 + 29, 11 + 20 + 30, 11 + 20 + 31, 11 + 20 + 32, 11 + 20 + 33, 11 + 20 + 34, 11 + 20 + 35, 11 + 20 + 36, 11 + 20 + 37 |
| 21 | 11 + 21 + 22, 11 + 21 + 23, 11 + 21 + 24, 11 + 21 + 25, 11 + 21 + 26, 11 + 21 + 27, 11 + 21 + 28, 11 + 21 + 29, 11 + 21 + 30, 11 + 21 + 31, 11 + 21 + 32, 11 + 21 + 33, 11 + 21 + 34, 11 + 21 + 35, 11 + 21 + 36, 11 + 21 + 37 |
| 22 | 11 + 22 + 23, 11 + 22 + 24, 11 + 22 + 25, 11 + 22 + 26, 11 + 22 + 27, 11 + 22 + 28, 11 + 22 + 29, 11 + 22 + 30, 11 + 22 + 31, 11 + 22 + 32, 11 + 22 + 33, 11 + 22 + 34, 11 + 22 + 35, 11 + 22 + 36, 11 + 22 + 37 |
| 23 | 11 + 23 + 24, 11 + 23 + 25, 11 + 23 + 26, 11 + 23 + 27, 11 + 23 + 28, 11 + 23 + 29, 11 + 23 + 30, 11 + 23 + 31, 11 + 23 + 32, 11 + 23 + 33, 11 + 23 + 34, 11 + 23 + 35, 11 + 23 + 36, 11 + 23 + 37 |
| 24 | 11 + 24 + 25, 11 + 24 + 26, 11 + 24 + 27, 11 + 24 + 28, 11 + 24 + 29, 11 + 24 + 30, 11 + 24 + 31, 11 + 24 + 32, 11 + 24 + 33, 11 + 24 + 34, 11 + 24 + 35, 11 + 24 + 36, 11 + 24 + 37 |
| 25 | 11 + 25 + 26, 11 + 25 + 27, 11 + 25 + 28, 11 + 25 + 29, 11 + 25 + 30, 11 + 25 + 31, 11 + 25 + 32, 11 + 25 + 33, 11 + 25 + 34, 11 + 25 + 35, 11 + 25 + 36, 11 + 25 + 37 |
| 26 | 11 + 26 + 27, 11 + 26 + 28, 11 + 26 + 29, 11 + 26 + 30, 11 + 26 + 31, 11 + 26 + 32, 11 + 26 + 33, 11 + 26 + 34, 11 + 26 + 35, 11 + 26 + 36, 11 + 26 + 37 |
| 27 | 11 + 27 + 28, 11 + 27 + 29, 11 + 27 + 30, 11 + 27 + 31, 11 + 27 + 32, 11 + 27 + 33, 11 + 27 + 34, 11 + 27 + 35, 11 + 27 + 36, 11 + 27 + 37 |
| 28 | 11 + 28 + 29, 11 + 28 + 30, 11 + 28 + 31, 11 + 28 + 32, 11 + 28 + 33, 11 + 28 + 34, 11 + 28 + 35, 11 + 28 + 36, 11 + 28 + 37 |
| 29 | 11 + 29 + 30, 11 + 29 + 31, 11 + 29 + 32, 11 + 29 + 33, 11 + 29 + 34, 11 + 29 + 35, 11 + 29 + 36, 11 + 29 + 37 |
| 30 | 11 + 30 + 31, 11 + 30 + 32, 11 + 30 + 33, 11 + 30 + 34, 11 + 30 + 35, 11 + 30 + 36, 11 + 30 + 37 |
| 31 | 11 + 31 + 32, 11 + 31 + 33, 11 + 31 + 34, 11 + 31 + 35, 11 + 31 + 36, 11 + 31 + 37 |
| 32 | 11 + 32 + 33, 11 + 32 + 34, 11 + 32 + 35, 11 + 32 + 36, 11 + 32 + 37 |
| 33 | 11 + 33 + 34, 11 + 33 + 35, 11 + 33 + 36, 11 + 33 + 37 |
| 34 | 11 + 34 + 35, 11 + 34 + 36, 11 + 34 + 37 |
| 35 | 11 + 35 + 36, 11 + 35 + 37 |
| 36 | 11 + 36 + 37 |

TABLE 12

Guaiol family of terpene formulations.
Table 12. Guaiol family of terpene formulations. The numbers refer to the terpenes from Table 1. The designation "family" is only for convenience in presentation, as other tables also include formulations with guaiol.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 13 | 12 + 13 + 14, 12 + 13 + 15, 12 + 13 + 16, 12 + 13 + 17, 12 + 13 + 18, 12 + 13 + 19, 12 + 13 + 20, 12 + 13 + 21, 12 + 13 + 22, 12 + 13 + 23, 12 + 13 + 24, 12 + 13 + 25, 12 + 13 + 26, 12 + 13 + 27, 12 + 13 + 28, 12 + 13 + 29, 12 + 13 + 30, 12 + 13 + 31, 12 + 13 + 32, 12 + 13 + 33, 12 + 13 + 34, 12 + 13 + 35, 12 + 13 + 36, 12 + 13 + 37 |
| 14 | 12 + 14 + 15, 12 + 14 + 16, 12 + 14 + 17, 12 + 14 + 18, 12 + 14 + 19, 12 + 14 + 20, 12 + 14 + 21, 12 + 14 + 22, 12 + 14 + 23, 12 + 14 + 24, 12 + 14 + 25, 12 + 14 + 26, 12 + 14 + 27, 12 + 14 + 28, 12 + 14 + 29, 12 + 14 + 30, 12 + 14 + 31, 12 + 14 + 32, 12 + 14 + 33, 12 + 14 + 34, 12 + 14 + 35, 12 + 14 + 36, 12 + 14 + 37 |
| 15 | 12 + 15 + 16, 12 + 15 + 17, 12 + 15 + 18, 12 + 15 + 19, 12 + 15 + 20, 12 + 15 + 21, 12 + 15 + 22, 12 + 15 + 23, 12 + 15 + 24, 12 + 15 + 25, 12 + 15 + 26, 12 + 15 + 27, 12 + 15 + 28, 12 + 15 + 29, 12 + 15 + 30, 12 + 15 + 31, 12 + 15 + 32, 12 + 15 + 33, 12 + 15 + 34, 12 + 15 + 35, 12 + 15 + 36, 12 + 15 + 37 |
| 16 | 12 + 16 + 17, 12 + 16 + 18, 12 + 16 + 19, 12 + 16 + 20, 12 + 16 + 21, 12 + 16 + 22, 12 + 16 + 23, 12 + 16 + 24, 12 + 16 + 25, 12 + 16 + 26, 12 + 16 + 27, 12 + 16 + 28, 12 + 16 + 29, 12 + 16 + 30, 12 + 16 + 31, 12 + 16 + 32, 12 + 16 + 33, 12 + 16 + 34, 12 + 16 + 35, 12 + 16 + 36, 12 + 16 + 37 |
| 17 | 12 + 17 + 18, 12 + 17 + 19, 12 + 17 + 20, 12 + 17 + 21, 12 + 17 + 22, 12 + 17 + 23, 12 + 17 + 24, 12 + 17 + 25, 12 + 17 + 26, 12 + 17 + 27, 12 + 17 + 28, 12 + 17 + 29, 12 + 17 + 30, 12 + 17 + 31, 12 + 17 + 32, 12 + 17 + 33, 12 + 17 + 34, 12 + 17 + 35, 12 + 17 + 36, 12 + 17 + 37 |
| 18 | 12 + 18 + 19, 12 + 18 + 20, 12 + 18 + 21, 12 + 18 + 22, 12 + 18 + 23, 12 + 18 + 24, 12 + 18 + 25, 12 + 18 + 26, 12 + 18 + 27, 12 + 18 + 28, 12 + 18 + 29, 12 + 18 + 30, 12 + 18 + 31, 12 + 18 + 32, 12 + 18 + 33, 12 + 18 + 34, 12 + 18 + 35, 12 + 18 + 36, 12 + 18 + 37 |
| 19 | 12 + 19 + 20, 12 + 19 + 21, 12 + 19 + 22, 12 + 19 + 23, 12 + 19 + 24, 12 + 19 + 25, 12 + 19 + 26, 12 + 19 + 27, 12 + 19 + 28, 12 + 19 + 29, 12 + 19 + 30, 12 + 19 + 31, 12 + 19 + 32, 12 + 19 + 33, 12 + 19 + 34, 12 + 19 + 35, 12 + 19 + 36, 12 + 19 + 37 |
| 20 | 12 + 20 + 21, 12 + 20 + 22, 12 + 20 + 23, 12 + 20 + 24, 12 + 20 + 25, 12 + 20 + 26, 12 + 20 + 27, 12 + 20 + 28, 12 + 20 + 29, 12 + 20 + 30, 12 + 20 + 31, 12 + 20 + 32, 12 + 20 + 33, 12 + 20 + 34, 12 + 20 + 35, 12 + 20 + 36, 12 + 20 + 37 |
| 21 | 12 + 21 + 22, 12 + 21 + 23, 12 + 21 + 24, 12 + 21 + 25, 12 + 21 + 26, 12 + 21 + 27, 12 + 21 + 28, 12 + 21 + 29, 12 + 21 + 30, 12 + 21 + 31, 12 + 21 + 32, 12 + 21 + 33, 12 + 21 + 34, 12 + 21 + 35, 12 + 21 + 36, 12 + 21 + 37 |
| 22 | 12 + 22 + 23, 12 + 22 + 24, 12 + 22 + 25, 12 + 22 + 26, 12 + 22 + 27, 12 + 22 + 28, 12 + 22 + 29, 12 + 22 + 30, 12 + 22 + 31, 12 + 22 + 32, 12 + 22 + 33, 12 + 22 + 34, 12 + 22 + 35, 12 + 22 + 36, 12 + 22 + 37 |
| 23 | 12 + 23 + 24, 12 + 23 + 25, 12 + 23 + 26, 12 + 23 + 27, 12 + 23 + 28, 12 + 23 + 29, 12 + 23 + 30, 12 + 23 + 31, 12 + 23 + 32, 12 + 23 + 33, 12 + 23 + 34, 12 + 23 + 35, 12 + 23 + 36, 12 + 23 + 37 |
| 24 | 12 + 24 + 25, 12 + 24 + 26, 12 + 24 + 27, 12 + 24 + 28, 12 + 24 + 29, 12 + 24 + 30, 12 + 24 + 31, 12 + 24 + 32, 12 + 24 + 33, 12 + 24 + 34, 12 + 24 + 35, 12 + 24 + 36, 12 + 24 + 37 |
| 25 | 12 + 25 + 26, 12 + 25 + 27, 12 + 25 + 28, 12 + 25 + 29, 12 + 25 + 30, 12 + 25 + 31, 12 + 25 + 32, 12 + 25 + 33, 12 + 25 + 34, 12 + 25 + 35, 12 + 25 + 36, 12 + 25 + 37 |
| 26 | 12 + 26 + 27, 12 + 26 + 28, 12 + 26 + 29, 12 + 26 + 30, 12 + 26 + 31, 12 + 26 + 32, 12 + 26 + 33, 12 + 26 + 34, 12 + 26 + 35, 12 + 26 + 36, 12 + 26 + 37 |
| 27 | 12 + 27 + 28, 12 + 27 + 29, 12 + 27 + 30, 12 + 27 + 31, 12 + 27 + 32, 12 + 27 + 33, 12 + 27 + 34, 12 + 27 + 35, 12 + 27 + 36, 12 + 27 + 37 |
| 28 | 12 + 28 + 29, 12 + 28 + 30, 12 + 28 + 31, 12 + 28 + 32, 12 + 28 + 33, 12 + 28 + 34, 12 + 28 + 35, 12 + 28 + 36, 12 + 28 + 37 |
| 29 | 12 + 29 + 30, 12 + 29 + 31, 12 + 29 + 32, 12 + 29 + 33, 12 + 29 + 34, 12 + 29 + 35, 12 + 29 + 36, 12 + 29 + 37 |
| 30 | 12 + 30 + 31, 12 + 30 + 32, 12 + 30 + 33, 12 + 30 + 34, 12 + 30 + 35, 12 + 30 + 36, 12 + 30 + 37 |
| 31 | 12 + 31 + 32, 12 + 31 + 33, 12 + 31 + 34, 12 + 31 + 35, 12 + 31 + 36, 12 + 31 + 37 |
| 32 | 12 + 32 + 33, 12 + 32 + 34, 12 + 32 + 35, 12 + 32 + 36, 12 + 32 + 37 |
| 33 | 12 + 33 + 34, 12 + 33 + 35, 12 + 33 + 36, 12 + 33 + 37 |
| 34 | 12 + 34 + 35, 12 + 34 + 36, 12 + 34 + 37 |
| 35 | 12 + 35 + 36, 12 + 35 + 37 |
| 36 | 12 + 36 + 37 |

TABLE 13

Alpha-humulene family of terpene formulations.
Table 13. Alpha-humulene family of terpene formulations. The numbers refer to the terpenes from Table 1. The designation "family" is only for convenience in presentation, as other tables also include formulations with alpha-humulene.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 14 | 13 + 14 + 15, 13 + 14 + 16, 13 + 14 + 17, 13 + 14 + 18, 13 + 14 + 19, 13 + 14 + 20, 13 + 14 + 21, 13 + 14 + 22, 13 + 14 + 23, 13 + 14 + 24, 13 + 14 + 25, 13 + 14 + 26, 13 + 14 + 27, 13 + 14 + 28, 13 + 14 + 29, 13 + 14 + 30, 13 + 14 + 31, 13 + 14 + 32, 13 + 14 + 33, 13 + 14 + 34, 13 + 14 + 35, 13 + 14 + 36, 13 + 14 + 37 |
| 15 | 13 + 15 + 16, 13 + 15 + 17, 13 + 15 + 18, 13 + 15 + 19, 13 + 15 + 20, 13 + 15 + 21, 13 + 15 + 22, 13 + 15 + 23, 13 + 15 + 24, 13 + 15 + 25, 13 + 15 + 26, 13 + 15 + 27, 13 + 15 + 28, 13 + 15 + 29, 13 + 15 + 30, 13 + 15 + 31, 13 + 15 + 32, 13 + 15 + 33, 13 + 15 + 34, 13 + 15 + 35, 13 + 15 + 36, 13 + 15 + 37 |
| 16 | 13 + 16 + 17, 13 + 16 + 18, 13 + 16 + 19, 13 + 16 + 20, 13 + 16 + 21, 13 + 16 + 22, 13 + 16 + 23, 13 + 16 + 24, 13 + 16 + 25, 13 + 16 + 26, 13 + 16 + 27, 13 + 16 + 28, 13 + 16 + 29, 13 + 16 + 30, 13 + 16 + 31, 13 + 16 + 32, 13 + 16 + 33, 13 + 16 + 34, 13 + 16 + 35, 13 + 16 + 36, 13 + 16 + 37 |
| 17 | 13 + 17 + 18, 13 + 17 + 19, 13 + 17 + 20, 13 + 17 + 21, 13 + 17 + 22, 13 + 17 + 23, 13 + 17 + 24, 13 + 17 + 25, 13 + 17 + 26, 13 + 17 + 27, 13 + 17 + 28, 13 + 17 + 29, 13 + 17 + 30, 13 + 17 + 31, 13 + 17 + 32, 13 + 17 + 33, 13 + 17 + 34, 13 + 17 + 35, 13 + 17 + 36, 13 + 17 + 37 |
| 18 | 13 + 18 + 19, 13 + 18 + 20, 13 + 18 + 21, 13 + 18 + 22, 13 + 18 + 23, 13 + 18 + 24, 13 + 18 + 25, 13 + 18 + 26, 13 + 18 + 27, 13 + 18 + 28, 13 + 18 + 29, 13 + 18 + 30, 13 + 18 + 31, 13 + 18 + 32, 13 + 18 + 33, 13 + 18 + 34, 13 + 18 + 35, 13 + 18 + 36, 13 + 18 + 37 |

TABLE 13-continued

Alpha-humulene family of terpene formulations.
Table 13. Alpha-humulene family of terpene formulations. The numbers refer to the terpenes from Table 1. The designation "family" is only for convenience in presentation, as other tables also include formulations with alpha-humulene.

Each disclosure of three terpenes represents a distinct formulation. In one embodiment, the formulation that is described by the indicated mixture of the three terpenes does not include any additional terpenes. In other embodiments, it does include additional terpenes.

| Sub-family | |
|---|---|
| 19 | 13 + 19 + 20, 13 + 19 + 21, 13 + 19 + 22, 13 + 19 + 23, 13 + 19 + 24, 13 + 19 + 25, 13 + 19 + 26, 13 + 19 + 27, 13 + 19 + 28, 13 + 19 + 29, 13 + 19 + 30, 13 + 19 + 31, 13 + 19 + 32, 13 + 19 + 33, 13 + 19 + 34, 13 + 19 + 35, 13 + 19 + 36, 13 + 19 + 37 |
| 20 | 13 + 20 + 21, 13 + 20 + 22, 13 + 20 + 23, 13 + 20 + 24, 13 + 20 + 25, 13 + 20 + 26, 13 + 20 + 27, 13 + 20 + 28, 13 + 20 + 29, 13 + 20 + 30, 13 + 20 + 31, 13 + 20 + 32, 13 + 20 + 33, 13 + 20 + 34, 13 + 20 + 35, 13 + 20 + 36, 13 + 20 + 37 |
| 21 | 13 + 21 + 22, 13 + 21 + 23, 13 + 21 + 24, 13 + 21 + 25, 13 + 21 + 26, 13 + 21 + 27, 13 + 21 + 28, 13 + 21 + 29, 13 + 21 + 30, 13 + 21 + 31, 13 + 21 + 32, 13 + 21 + 33, 13 + 21 + 34, 13 + 21 + 35, 13 + 21 + 36, 13 + 21 + 37 |
| 22 | 13 + 22 + 23, 13 + 22 + 24, 13 + 22 + 25, 13 + 22 + 26, 13 + 22 + 27, 13 + 22 + 28, 13 + 22 + 29, 13 + 22 + 30, 13 + 22 + 31, 13 + 22 + 32, 13 + 22 + 33, 13 + 22 + 34, 13 + 22 + 35, 13 + 22 + 36, 13 + 22 + 37 |
| 23 | 13 + 23 + 24, 13 + 23 + 25, 13 + 23 + 26, 13 + 23 + 27, 13 + 23 + 28, 13 + 23 + 29, 13 + 23 + 30, 13 + 23 + 31, 13 + 23 + 32, 13 + 23 + 33, 13 + 23 + 34, 13 + 23 + 35, 13 + 23 + 36, 13 + 23 + 37 |
| 24 | 13 + 24 + 25, 13 + 24 + 26, 13 + 24 + 27, 13 + 24 + 28, 13 + 24 + 29, 13 + 24 + 30, 13 + 24 + 31, 13 + 24 + 32, 13 + 24 + 33, 13 + 24 + 34, 13 + 24 + 35, 13 + 24 + 36, 13 + 24 + 37 |
| 25 | 13 + 25 + 26, 13 + 25 + 27, 13 + 25 + 28, 13 + 25 + 29, 13 + 25 + 30, 13 + 25 + 31, 13 + 25 + 32, 13 + 25 + 33, 13 + 25 + 34, 13 + 25 + 35, 13 + 25 + 36, 13 + 25 + 37 |
| 26 | 13 + 26 + 27, 13 + 26 + 28, 13 + 26 + 29, 13 + 26 + 30, 13 + 26 + 31, 13 + 26 + 32, 13 + 26 + 33, 13 + 26 + 34, 13 + 26 + 35, 13 + 26 + 36, 13 + 26 + 37 |
| 27 | 13 + 27 + 28, 13 + 27 + 29, 13 + 27 + 30, 13 + 27 + 31, 13 + 27 + 32, 13 + 27 + 33, 13 + 27 + 34, 13 + 27 + 35, 13 + 27 + 36, 13 + 27 + 37 |
| 28 | 13 + 28 + 29, 13 + 28 + 30, 13 + 28 + 31, 13 + 28 + 32, 13 + 28 + 33, 13 + 28 + 34, 13 + 28 + 35, 13 + 28 + 36, 13 + 28 + 37 |
| 29 | 13 + 29 + 30, 13 + 29 + 31, 13 + 29 + 32, 13 + 29 + 33, 13 + 29 + 34, 13 + 29 + 35, 13 + 29 + 36, 13 + 29 + 37 |
| 30 | 13 + 30 + 31, 13 + 30 + 32, 13 + 30 + 33, 13 + 30 + 34, 13 + 30 + 35, 13 + 30 + 36, 13 + 30 + 37 |
| 31 | 13 + 31 + 32, 13 + 31 + 33, 13 + 31 + 34, 13 + 31 + 35, 13 + 31 + 36, 13 + 31 + 37 |
| 32 | 13 + 32 + 33, 13 + 32 + 34, 13 + 32 + 35, 13 + 32 + 36, 13 + 32 + 37 |
| 33 | 13 + 33 + 34, 13 + 33 + 35, 13 + 33 + 36, 13 + 33 + 37 |
| 34 | 13 + 34 + 35, 13 + 34 + 36, 13 + 34 + 37 |
| 35 | 13 + 35 + 36, 13 + 35 + 37 |
| 36 | 13 + 36 + 37 |

TABLE 14

Isoborneol family of terpene formulations.
Table 14. Isoborneol family of terpene formulations. The numbers refer to the terpenes from Table 1. The designation "family" is only for convenience in presentation, as other tables also include formulations with isoborneol.

Each disclosure of three terpenes represents a distinct formulation. In one embodiment, the formulation that is described by the indicated mixture of the three terpenes does not include any additional terpenes. In other embodiments, it does include additional terpenes.

| Sub-family | |
|---|---|
| 15 | 14 + 15 + 16, 14 + 15 + 17, 14 + 15 + 18, 14 + 15 + 19, 14 + 15 + 20, 14 + 15 + 21, 14 + 15 + 22, 14 + 15 + 23, 14 + 15 + 24, 14 + 15 + 25, 14 + 15 + 26, 14 + 15 + 27, 14 + 15 + 28, 14 + 15 + 29, 14 + 15 + 30, 14 + 15 + 31, 14 + 15 + 32, 14 + 15 + 33, 14 + 15 + 34, 14 + 15 + 35, 14 + 15 + 36, 14 + 15 + 37 |
| 16 | 14 + 16 + 17, 14 + 16 + 18, 14 + 16 + 19, 14 + 16 + 20, 14 + 16 + 21, 14 + 16 + 22, 14 + 16 + 23, 14 + 16 + 24, 14 + 16 + 25, 14 + 16 + 26, 14 + 16 + 27, 14 + 16 + 28, 14 + 16 + 29, 14 + 16 + 30, 14 + 16 + 31, 14 + 16 + 32, 14 + 16 + 33, 14 + 16 + 34, 14 + 16 + 35, 14 + 16 + 36, 14 + 16 + 37 |
| 17 | 14 + 17 + 18, 14 + 17 + 19, 14 + 17 + 20, 14 + 17 + 21, 14 + 17 + 22, 14 + 17 + 23, 14 + 17 + 24, 14 + 17 + 25, 14 + 17 + 26, 14 + 17 + 27, 14 + 17 + 28, 14 + 17 + 29, 14 + 17 + 30, 14 + 17 + 31, 14 + 17 + 32, 14 + 17 + 33, 14 + 17 + 34, 14 + 17 + 35, 14 + 17 + 36, 14 + 17 + 37 |
| 18 | 14 + 18 + 19, 14 + 18 + 20, 14 + 18 + 21, 14 + 18 + 22, 14 + 18 + 23, 14 + 18 + 24, 14 + 18 + 25, 14 + 18 + 26, 14 + 18 + 27, 14 + 18 + 28, 14 + 18 + 29, 14 + 18 + 30, 14 + 18 + 31, 14 + 18 + 32, 14 + 18 + 33, 14 + 18 + 34, 14 + 18 + 35, 14 + 18 + 36, 14 + 18 + 37 |
| 19 | 14 + 19 + 20, 14 + 19 + 21, 14 + 19 + 22, 14 + 19 + 23, 14 + 19 + 24, 14 + 19 + 25, 14 + 19 + 26, 14 + 19 + 27, 14 + 19 + 28, 14 + 19 + 29, 14 + 19 + 30, 14 + 19 + 31, 14 + 19 + 32, 14 + 19 + 33, 14 + 19 + 34, 14 + 19 + 35, 14 + 19 + 36, 14 + 19 + 37 |
| 20 | 14 + 20 + 21, 14 + 20 + 22, 14 + 20 + 23, 14 + 20 + 24, 14 + 20 + 25, 14 + 20 + 26, 14 + 20 + 27, 14 + 20 + 28, 14 + 20 + 29, 14 + 20 + 30, 14 + 20 + 31, 14 + 20 + 32, 14 + 20 + 33, 14 + 20 + 34, 14 + 20 + 35, 14 + 20 + 36, 14 + 20 + 37 |
| 21 | 14 + 21 + 22, 14 + 21 + 23, 14 + 21 + 24, 14 + 21 + 25, 14 + 21 + 26, 14 + 21 + 27, 14 + 21 + 28, 14 + 21 + 29, 14 + 21 + 30, 14 + 21 + 31, 14 + 21 + 32, 14 + 21 + 33, 14 + 21 + 34, 14 + 21 + 35, 14 + 21 + 36, 14 + 21 + 37 |
| 22 | 14 + 22 + 23, 14 + 22 + 24, 14 + 22 + 25, 14 + 22 + 26, 14 + 22 + 27, 14 + 22 + 28, 14 + 22 + 29, 14 + 22 + 30, 14 + 22 + 31, 14 + 22 + 32, 14 + 22 + 33, 14 + 22 + 34, 14 + 22 + 35, 14 + 22 + 36, 14 + 22 + 37 |
| 23 | 14 + 23 + 24, 14 + 23 + 25, 14 + 23 + 26, 14 + 23 + 27, 14 + 23 + 28, 14 + 23 + 29, 14 + 23 + 30, 14 + 23 + 31, 14 + 23 + 32, 14 + 23 + 33, 14 + 23 + 34, 14 + 23 + 35, 14 + 23 + 36, 14 + 23 + 37 |
| 24 | 14 + 24 + 25, 14 + 24 + 26, 14 + 24 + 27, 14 + 24 + 28, 14 + 24 + 29, 14 + 24 + 30, 14 + 24 + 31, 14 + 24 + 32, 14 + 24 + 33, 14 + 24 + 34, 14 + 24 + 35, 14 + 24 + 36, 14 + 24 + 37 |
| 25 | 14 + 25 + 26, 14 + 25 + 27, 14 + 25 + 28, 14 + 25 + 29, 14 + 25 + 30, 14 + 25 + 31, 14 + 25 + 32, 14 + 25 + 33, 14 + 25 + 34, 14 + 25 + 35, 14 + 25 + 36, 14 + 25 + 37 |
| 26 | 14 + 26 + 27, 14 + 26 + 28, 14 + 26 + 29, 14 + 26 + 30, 14 + 26 + 31, 14 + 26 + 32, 14 + 26 + 33, 14 + 26 + 34, 14 + 26 + 35, 14 + 26 + 36, 14 + 26 + 37 |
| 27 | 14 + 27 + 28, 14 + 27 + 29, 14 + 27 + 30, 14 + 27 + 31, 14 + 27 + 32, 14 + 27 + 33, 14 + 27 + 34, 14 + 27 + 35, 14 + 27 + 36, 14 + 27 + 37 |
| 28 | 14 + 28 + 29, 14 + 28 + 30, 14 + 28 + 31, 14 + 28 + 32, 14 + 28 + 33, 14 + 28 + 34, 14 + 28 + 35, 14 + 28 + 36, 14 + 28 + 37 |
| 29 | 14 + 29 + 30, 14 + 29 + 31, 14 + 29 + 32, 14 + 29 + 33, 14 + 29 + 34, 14 + 29 + 35, 14 + 29 + 36, 14 + 29 + 37 |
| 30 | 14 + 30 + 31, 14 + 30 + 32, 14 + 30 + 33, 14 + 30 + 34, 14 + 30 + 35, 14 + 30 + 36, 14 + 30 + 37 |
| 31 | 14 + 31 + 32, 14 + 31 + 33, 14 + 31 + 34, 14 + 31 + 35, 14 + 31 + 36, 14 + 31 + 37 |
| 32 | 14 + 32 + 33, 14 + 32 + 34, 14 + 32 + 35, 14 + 32 + 36, 14 + 32 + 37 |

TABLE 14-continued

Isoborneol family of terpene formulations.
Table 14. Isoborneol family of terpene formulations. The numbers refer to the terpenes from Table 1. The designation "family" is only for convenience in presentation, as other tables also include formulations with isoborneol.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
| --- | --- |
| 33 | 14 + 33 + 34, 14 + 33 + 35, 14 + 33 + 36, 14 + 33 + 37 |
| 34 | 14 + 34 + 35, 14 + 34 + 36, 14 + 34 + 37 |
| 35 | 14 + 35 + 36, 14 + 35 + 37 |
| 36 | 14 + 36 + 37 |

TABLE 15

Limonene family of terpene formulations.
Table 15. Limonene family of terpene formulations. The numbers refer to the terpenes from Table 1. The designation "family" is only for convenience in presentation, as other tables also include formulations with limonene.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
| --- | --- |
| 16 | 15 + 16 + 17, 15 + 16 + 18, 15 + 16 + 19, 15 + 16 + 20, 15 + 16 + 21, 15 + 16 + 22, 15 + 16 + 23, 15 + 16 + 24, 15 + 16 + 25, 15 + 16 + 26, 15 + 16 + 27, 15 + 16 + 28, 15 + 16 + 29, 15 + 16 + 30, 15 + 16 + 31, 15 + 16 + 32, 15 + 16 + 33, 15 + 16 + 34, 15 + 16 + 35, 15 + 16 + 36, 15 + 16 + 37 |
| 17 | 15 + 17 + 18, 15 + 17 + 19, 15 + 17 + 20, 15 + 17 + 21, 15 + 17 + 22, 15 + 17 + 23, 15 + 17 + 24, 15 + 17 + 25, 15 + 17 + 26, 15 + 17 + 27, 15 + 17 + 28, 15 + 17 + 29, 15 + 17 + 30, 15 + 17 + 31, 15 + 17 + 32, 15 + 17 + 33, 15 + 17 + 34, 15 + 17 + 35, 15 + 17 + 36, 15 + 17 + 37 |
| 18 | 15 + 18 + 19, 15 + 18 + 20, 15 + 18 + 21, 15 + 18 + 22, 15 + 18 + 23, 15 + 18 + 24, 15 + 18 + 25, 15 + 18 + 26, 15 + 18 + 27, 15 + 18 + 28, 15 + 18 + 29, 15 + 18 + 30, 15 + 18 + 31, 15 + 18 + 32, 15 + 18 + 33, 15 + 18 + 34, 15 + 18 + 35, 15 + 18 + 36, 15 + 18 + 37 |
| 19 | 15 + 19 + 20, 15 + 19 + 21, 15 + 19 + 22, 15 + 19 + 23, 15 + 19 + 24, 15 + 19 + 25, 15 + 19 + 26, 15 + 19 + 27, 15 + 19 + 28, 15 + 19 + 29, 15 + 19 + 30, 15 + 19 + 31, 15 + 19 + 32, 15 + 19 + 33, 15 + 19 + 34, 15 + 19 + 35, 15 + 19 + 36, 15 + 19 + 37 |
| 20 | 15 + 20 + 21, 15 + 20 + 22, 15 + 20 + 23, 15 + 20 + 24, 15 + 20 + 25, 15 + 20 + 26, 15 + 20 + 27, 15 + 20 + 28, 15 + 20 + 29, 15 + 20 + 30, 15 + 20 + 31, 15 + 20 + 32, 15 + 20 + 33, 15 + 20 + 34, 15 + 20 + 35, 15 + 20 + 36, 15 + 20 + 37 |
| 21 | 15 + 21 + 22, 15 + 21 + 23, 15 + 21 + 24, 15 + 21 + 25, 15 + 21 + 26, 15 + 21 + 27, 15 + 21 + 28, 15 + 21 + 29, 15 + 21 + 30, 15 + 21 + 31, 15 + 21 + 32, 15 + 21 + 33, 15 + 21 + 34, 15 + 21 + 35, 15 + 21 + 36, 15 + 21 + 37 |
| 22 | 15 + 22 + 23, 15 + 22 + 24, 15 + 22 + 25, 15 + 22 + 26, 15 + 22 + 27, 15 + 22 + 28, 15 + 22 + 29, 15 + 22 + 30, 15 + 22 + 31, 15 + 22 + 32, 15 + 22 + 33, 15 + 22 + 34, 15 + 22 + 35, 15 + 22 + 36, 15 + 22 + 37 |
| 23 | 15 + 23 + 24, 15 + 23 + 25, 15 + 23 + 26, 15 + 23 + 27, 15 + 23 + 28, 15 + 23 + 29, 15 + 23 + 30, 15 + 23 + 31, 15 + 23 + 32, 15 + 23 + 33, 15 + 23 + 34, 15 + 23 + 35, 15 + 23 + 36, 15 + 23 + 37 |
| 24 | 15 + 24 + 25, 15 + 24 + 26, 15 + 24 + 27, 15 + 24 + 28, 15 + 24 + 29, 15 + 24 + 30, 15 + 24 + 31, 15 + 24 + 32, 15 + 24 + 33, 15 + 24 + 34, 15 + 24 + 35, 15 + 24 + 36, 15 + 24 + 37 |
| 25 | 15 + 25 + 26, 15 + 25 + 27, 15 + 25 + 28, 15 + 25 + 29, 15 + 25 + 30, 15 + 25 + 31, 15 + 25 + 32, 15 + 25 + 33, 15 + 25 + 34, 15 + 25 + 35, 15 + 25 + 36, 15 + 25 + 37 |

TABLE 15-continued

Limonene family of terpene formulations.
Table 15. Limonene family of terpene formulations. The numbers refer to the terpenes from Table 1. The designation "family" is only for convenience in presentation, as other tables also include formulations with limonene.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
| --- | --- |
| 26 | 15 + 26 + 27, 15 + 26 + 28, 15 + 26 + 29, 15 + 26 + 30, 15 + 26 + 31, 15 + 26 + 32, 15 + 26 + 33, 15 + 26 + 34, 15 + 26 + 35, 15 + 26 + 36, 15 + 26 + 37 |
| 27 | 15 + 27 + 28, 15 + 27 + 29, 15 + 27 + 30, 15 + 27 + 31, 15 + 27 + 32, 15 + 27 + 33, 15 + 27 + 34, 15 + 27 + 35, 15 + 27 + 36, 15 + 27 + 37 |
| 28 | 15 + 28 + 29, 15 + 28 + 30, 15 + 28 + 31, 15 + 28 + 32, 15 + 28 + 33, 15 + 28 + 34, 15 + 28 + 35, 15 + 28 + 36, 15 + 28 + 37 |
| 29 | 15 + 29 + 30, 15 + 29 + 31, 15 + 29 + 32, 15 + 29 + 33, 15 + 29 + 34, 15 + 29 + 35, 15 + 29 + 36, 15 + 29 + 37 |
| 30 | 15 + 30 + 31, 15 + 30 + 32, 15 + 30 + 33, 15 + 30 + 34, 15 + 30 + 35, 15 + 30 + 36, 15 + 30 + 37 |
| 31 | 15 + 31 + 32, 15 + 31 + 33, 15 + 31 + 34, 15 + 31 + 35, 15 + 31 + 36, 15 + 31 + 37 |
| 32 | 15 + 32 + 33, 15 + 32 + 34, 15 + 32 + 35, 15 + 32 + 36, 15 + 32 + 37 |
| 33 | 15 + 33 + 34, 15 + 33 + 35, 15 + 33 + 36, 15 + 33 + 37 |
| 34 | 15 + 34 + 35, 15 + 34 + 36, 15 + 34 + 37 |
| 35 | 15 + 35 + 36, 15 + 35 + 37 |
| 36 | 15 + 36 + 37 |

TABLE 16

Linalool family of terpene formulations.
Table 16. Linalool family of terpene formulations. The numbers refer to the terpenes from Table 1. The designation "family" is only for convenience in presentation, as other tables also include formulations with linalool.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
| --- | --- |
| 17 | 16 + 17 + 18, 16 + 17 + 19, 16 + 17 + 20, 16 + 17 + 21, 16 + 17 + 22, 16 + 17 + 23, 16 + 17 + 24, 16 + 17 + 25, 16 + 17 + 26, 16 + 17 + 27, 16 + 17 + 28, 16 + 17 + 29, 16 + 17 + 30, 16 + 17 + 31, 16 + 17 + 32, 16 + 17 + 33, 16 + 17 + 34, 16 + 17 + 35, 16 + 17 + 36, 16 + 17 + 37 |
| 18 | 16 + 18 + 19, 16 + 18 + 20, 16 + 18 + 21, 16 + 18 + 22, 16 + 18 + 23, 16 + 18 + 24, 16 + 18 + 25, 16 + 18 + 26, 16 + 18 + 27, 16 + 18 + 28, 16 + 18 + 29, 16 + 18 + 30, 16 + 18 + 31, 16 + 18 + 32, 16 + 18 + 33, 16 + 18 + 34, 16 + 18 + 35, 16 + 18 + 36, 16 + 18 + 37 |
| 19 | 16 + 19 + 20, 16 + 19 + 21, 16 + 19 + 22, 16 + 19 + 23, 16 + 19 + 24, 16 + 19 + 25, 16 + 19 + 26, 16 + 19 + 27, 16 + 19 + 28, 16 + 19 + 29, 16 + 19 + 30, 16 + 19 + 31, 16 + 19 + 32, 16 + 19 + 33, 16 + 19 + 34, 16 + 19 + 35, 16 + 19 + 36, 16 + 19 + 37 |
| 20 | 16 + 20 + 21, 16 + 20 + 22, 16 + 20 + 23, 16 + 20 + 24, 16 + 20 + 25, 16 + 20 + 26, 16 + 20 + 27, 16 + 20 + 28, 16 + 20 + 29, 16 + 20 + 30, 16 + 20 + 31, 16 + 20 + 32, 16 + 20 + 33, 16 + 20 + 34, 16 + 20 + 35, 16 + 20 + 36, 16 + 20 + 37 |
| 21 | 16 + 21 + 22, 16 + 21 + 23, 16 + 21 + 24, 16 + 21 + 25, 16 + 21 + 26, 16 + 21 + 27, 16 + 21 + 28, 16 + 21 + 29, 16 + 21 + 30, 16 + 21 + 31, 16 + 21 + 32, 16 + 21 + 33, 16 + 21 + 34, 16 + 21 + 35, 16 + 21 + 36, 16 + 21 + 37 |
| 22 | 16 + 22 + 23, 16 + 22 + 24, 16 + 22 + 25, 16 + 22 + 26, 16 + 22 + 27, 16 + 22 + 28, 16 + 22 + 29, 16 + 22 + 30, 16 + 22 + 31, 16 + 22 + 32, 16 + 22 + 33, 16 + 22 + 34, 16 + 22 + 35, 16 + 22 + 36, 16 + 22 + 37 |

TABLE 16-continued

Linalool family of terpene formulations.
Table 16. Linalool family of
terpene formulations. The numbers refer to the terpenes
from Table 1. The designation "family" is only for convenience in
presentation, as other tables also include formulations with linalool.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 23 | 16 + 23 + 24, 16 + 23 + 25, 16 + 23 + 26, 16 + 23 + 27, 16 + 23 + 28, 16 + 23 + 29, 16 + 23 + 30, 16 + 23 + 31, 16 + 23 + 32, 16 + 23 + 33, 16 + 23 + 34, 16 + 23 + 35, 16 + 23 + 36, 16 + 23 + 37 |
| 24 | 16 + 24 + 25, 16 + 24 + 26, 16 + 24 + 27, 16 + 24 + 28, 16 + 24 + 29, 16 + 24 + 30, 16 + 24 + 31, 16 + 24 + 32, 16 + 24 + 33, 16 + 24 + 34, 16 + 24 + 35, 16 + 24 + 36, 16 + 24 + 37 |
| 25 | 16 + 25 + 26, 16 + 25 + 27, 16 + 25 + 28, 16 + 25 + 29, 16 + 25 + 30, 16 + 25 + 31, 16 + 25 + 32, 16 + 25 + 33, 16 + 25 + 34, 16 + 25 + 35, 16 + 25 + 36, 16 + 25 + 37 |
| 26 | 16 + 26 + 27, 16 + 26 + 28, 16 + 26 + 29, 16 + 26 + 30, 16 + 26 + 31, 16 + 26 + 32, 16 + 26 + 33, 16 + 26 + 34, 16 + 26 + 35, 16 + 26 + 36, 16 + 26 + 37 |
| 27 | 16 + 27 + 28, 16 + 27 + 29, 16 + 27 + 30, 16 + 27 + 31, 16 + 27 + 32, 16 + 27 + 33, 16 + 27 + 34, 16 + 27 + 35, 16 + 27 + 36, 16 + 27 + 37 |
| 28 | 16 + 28 + 29, 16 + 28 + 30, 16 + 28 + 31, 16 + 28 + 32, 16 + 28 + 33, 16 + 28 + 34, 16 + 28 + 35, 16 + 28 + 36, 16 + 28 + 37 |
| 29 | 16 + 29 + 30, 16 + 29 + 31, 16 + 29 + 32, 16 + 29 + 33, 16 + 29 + 34, 16 + 29 + 35, 16 + 29 + 36, 16 + 29 + 37 |
| 30 | 16 + 30 + 31, 16 + 30 + 32, 16 + 30 + 33, 16 + 30 + 34, 16 + 30 + 35, 16 + 30 + 36, 16 + 30 + 37 |
| 31 | 16 + 31 + 32, 16 + 31 + 33, 16 + 31 + 34, 16 + 31 + 35, 16 + 31 + 36, 16 + 31 + 37 |
| 32 | 16 + 32 + 33, 16 + 32 + 34, 16 + 32 + 35, 16 + 32 + 36, 16 + 32 + 37 |
| 33 | 16 + 33 + 34, 16 + 33 + 35, 16 + 33 + 36, 16 + 33 + 37 |
| 34 | 16 + 34 + 35, 16 + 34 + 36, 16 + 34 + 37 |
| 35 | 16 + 35 + 35, 16 + 35 + 37 |
| 36 | 16 + 36 + 37 |

TABLE 17

Menthol family of terpene formulations.
Table 17. Menthol family of
terpene formulations. The numbers refer to the terpenes
from Table 1. The designation "family" is only for convenience in
presentation, as other tables also include formulations with menthol.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 18 | 17 + 18 + 19, 17 + 18 + 20, 17 + 18 + 21, 17 + 18 + 22, 17 + 18 + 23, 17 + 18 + 24, 17 + 18 + 25, 17 + 18 + 26, 17 + 18 + 27, 17 + 18 + 28, 17 + 18 + 29, 17 + 18 + 30, 17 + 18 + 31, 17 + 18 + 32, 17 + 18 + 33, 17 + 18 + 34, 17 + 18 + 35, 17 + 18 + 36, 17 + 18 + 37 |
| 19 | 17 + 19 + 20, 17 + 19 + 21, 17 + 19 + 22, 17 + 19 + 23, 17 + 19 + 24, 17 + 19 + 25, 17 + 19 + 26, 17 + 19 + 27, 17 + 19 + 28, 17 + 19 + 29, 17 + 19 + 30, 17 + 19 + 31, 17 + 19 + 32, 17 + 19 + 33, 17 + 19 + 34, 17 + 19 + 35, 17 + 19 + 36, 17 + 19 + 37 |
| 20 | 17 + 20 + 21, 17 + 20 + 22, 17 + 20 + 23, 17 + 20 + 24, 17 + 20 + 25, 17 + 20 + 26, 17 + 20 + 27, 17 + 20 + 28, 17 + 20 + 29, 17 + 20 + 30, 17 + 20 + 31, 17 + 20 + 32, 17 + 20 + 33, 17 + 20 + 34, 17 + 20 + 35, 17 + 20 + 36, 17 + 20 + 37 |
| 21 | 17 + 21 + 22, 17 + 21 + 23, 17 + 21 + 24, 17 + 21 + 25, 17 + 21 + 26, 17 + 21 + 27, 17 + 21 + 28, 17 + 21 + 29, 17 + 21 + 30, 17 + 21 + 31, 17 + 21 + 32, 17 + 21 + 33, 17 + 21 + 34, 17 + 21 + 35, 17 + 21 + 36, 17 + 21 + 37 |
| 22 | 17 + 22 + 23, 17 + 22 + 24, 17 + 22 + 25, 17 + 22 + 26, 17 + 22 + 27, 17 + 22 + 28, 17 + 22 + 29, 17 + 22 + 30, 17 + 22 + 31, 17 + 22 + 32, 17 + 22 + 33, 17 + 22 + 34, 17 + 22 + 35, 17 + 22 + 36, 17 + 22 + 37 |
| 23 | 17 + 23 + 24, 17 + 23 + 25, 17 + 23 + 26, 17 + 23 + 27, 17 + 23 + 28, 17 + 23 + 29, 17 + 23 + 30, 17 + 23 + 31, 17 + 23 + 32, 17 + 23 + 33, 17 + 23 + 34, 17 + 23 + 35, 17 + 23 + 36, 17 + 23 + 37 |
| 24 | 17 + 24 + 25, 17 + 24 + 26, 17 + 24 + 27, 17 + 24 + 28, 17 + 24 + 29, 17 + 24 + 30, 17 + 24 + 31, 17 + 24 + 32, 17 + 24 + 33, 17 + 24 + 34, 17 + 24 + 35, 17 + 24 + 36, 17 + 24 + 37 |
| 25 | 17 + 25 + 26, 17 + 25 + 27, 17 + 25 + 28, 17 + 25 + 29, 17 + 25 + 30, 17 + 25 + 31, 17 + 25 + 32, 17 + 25 + 33, 17 + 25 + 34, 17 + 25 + 35, 17 + 25 + 36, 17 + 25 + 37 |
| 26 | 17 + 26 + 27, 17 + 26 + 28, 17 + 26 + 29, 17 + 26 + 30, 17 + 26 + 31, 17 + 26 + 32, 17 + 26 + 33, 17 + 26 + 34, 17 + 26 + 35, 17 + 26 + 36, 17 + 26 + 37 |
| 27 | 17 + 27 + 28, 17 + 27 + 29, 17 + 27 + 30, 17 + 27 + 31, 17 + 27 + 32, 17 + 27 + 33, 17 + 27 + 34, 17 + 27 + 35, 17 + 27 + 36, 17 + 27 + 37 |
| 28 | 17 + 28 + 29, 17 + 28 + 30, 17 + 28 + 31, 17 + 28 + 32, 17 + 28 + 33, 17 + 28 + 34, 17 + 28 + 35, 17 + 28 + 36, 17 + 28 + 37 |
| 29 | 17 + 29 + 30, 17 + 29 + 31, 17 + 29 + 32, 17 + 29 + 33, 17 + 29 + 34, 17 + 29 + 35, 17 + 29 + 36, 17 + 29 + 37 |
| 30 | 17 + 30 + 31, 17 + 30 + 32, 17 + 30 + 33, 17 + 30 + 34, 17 + 30 + 35, 17 + 30 + 36, 17 + 30 + 37 |
| 31 | 17 + 31 + 32, 17 + 31 + 33, 17 + 31 + 34, 17 + 31 + 35, 17 + 31 + 36, 17 + 31 + 37 |
| 32 | 17 + 32 + 33, 17 + 32 + 34, 17 + 32 + 35, 17 + 32 + 36, 17 + 32 + 37 |
| 33 | 17 + 33 + 34, 17 + 33 + 35, 17 + 33 + 36, 17 + 33 + 37 |
| 34 | 17 + 34 + 35, 17 + 34 + 36, 17 + 34 + 37 |
| 35 | 17 + 35 + 36, 17 + 35 + 37 |
| 36 | 17 + 36 + 37 |

TABLE 18

Myrcene family of terpene formulations.
Table 18. Myrcene family of terpene formulations.
The numbers refer to the terpenes from Table 1. The
designation "family" is only for convenience in presentation,
as other tables also include formulations with myrcene.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 19 | 18 + 19 + 20, 18 + 19 + 21, 18 + 19 + 22, 18 + 19 + 23, 18 + 19 + 24, 18 + 19 + 25, 18 + 19 + 26, 18 + 19 + 27, 18 + 19 + 28, 18 + 19 + 29, 18 + 19 + 30, 18 + 19 + 31, 18 + 19 + 32, 18 + 19 + 33, 18 + 19 + 34, 18 + 19 + 35, 18 + 19 + 36, 18 + 19 + 37 |
| 20 | 18 + 20 + 21, 18 + 20 + 22, 18 + 20 + 23, 18 + 20 + 24, 18 + 20 + 25, 18 + 20 + 26, 18 + 20 + 27, 18 + 20 + 28, 18 + 20 + 29, 18 + 20 + 30, 18 + 20 + 31, 18 + 20 + 32, 18 + 20 + 33, 18 + 20 + 34, 18 + 20 + 35, 18 + 20 + 36, 18 + 20 + 37 |

TABLE 18-continued

Myrcene family of terpene formulations.
Table 18. Myrcene family of terpene formulations.
The numbers refer to the terpenes from Table 1. The
designation "family" is only for convenience in presentation,
as other tables also include formulations with myrcene.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 21 | 18 + 21 + 22, 18 + 21 + 23, 18 + 21 + 24, 18 + 21 + 25, 18 + 21 + 26, 18 + 21 + 27, 18 + 21 + 28, 18 + 21 + 29, 18 + 21 + 30, 18 + 21 + 31, 18 + 21 + 32, 18 + 21 + 33, 18 + 21 + 34, 18 + 21 + 35, 18 + 21 + 36, 18 + 21 + 37 |
| 22 | 18 + 22 + 23, 18 + 22 + 24, 18 + 22 + 25, 18 + 22 + 26, 18 + 22 + 27, 18 + 22 + 28, 18 + 22 + 29, 18 + 22 + 30, 18 + 22 + 31, 18 + 22 + 32, 18 + 22 + 33, 18 + 22 + 34, 18 + 22 + 35, 18 + 22 + 36, 18 + 22 + 37 |
| 23 | 18 + 23 + 24, 18 + 23 + 25, 18 + 23 + 26, 18 + 23 + 27, 18 + 23 + 28, 18 + 23 + 29, 18 + 23 + 30, 18 + 23 + 31, 18 + 23 + 32, 18 + 23 + 33, 18 + 23 + 34, 18 + 23 + 35, 18 + 23 + 36, 18 + 23 + 37 |
| 24 | 18 + 24 + 25, 18 + 24 + 26, 18 + 24 + 27, 18 + 24 + 28, 18 + 24 + 29, 18 + 24 + 30, 18 + 24 + 31, 18 + 24 + 32, 18 + 24 + 33, 18 + 24 + 34, 18 + 24 + 35, 18 + 24 + 36, 18 + 24 + 37 |
| 25 | 18 + 25 + 26, 18 + 25 + 27, 18 + 25 + 28, 18 + 25 + 29, 18 + 25 + 30, 18 + 25 + 31, 18 + 25 + 32, 18 + 25 + 33, 18 + 25 + 34, 18 + 25 + 35, 18 + 25 + 36, 18 + 25 + 37 |
| 26 | 18 + 26 + 27, 18 + 26 + 28, 18 + 26 + 29, 18 + 26 + 30, 18 + 26 + 31, 18 + 26 + 32, 18 + 26 + 33, 18 + 26 + 34, 18 + 26 + 35, 18 + 26 + 36, 18 + 26 + 37 |
| 27 | 18 + 27 + 28, 18 + 27 + 29, 18 + 27 + 30, 18 + 27 + 31, 18 + 27 + 32, 18 + 27 + 33, 18 + 27 + 34, 18 + 27 + 35, 18 + 27 + 36, 18 + 27 + 37 |
| 28 | 18 + 28 + 29, 18 + 28 + 30, 18 + 28 + 31, 18 + 28 + 32, 18 + 28 + 33, 18 + 28 + 34, 18 + 28 + 35, 18 + 28 + 36, 18 + 28 + 37 |
| 29 | 18 + 29 + 30, 18 + 29 + 31, 18 + 29 + 32, 18 + 29 + 33, 18 + 29 + 34, 18 + 29 + 35, 18 + 29 + 36, 18 + 29 + 37 |
| 30 | 18 + 30 + 31, 18 + 30 + 32, 18 + 30 + 33, 18 + 30 + 34, 18 + 30 + 35, 18 + 30 + 36, 18 + 30 + 37 |
| 31 | 18 + 31 + 32, 18 + 31 + 33, 18 + 31 + 34, 18 + 31 + 35, 18 + 31 + 36, 18 + 31 + 37 |
| 32 | 18 + 32 + 33, 18 + 32 + 34, 18 + 32 + 35, 18 + 32 + 36, 18 + 32 + 37 |
| 33 | 18 + 33 + 34, 18 + 33 + 35, 18 + 33 + 36, 18 + 33 + 37 |
| 34 | 18 + 34 + 35, 18 + 34 + 36, 18 + 34 + 37 |
| 35 | 18 + 35 + 36, 18 + 35 + 37 |
| 36 | 18 + 36 + 37 |

TABLE 19

Nerol family of terpene formulations.
Table 19. Nerol family of terpene formulations. The numbers refer
to the terpenes from Table 1. The designation "family" is only for
convenience in presentation, as other tables also include
formulations with nerol.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 20 | 19 + 20 + 21, 19 + 20 + 22, 19 + 20 + 23, 19 + 20 + 24, 19 + 20 + 25, 19 + 20 + 26, 19 + 20 + 27, 19 + 20 + 28, 19 + 20 + 29, 19 + 20 + 30, 19 + 20 + 31, 19 + 20 + 32, 19 + 20 + 33, 19 + 20 + 34, 19 + 20 + 35, 19 + 20 + 36, 19 + 20 + 37 |
| 21 | 19 + 21 + 22, 19 + 21 + 23, 19 + 21 + 24, 19 + 21 + 25, 19 + 21 + 26, 19 + 21 + 27, 19 + 21 + 28, 19 + 21 + 29, 19 + 21 + 30, 19 + 21 + 31, 19 + 21 + 32, 19 + 21 + 33, 19 + 21 + 34, 19 + 21 + 35, 19 + 21 + 36, 19 + 21 + 37 |
| 22 | 19 + 22 + 23, 19 + 22 + 24, 19 + 22 + 25, 19 + 22 + 26, 19 + 22 + 27, 19 + 22 + 28, 19 + 22 + 29, 19 + 22 + 30, 19 + 22 + 31, 19 + 22 + 32, 19 + 22 + 33, 19 + 22 + 34, 19 + 22 + 35, 19 + 22 + 36, 19 + 22 + 37 |
| 23 | 19 + 23 + 24, 19 + 23 + 25, 19 + 23 + 26, 19 + 23 + 27, 19 + 23 + 28, 19 + 23 + 29, 19 + 23 + 30, 19 + 23 + 31, 19 + 23 + 32, 19 + 23 + 33, 19 + 23 + 34, 19 + 23 + 35, 19 + 23 + 36, 19 + 23 + 37 |
| 24 | 19 + 24 + 25, 19 + 24 + 26, 19 + 24 + 27, 19 + 24 + 28, 19 + 24 + 29, 19 + 24 + 30, 19 + 24 + 31, 19 + 24 + 32, 19 + 24 + 33, 19 + 24 + 34, 19 + 24 + 35, 19 + 24 + 36, 19 + 24 + 37 |
| 25 | 19 + 25 + 26, 19 + 25 + 27, 19 + 25 + 28, 19 + 25 + 29, 19 + 25 + 30, 19 + 25 + 31, 19 + 25 + 32, 19 + 25 + 33, 19 + 25 + 34, 19 + 25 + 35, 19 + 25 + 36, 19 + 25 + 37 |
| 26 | 19 + 26 + 27, 19 + 26 + 28, 19 + 26 + 29, 19 + 26 + 30, 19 + 26 + 31, 19 + 26 + 32, 19 + 26 + 33, 19 + 26 + 34, 19 + 26 + 35, 19 + 26 + 36, 19 + 26 + 37 |
| 27 | 19 + 27 + 28, 19 + 27 + 29, 19 + 27 + 30, 19 + 27 + 31, 19 + 27 + 32, 19 + 27 + 33, 19 + 27 + 34, 19 + 27 + 35, 19 + 27 + 36, 19 + 27 + 37 |
| 28 | 19 + 28 + 29, 19 + 28 + 30, 19 + 28 + 31, 19 + 28 + 32, 19 + 28 + 33, 19 + 28 + 34, 19 + 28 + 35, 19 + 28 + 36, 19 + 28 + 37 |
| 29 | 19 + 29 + 30, 19 + 29 + 31, 19 + 29 + 32, 19 + 29 + 33, 19 + 29 + 34, 19 + 29 + 35, 19 + 29 + 36, 19 + 29 + 37 |
| 30 | 19 + 30 + 31, 19 + 30 + 32, 19 + 30 + 33, 19 + 30 + 34, 19 + 30 + 35, 19 + 30 + 36, 19 + 30 + 37 |
| 31 | 19 + 31 + 32, 19 + 31 + 33, 19 + 31 + 34, 19 + 31 + 35, 19 + 31 + 36, 19 + 31 + 37 |
| 32 | 19 + 32 + 33, 19 + 32 + 34, 19 + 32 + 35, 19 + 32 + 36, 19 + 32 + 37 |
| 33 | 19 + 33 + 34, 19 + 33 + 35, 19 + 33 + 36, 19 + 33 + 37 |
| 34 | 19 + 34 + 35, 19 + 34 + 36, 19 + 34 + 37 |
| 35 | 19 + 35 + 36, 19 + 35 + 37 |
| 36 | 19 + 36 + 37 |

TABLE 20

Cis-ocimene family of terpene formulations.
Table 20. Cis-ocimene family of terpene formulations.
The numbers refer to the terpenes from Table 1. The designation
"family" is only for convenience in presentation, as
other tables also include formulations with cis-ocimene.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 21 | 20 + 21 + 22, 20 + 21 + 23, 20 + 21 + 24, 20 + 21 + 25, 20 + 21 + 26, 20 + 21 + 27, 20 + 21 + 28, 20 + 21 + 29, 20 + 21 + 30, 20 + 21 + 31, 20 + 21 + 32, 20 + 21 + 33, 20 + 21 + 34, 20 + 21 + 35, 20 + 21 + 36, 20 + 21 + 37 |
| 22 | 20 + 22 + 23, 20 + 22 + 24, 20 + 22 + 25, 20 + 22 + 26, 20 + 22 + 27, 20 + 22 + 28, 20 + 22 + 29, 20 + 22 + 30, 20 + 22 + 31, 20 + 22 + 32, 20 + 22 + 33, 20 + 22 + 34, 20 + 22 + 35, 20 + 22 + 36, 20 + 22 + 37 |
| 23 | 20 + 23 + 24, 20 + 23 + 25, 20 + 23 + 26, 20 + 23 + 27, 20 + 23 + 28, 20 + 23 + 29, 20 + 23 + 30, 20 + 23 + 31, 20 + 23 + 32, 20 + 23 + 33, 20 + 23 + 34, 20 + 23 + 35, 20 + 23 + 36, 20 + 23 + 37 |

TABLE 20-continued

Cis-ocimene family of terpene formulations.
Table 20. Cis-ocimene family of terpene formulations.
The numbers refer to the terpenes from Table 1. The designation "family" is only for convenience in presentation, as other tables also include formulations with cis-ocimene.

| Sub-family | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 24 | 20 + 24 + 25, 20 + 24 + 26, 20 + 24 + 27, 20 + 24 + 28, 20 + 24 + 29, 20 + 24 + 30, 20 + 24 + 31, 20 + 24 + 32, 20 + 24 + 33, 20 + 24 + 34, 20 + 24 + 35, 20 + 24 + 36, 20 + 24 + 37 |
| 25 | 20 + 25 + 26, 20 + 25 + 27, 20 + 25 + 28, 20 + 25 + 29, 20 + 25 + 30, 20 + 25 + 31, 20 + 25 + 32, 20 + 25 + 33, 20 + 25 + 34, 20 + 25 + 35, 20 + 25 + 36, 20 + 25 + 37 |
| 26 | 20 + 26 + 27, 20 + 26 + 28, 20 + 26 + 29, 20 + 26 + 30, 20 + 26 + 31, 20 + 26 + 32, 20 + 26 + 33, 20 + 26 + 34, 20 + 26 + 35, 20 + 26 + 36, 20 + 26 + 37 |
| 27 | 20 + 27 + 28, 20 + 27 + 29, 20 + 27 + 30, 20 + 27 + 31, 20 + 27 + 32, 20 + 27 + 33, 20 + 27 + 34, 20 + 27 + 35, 20 + 27 + 36, 20 + 27 + 37 |
| 28 | 20 + 28 + 29, 20 + 28 + 30, 20 + 28 + 31, 20 + 28 + 32, 20 + 28 + 33, 20 + 28 + 34, 20 + 28 + 35, 20 + 28 + 36, 20 + 28 + 37 |
| 29 | 20 + 29 + 30, 20 + 29 + 31, 20 + 29 + 32, 20 + 29 + 33, 20 + 29 + 34, 20 + 29 + 35, 20 + 29 + 36, 20 + 29 + 37 |
| 30 | 20 + 30 + 31, 20 + 30 + 32, 20 + 30 + 33, 20 + 30 + 34, 20 + 30 + 35, 20 + 30 + 36, 20 + 30 + 37 |
| 31 | 20 + 31 + 32, 20 + 31 + 33, 20 + 31 + 34, 20 + 31 + 35, 20 + 31 + 36, 20 + 31 + 37 |
| 32 | 20 + 32 + 33, 20 + 32 + 34, 20 + 32 + 35, 20 + 32 + 36, 20 + 32 + 37 |
| 33 | 20 + 33 + 34, 20 + 33 + 35, 20 + 33 + 36, 20 + 33 + 37 |
| 34 | 20 + 34 + 35, 20 + 34 + 36, 20 + 34 + 37 |
| 35 | 20 + 35 + 36, 20 + 35 + 37 |
| 36 | 20 + 36 + 37 |

TABLE 21

Trans-ocimene family of terpene formulations.
Table 21. Trans-ocimene family of terpene formulations. The numbers refer to the terpenes from Table 1. The designation "family" is only for convenience in presentation, as other tables also include formulations with trans-ocimene.

| Sub-family | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 22 | 21 + 22 + 23, 21 + 22 + 24, 21 + 22 + 25, 21 + 22 + 26, 21 + 22 + 27, 21 + 22 + 28, 21 + 22 + 29, 21 + 22 + 30, 21 + 22 + 31, 21 + 22 + 32, 21 + 22 + 33, 21 + 22 + 34, 21 + 22 + 35, 21 + 22 + 36, 21 + 22 + 37 |
| 23 | 21 + 23 + 24, 21 + 23 + 25, 21 + 23 + 26, 21 + 23 + 27, 21 + 23 + 28, 21 + 23 + 29, 21 + 23 + 30, 21 + 23 + 31, 21 + 23 + 32, 21 + 23 + 33, 21 + 23 + 34, 21 + 23 + 35, 21 + 23 + 36, 21 + 23 + 37 |
| 24 | 21 + 24 + 25, 21 + 24 + 26, 21 + 24 + 27, 21 + 24 + 28, 21 + 24 + 29, 21 + 24 + 30, 21 + 24 + 31, 21 + 24 + 32, 21 + 24 + 33, 21 + 24 + 34, 21 + 24 + 35, 21 + 24 + 36, 21 + 24 + 37 |
| 25 | 21 + 25 + 26, 21 + 25 + 27, 21 + 25 + 28, 21 + 25 + 29, 21 + 25 + 30, 21 + 25 + 31, 21 + 25 + 32, 21 + 25 + 33, 21 + 25 + 34, 21 + 25 + 35, 21 + 25 + 36, 21 + 25 + 37 |
| 26 | 21 + 26 + 27, 21 + 26 + 28, 21 + 26 + 29, 21 + 26 + 30, 21 + 26 + 31, 21 + 26 + 32, 21 + 26 + 33, 21 + 26 + 34, 21 + 26 + 35, 21 + 26 + 36, 21 + 26 + 37 |
| 27 | 21 + 27 + 28, 21 + 27 + 29, 21 + 27 + 30, 21 + 27 + 31, 21 + 27 + 32, 21 + 27 + 33, 21 + 27 + 34, 21 + 27 + 35, 21 + 27 + 36, 21 + 27 + 37 |
| 28 | 21 + 28 + 29, 21 + 28 + 30, 21 + 28 + 31, 21 + 28 + 32, 21 + 28 + 33, 21 + 28 + 34, 21 + 28 + 35, 21 + 28 + 36, 21 + 28 + 37 |
| 29 | 21 + 29 + 30, 21 + 29 + 31, 21 + 29 + 32, 21 + 29 + 33, 21 + 29 + 34, 21 + 29 + 35, 21 + 29 + 36, 21 + 29 + 37 |
| 30 | 21 + 30 + 31, 21 + 30 + 32, 21 + 30 + 33, 21 + 30 + 34, 21 + 30 + 35, 21 + 30 + 36, 21 + 30 + 37 |
| 31 | 21 + 31 + 32, 21 + 31 + 33, 21 + 31 + 34, 21 + 31 + 35, 21 + 31 + 36, 21 + 31 + 37 |
| 32 | 21 + 32 + 33, 21 + 32 + 34, 21 + 32 + 35, 21 + 32 + 36, 21 + 32 + 37 |
| 33 | 21 + 33 + 34, 21 + 33 + 35, 21 + 33 + 36, 21 + 33 + 37 |
| 34 | 21 + 34 + 35, 21 + 34 + 36, 21 + 34 + 37 |
| 35 | 21 + 35 + 36, 21 + 35 + 37 |
| 36 | 21 + 36 + 37 |

TABLE 22

Alpha-phellandrene family of terpene formulations.
Table 22. Alpha-phellandrene family of terpene formulations. The numbers refer to the terpenes from Table 1. The designation "family" is only for convenience in presentation, as other tables also include formulations with alpha-phellandrene.

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 23 | 22 + 23 + 24, 22 + 23 + 25, 22 + 23 + 26, 22 + 23 + 27, 22 + 23 + 28, 22 + 23 + 29, 22 + 23 + 30, 22 + 23 + 31, 22 + 23 + 32, 22 + 23 + 33, 22 + 23 + 34, 22 + 23 + 35, 22 + 23 + 36, 22 + 23 + 37 |
| 24 | 22 + 24 + 25, 22 + 24 + 26, 22 + 24 + 27, 22 + 24 + 28, 22 + 24 + 29, 22 + 24 + 30, 22 + 24 + 31, 22 + 24 + 32, 22 + 24 + 33, 22 + 24 + 34, 22 + 24 + 35, 22 + 24 + 36, 22 + 24 + 37 |
| 25 | 22 + 25 + 26, 22 + 25 + 27, 22 + 25 + 28, 22 + 25 + 29, 22 + 25 + 30, 22 + 25 + 31, 22 + 25 + 32, 22 + 25 + 33, 22 + 25 + 34, 22 + 25 + 35, 22 + 25 + 36, 22 + 25 + 37 |
| 26 | 22 + 26 + 27, 22 + 26 + 28, 22 + 26 + 29, 22 + 26 + 30, 22 + 26 + 31, 22 + 26 + 32, 22 + 26 + 33, 22 + 26 + 34, 22 + 26 + 35, 22 + 26 + 36, 22 + 26 + 37 |
| 27 | 22 + 27 + 28, 22 + 27 + 29, 22 + 27 + 30, 22 + 27 + 31, 22 + 27 + 32, 22 + 27 + 33, 22 + 27 + 34, 22 + 27 + 35, 22 + 27 + 36, 22 + 27 + 37 |
| 28 | 22 + 28 + 29, 22 + 28 + 30, 22 + 28 + 31, 22 + 28 + 32, 22 + 28 + 33, 22 + 28 + 34, 22 + 28 + 35, 22 + 28 + 36, 22 + 28 + 37 |
| 29 | 22 + 29 + 30, 22 + 29 + 31, 22 + 29 + 32, 22 + 29 + 33, 22 + 29 + 34, 22 + 29 + 35, 22 + 29 + 36, 22 + 29 + 37 |
| 30 | 22 + 30 + 31, 22 + 30 + 32, 22 + 30 + 33, 22 + 30 + 34, 22 + 30 + 35, 22 + 30 + 36, 22 + 30 + 37 |
| 31 | 22 + 31 + 32, 22 + 31 + 33, 22 + 31 + 34, 22 + 31 + 35, 22 + 31 + 36, 22 + 31 + 37 |

TABLE 22-continued

Alpha-phellandrene family of terpene formulations.
Table 22. Alpha-phellandrene family of terpene formulations. The numbers refer to the terpenes from Table 1. The designation "family" is only for convenience in presentation, as other tables also include formulations with alpha-phellandrene.

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 32 | 22 + 32 + 33, 22 + 32 + 34, 22 + 32 + 35, 22 + 32 + 36, 22 + 32 + 37 |
| 33 | 22 + 33 + 34, 22 + 33 + 35, 22 + 33 + 36, 22 + 33 + 37 |
| 34 | 22 + 34 + 35, 22 + 34 + 36, 22 + 34 + 37 |
| 35 | 22 + 35 + 36, 22 + 35 + 37 |
| 36 | 22 + 36 + 37 |

TABLE 23

Alpha-pinene family of terpene formulations.
Table 23. Alpha-pinene family of terpene formulations. The numbers refer to the terpenes from Table 1. The designation "family" is only for convenience in presentation, as other tables also include formulations with alpha-pinene.

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 24 | 23 + 24 + 25, 23 + 24 + 26, 23 + 24 + 27, 23 + 24 + 28, 23 + 24 + 29, 23 + 24 + 30, 23 + 24 + 31, 23 + 24 + 32, 23 + 24 + 33, 23 + 24 + 34, 23 + 24 + 35, 23 + 24 + 36, 23 + 24 + 37 |
| 25 | 23 + 25 + 26, 23 + 25 + 27, 23 + 25 + 28, 23 + 25 + 29, 23 + 25 + 30, 23 + 25 + 31, 23 + 25 + 32, 23 + 25 + 33, 23 + 25 + 34, 23 + 25 + 35, 23 + 25 + 36, 23 + 25 + 37 |
| 26 | 23 + 26 + 27, 23 + 26 + 28, 23 + 26 + 29, 23 + 26 + 30, 23 + 26 + 31, 23 + 26 + 32, 23 + 26 + 33, 23 + 26 + 34, 23 + 26 + 35, 23 + 26 + 36, 23 + 26 + 37 |
| 27 | 23 + 27 + 28, 23 + 27 + 29, 23 + 27 + 30, 23 + 27 + 31, 23 + 27 + 32, 23 + 27 + 33, 23 + 27 + 34, 23 + 27 + 35, 23 + 27 + 36, 23 + 27 + 37 |
| 28 | 23 + 28 + 29, 23 + 28 + 30, 23 + 28 + 31, 23 + 28 + 32, 23 + 28 + 33, 23 + 28 + 34, 23 + 28 + 35, 23 + 28 + 36, 23 + 28 + 37 |
| 29 | 23 + 29 + 30, 23 + 29 + 31, 23 + 29 + 32, 23 + 29 + 33, 23 + 29 + 34, 23 + 29 + 35, 23 + 29 + 36, 23 + 29 + 37 |
| 30 | 23 + 30 + 31, 23 + 30 + 32, 23 + 30 + 33, 23 + 30 + 34, 23 + 30 + 35, 23 + 30 + 36, 23 + 30 + 37 |
| 31 | 23 + 31 + 32, 23 + 31 + 33, 23 + 31 + 34, 23 + 31 + 35, 23 + 31 + 36, 23 + 31 + 37 |
| 32 | 23 + 32 + 33, 23 + 32 + 34, 23 + 32 + 35, 23 + 32 + 36, 23 + 32 + 37 |
| 33 | 23 + 33 + 34, 23 + 33 + 35, 23 + 33 + 36, 23 + 33 + 37 |
| 34 | 23 + 34 + 35, 23 + 34 + 36, 23 + 34 + 37 |
| 35 | 23 + 35 + 36, 23 + 35 + 37 |
| 36 | 23 + 36 + 37 |

TABLE 24

Beta-pinene family of terpene formulations.
Table 24. Beta-pinene family of terpene formulations. The numbers refer to the terpenes from Table 1. The designation "family" is only for convenience in presentation, as other tables also include formulations with beta-pinene.

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 25 | 24 + 25 + 26, 24 + 25 + 27, 24 + 25 + 28, 24 + 25 + 29, 24 + 25 + 30, 24 + 25 + 31, 24 + 25 + 32, 24 + 25 + 33, 24 + 25 + 34, 24 + 25 + 35, 24 + 25 + 36, 24 + 25 + 37 |
| 26 | 24 + 26 + 27, 24 + 26 + 28, 24 + 26 + 29, 24 + 26 + 30, 24 + 26 + 31, 24 + 26 + 32, 24 + 26 + 33, 24 + 26 + 35, 24 + 26 + 36, 24 + 26 + 37 |
| 27 | 24 + 27 + 28, 24 + 27 + 29, 24 + 27 + 30, 24 + 27 + 31, 24 + 27 + 32, 24 + 27 + 33, 24 + 27 + 34, 24 + 27 + 35, 24 + 27 + 36, 24 + 27 + 37 |
| 28 | 24 + 28 + 29, 24 + 28 + 30, 24 + 28 + 31, 24 + 28 + 32, 24 + 28 + 33, 24 + 28 + 34, 24 + 28 + 35, 24 + 28 + 36, 24 + 28 + 37 |
| 29 | 24 + 29 + 30, 24 + 29 + 31, 24 + 29 + 32, 24 + 29 + 33, 24 + 29 + 34, 24 + 29 + 35, 24 + 29 + 36, 24 + 29 + 37 |
| 30 | 24 + 30 + 31, 24 + 30 + 32, 24 + 30 + 33, 24 + 30 + 34, 24 + 30 + 35, 24 + 30 + 36, 24 + 30 + 37 |
| 31 | 24 + 31 + 32, 24 + 31 + 33, 24 + 31 + 34, 24 + 31 + 35, 24 + 31 + 36, 24 + 31 + 37 |
| 32 | 24 + 32 + 33, 24 + 32 + 34, 24 + 32 + 35, 24 + 32 + 36, 24 + 32 + 37 |
| 33 | 24 + 33 + 34, 24 + 33 + 35, 24 + 33 + 36, 24 + 33 + 37 |
| 34 | 24 + 34 + 35, 24 + 34 + 36, 24 + 34 + 37 |
| 35 | 24 + 35 + 36, 24 + 35 + 37 |
| 36 | 24 + 36 + 37 |

TABLE 25

Sabinene family of terpene formulations.
Table 25. Sabinene family of terpene formulations. The numbers refer to the terpenes from Table 1. The designation "family" is only for convenience in presentation, as other tables also include formulations with sabinene.

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 26 | 25 + 26 + 27, 25 + 26 + 28, 25 + 26 + 29, 25 + 26 + 30, 25 + 26 + 31, 25 + 26 + 32, 25 + 26 + 33, 25 + 26 + 34, 25 + 26 + 35, 25 + 26 + 36, 25 + 26 + 37 |
| 27 | 25 + 27 + 28, 25 + 27 + 29, 25 + 27 + 30, 25 + 27 + 31, 25 + 27 + 32, 25 + 27 + 33, 25 + 27 + 34, 25 + 27 + 35, 25 + 27 + 36, 25 + 27 + 37 |
| 28 | 25 + 28 + 29, 25 + 28 + 30, 25 + 28 + 31, 25 + 28 + 32, 25 + 28 + 33, 25 + 28 + 34, 25 + 28 + 35, 25 + 28 + 36, 25 + 28 + 37 |
| 29 | 25 + 29 + 30, 25 + 29 + 31, 25 + 29 + 32, 25 + 29 + 33, 25 + 29 + 34, 25 + 29 + 35, 25 + 29 + 36, 25 + 29 + 37 |
| 30 | 25 + 30 + 31, 25 + 30 + 32, 25 + 30 + 33, 25 + 30 + 34, 25 + 30 + 35, 25 + 30 + 36, 25 + 30 + 37 |

TABLE 25-continued

Sabinene family of terpene formulations.
Table 25. Sabinene family of terpene formulations. The numbers refer to the terpenes from Table 1. The designation "family" is only for convenience in presentation, as other tables also include formulations with sabinene.

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 31 | 25 + 31 + 32, 25 + 31 + 33, 25 + 31 + 34, 25 + 31 + 35, 25 + 31 + 36, 25 + 31 + 37 |
| 32 | 25 + 32 + 33, 25 + 32 + 34, 25 + 32 + 35, 25 + 32 + 36, 25 + 32 + 37 |
| 33 | 25 + 33 + 34, 25 + 33 + 35, 25 + 33 + 36, 25 + 33 + 37 |
| 34 | 25 + 34 + 35, 25 + 34 + 36, 25 + 34 + 37 |
| 35 | 25 + 35 + 36, 25 + 35 + 37 |
| 36 | 25 + 36 + 37 |

TABLE 26

Alpha-terpinene family of terpene formulations.
Table 26. Alpha-terpinene family of terpene formulations. The numbers refer to the terpenes from Table 1. The designation "family" is only for convenience in presentation, as other tables also include formulations with alpha-terpinene.

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 27 | 26 + 27 + 28, 26 + 27 + 29, 26 + 27 + 30, 26 + 27 + 31, 26 + 27 + 32, 26 + 27 + 33, 26 + 27 + 34, 26 + 27 + 35, 26 + 27 + 36, 26 + 27 + 37 |
| 28 | 26 + 28 + 29, 26 + 28 + 30, 26 + 28 + 31, 26 + 28 + 32, 26 + 28 + 33, 26 + 28 + 34, 26 + 28 + 35, 26 + 28 + 36, 26 + 28 + 37 |
| 29 | 26 + 29 + 30, 26 + 29 + 31, 26 + 29 + 32, 26 + 29 + 33, 26 + 29 + 34, 26 + 29 + 35, 26 + 29 + 36, 26 + 29 + 37 |
| 30 | 26 + 30 + 31, 26 + 30 + 32, 26 + 30 + 33, 26 + 30 + 34, 26 + 30 + 35, 26 + 30 + 36, 26 + 30 + 37 |
| 31 | 26 + 31 + 32, 26 + 31 + 33, 26 + 31 + 34, 26 + 31 + 35, 26 + 31 + 36, 26 + 31 + 37 |
| 32 | 26 + 32 + 33, 26 + 32 + 34, 26 + 32 + 35, 26 + 32 + 36, 26 + 32 + 37 |
| 33 | 26 + 33 + 34, 26 + 33 + 35, 26 + 33 + 36, 26 + 33 + 37 |
| 34 | 26 + 34 + 35, 26 + 34 + 36, 26 + 34 + 37 |
| 35 | 26 + 35 + 36, 26 + 35 + 37 |
| 36 | 26 + 36 + 37 |

TABLE 27

Alpha-terpineol family of terpene formulations.
Table 27. Alpha-terpineol family of terpene formulations. The numbers refer to the terpenes from Table 1. The designation "family" is only for convenience in presentation, as other tables also include formulations with alpha-terpineol.

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 28 | 27 + 28 + 29, 27 + 28 + 30, 27 + 28 + 31, 27 + 28 + 32, 27 + 28 + 33, 27 + 28 + 34, 27 + 28 + 35, 27 + 28 + 36, 27 + 28 + 37 |
| 29 | 27 + 29 + 30, 27 + 29 + 31, 27 + 29 + 32, 27 + 29 + 33, 27 + 29 + 34, 27 + 29 + 35, 27 + 29 + 36, 27 + 29 + 37 |
| 30 | 27 + 30 + 31, 27 + 30 + 32, 27 + 30 + 33, 27 + 30 + 34, 27 + 30 + 35, 27 + 30 + 36, 27 + 30 + 37 |
| 31 | 27 + 31 + 32, 27 + 31 + 33, 27 + 31 + 34, 27 + 31 + 35, 27 + 31 + 36, 27 + 31 + 37 |
| 32 | 27 + 32 + 33, 27 + 32 + 34, 27 + 32 + 35, 27 + 32 + 36, 27 + 32 + 37 |
| 33 | 27 + 33 + 34, 27 + 33 + 35, 27 + 33 + 36, 27 + 33 + 37 |
| 34 | 27 + 34 + 35, 27 + 34 + 36, 27 + 34 + 37 |
| 35 | 27 + 35 + 36, 27 + 35 + 37 |
| 36 | 27 + 36 + 37 |

TABLE 28

Terpinolene family of terpene formulations.
Table 28. Terpinolene family of terpene formulations. The numbers refer to the terpenes from Table 1. The designation "family" is only for convenience in presentation, as other tables also include formulations with terpinolene.

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 29 | 28 + 29 + 30, 28 + 29 + 31, 28 + 29 + 32, 28 + 29 + 33, 28 + 29 + 34, 28 + 29 + 35, 28 + 29 + 36, 28 + 29 + 37 |
| 30 | 28 + 30 + 31, 28 + 30 + 32, 28 + 30 + 33, 28 + 30 + 34, 28 + 30 + 35, 28 + 30 + 36, 28 + 30 + 37 |
| 31 | 28 + 31 + 32, 28 + 31 + 33, 28 + 31 + 34, 28 + 31 + 35, 28 + 31 + 36, 28 + 31 + 37 |
| 32 | 28 + 32 + 33, 28 + 32 + 34, 28 + 32 + 35, 28 + 32 + 36, 28 + 32 + 37 |
| 33 | 28 + 33 + 34, 28 + 33 + 35, 28 + 33 + 36, 28 + 33 + 37 |
| 34 | 28 + 34 + 35, 28 + 34 + 36, 28 + 34 + 37 |
| 35 | 28 + 35 + 36, 28 + 35 + 37 |
| 36 | 28 + 36 + 37 |

TABLE 29

Alpha-guaiene family of terpene formulations.
Table 29. Alpha-guaiene family of terpene formulations. The numbers refer to the terpenes from Table 1. The designation "family" is only for convenience in presentation, as other tables also include formulations with alpha-guaiene.

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 30 | 29 + 30 + 31, 29 + 30 + 32, 29 + 30 + 33, 29 + 30 + 34, 29 + 30 + 35, 29 + 30 + 36, 29 + 30 + 37 |
| 31 | 29 + 31 + 32, 29 + 31 + 33, 29 + 31 + 34, 29 + 31 + 35, 29 + 31 + 36, 29 + 31 + 37 |
| 32 | 29 + 32 + 33, 29 + 32 + 34, 29 + 32 + 35, 29 + 32 + 36, 29 + 32 + 37 |
| 33 | 29 + 33 + 34, 29 + 33 + 35, 29 + 33 + 36, 29 + 33 + 37 |
| 34 | 29 + 34 + 35, 29 + 34 + 36, 29 + 34 + 37 |
| 35 | 29 + 35 + 36, 29 + 35 + 37 |
| 36 | 29 + 36 + 37 |

TABLE 30

Elemene family of terpene formulations.
Table 30. Elemene family of terpene formulations. The numbers refer to the terpenes from Table 1. The designation "family" is only for convenience in presentation, as other Subfamily tables also include formulations with elemene.

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 31 | 30 + 31 + 32, 30 + 31 + 33, 30 + 31 + 34, 30 + 31 + 35, 30 + 31 + 36, 30 + 31 + 37 |
| 32 | 30 + 32 + 33, 30 + 32 + 34, 30 + 32 + 35, 30 + 32 + 36, 30 + 32 + 37 |
| 33 | 30 + 33 + 34, 30 + 33 + 35, 30 + 33 + 36, 30 + 33 + 37 |
| 34 | 30 + 34 + 35, 30 + 34 + 36, 30 + 34 + 37 |
| 35 | 30 + 35 + 36, 30 + 35 + 37 |
| 36 | 30 + 36 + 37 |

TABLE 31

Farnesene family of terpene formulations.
Table 31. Farnesene family of terpene formulations. The numbers refer to the terpenes from Table 1. The designation "family" is only for convenience in presentation, as other tables also include formulations with farnesene.

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 32 | 31 + 32 + 33, 31 + 32 + 34, 31 + 32 + 35, 31 + 32 + 36, 31 + 32 + 37 |
| 33 | 31 + 33 + 34, 31 + 33 + 35, 31 + 33 + 36, 31 + 33 + 37 |
| 34 | 31 + 34 + 35, 31 + 34 + 36, 31 + 34 + 37 |
| 35 | 31 + 35 + 36, 31 + 35 + 37 |
| 36 | 31 + 36 + 37 |

TABLE 32

Germacrene B family of terpene formulations.
Table 32. Germacrene B family of terpene formulations. The numbers refer to the terpenes from Table 1. The designation "family" is only for convenience in presentation, as other tables also include formulations with germacrene B.

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 33 | 32 + 33 + 34, 32 + 33 + 35, 32 + 33 + 36, 32 + 33 + 37 |
| 34 | 32 + 34 + 35, 32 + 34 + 36, 32 + 34 + 37 |
| 35 | 32 + 35 + 36, 32 + 35 + 37 |
| 36 | 32 + 36 + 37 |

TABLE 33

Guaia-1(10),11-diene family of terpene formulations.
Table 33. Guaia-1(10),11-diene family of terpene formulations. The numbers refer to the terpenes from Table 1. The designation "family" is only for convenience in presentation, as other tables also include formulations with Guaia-1(10),11-diene.

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 34 | 33 + 34 + 35, 33 + 34 + 36, 33 + 34 + 37 |
| 35 | 33 + 35 + 36, 33 + 35 + 37 |
| 36 | 33 + 36 + 37 |

TABLE 34

Trans-2-pinanol family of terpene formulations.
Table 34. Trans-2-pinanol family of terpene formulations. The numbers refer to the terpenes from Table 1. The designation "family" is only for convenience in presentation, as other tables also include formulations with Trans-2-pinanol.

| Subfamily | Each disclosure of three terpenes represents a distinct formulation. In one embodiment, the formulation that is described by the indicated mixture of the three terpenes does not include any additional terpenes. In other embodiments, Subfamily it does include additional terpenes. |
|---|---|
| 35 | 34 + 35 + 36, 34 + 35 + 37 |
| 36 | 34 + 36 + 37 |

TABLE 35

Selina-3, 7(11)-diene family of terpene formulations.
Table 35. Selina-3, 7(11)-diene family of terpene formulations. The numbers refer to the terpenes from Table 1. The designation "family" is only for convenience in presentation, as other tables also include formulations with Selina-3, 7(11)-diene.

| Subfamily | Each disclosure of three terpenes represents a distinct formulation. In one embodiment, the formulation that is described by the indicated mixture of the three terpenes does not include any additional terpenes. In other embodiments, it does include additional terpenes. |
|---|---|
| 36 | 35 + 36 + 37 |

TABLE 36 Eudesm-7(11)-en-4-ol family. All members of this 36 family are disclosed in the above tables. This means that all possible combinations of three different terpenes, where one of the terpenes is eudesm-7(11)-en-4-ol, are disclosed above.

TABLE 37 Valencene family. All members of this family are 37 disclosed in the above tables. This means that all possible combinations of three different terpenes, where one of the terpenes is valencene, are disclosed above. Non-limiting percentage values (wt./vol.) for three members of any terpene trio are disclosed below. The values listed below are not with respect to the order of terpenes, in any given terpene trio that is disclosed elsewhere in Tables 2-37.

Formulations Consisting of a Terpene Trio and One or More Other Terpenes

The present disclosure provides a composition that comprises a formulation that consists of a terpene trio, as disclosed in Tables 1-37, plus one or more additional terpenes, where none of the one or more additional terpenes are in the trio. This one or more additional terpenes are referred to as "other terpenes." In non-limiting embodiments, the present disclosure provides a composition that is:

1 part trio (wt./vol.) and 0.0 parts other terpenes (wt./vol.); 1 part trio (wt./vol.) and 0.0-0.1 parts other terpenes (wt./vol.); 1 part trio (wt./vol.) and 0.1 parts other terpenes (wt./vol.); 1 part trio (wt./vol.) and 0.2 parts other terpenes (wt./vol.); 1 part trio (wt./vol.) and 0.3 parts other terpenes (wt./vol.); 1 part trio (wt./vol.) and 0.4 parts other terpenes (wt./vol.); 1 part trio (wt./vol.) and 0.5 parts other terpenes (wt./vol.); 1 part trio (wt./vol.) and 0.6 parts other terpenes (wt./vol.); 1 part trio (wt./vol.) and 0.7 parts other terpenes (wt./vol.); 1 part trio (wt./vol.) and 0.8 parts other terpenes (wt./vol.); 1 part trio (wt./vol.) and 0.9 parts other terpenes (wt./vol.); 1 part trio (wt./vol.) and 1.0 parts other terpenes (wt./vol.); 1 part trio (wt./vol.) and 1.5 parts other terpenes (wt./vol.); 1 part trio (wt./vol.) and 2.0 parts other terpenes (wt./vol.); 1 part trio (wt./vol.) and 2.5 parts other terpenes (wt./vol.); 1 part trio (wt./vol.) and 3.0 parts other terpenes (wt./vol.); 1 part trio (wt./vol.) and 3.5 parts other terpenes (wt./vol.); 1 part trio (wt./vol.) and 4.0 parts other terpenes (wt./vol.); 1 part trio (wt./vol.) and 4.5 parts other terpenes (wt./vol.); 1 part trio (wt./vol.) and 5.0 parts other terpenes (wt./vol.); 1 part trio (wt./vol.) and 5.5 parts other terpenes (wt./vol.); 1 part trio (wt./vol.) and 6.0 parts other terpenes (wt./vol.); 1 part trio (wt./vol.) and 6.5 parts other terpenes (wt./vol.); 1 part trio (wt./vol.) and 7.0 parts other terpenes (wt./vol.); 1 part trio (wt./vol.) and 7.5 parts other terpenes (wt./vol.); 1 part trio (wt./vol.) and 8.0 parts other terpenes (wt./vol.); 1 part trio (wt./vol.) and 8.5 parts other terpenes (wt./vol.); 1 part trio (wt./vol.) and 9.0 parts other terpenes (wt./vol.); 1 part trio (wt./vol.) and 9.5 parts other terpenes (wt./vol.); 1 part trio (wt./vol.) and 10.0 parts other terpenes (wt./vol.); and the like.

The following embodiments track the above embodiments, but with ranges: 1 part trio (wt./vol.) and 0.1-0.2 parts other terpenes (wt./vol.); 1 part trio (wt./vol.) and 0.2-0.3 parts other terpenes (wt./vol.); 1 part trio (wt./vol.) and 0.3-0.4 parts other terpenes (wt./vol.); 1 part trio (wt./vol.) and 0.4-0.5 parts other terpenes (wt./vol.); 1 part trio (wt./vol.) and 0.5-0.6 parts other terpenes (wt./vol.); 1 part trio (wt./vol.) and 0.6-0.7 parts other terpenes (wt./vol.); 1 part trio (wt./vol.) and 0.7-0.8 parts other terpenes (wt./vol.); 1 part trio (wt./vol.) and 0.8-0.9 parts other terpenes (wt./vol.); 1 part trio (wt./vol.) and 0.9-1.0 parts other terpenes (wt./vol.); 1 part trio (wt./vol.) and 1.0-1.5 parts other terpenes (wt./vol.); 1 part trio (wt./vol.) and 1.5-2.0 parts other terpenes (wt./vol.); 1 part trio (wt./vol.) and 2.0-2.5 parts other terpenes (wt./vol.); 1 part trio (wt./vol.) and 2.5-3.0 parts other terpenes (wt./vol.); 1 part trio (wt./vol.) and 3.0-3.5 parts other terpenes (wt./vol.); 1 part trio (wt./vol.) and 3.5-4.0 parts other terpenes (wt./vol.); 1 part trio (wt./vol.) and 4.0-4.5 parts other terpenes (wt./vol.); 1 part trio (wt./vol.) and 4.5-5.0 parts other terpenes (wt./vol.); 1 part trio (wt./vol.) and 5.0-5.5 parts other terpenes (wt./vol.); 1 part trio (wt./vol.) and 5.5-6.0 parts other terpenes (wt./vol.); 1 part trio (wt./vol.) and 6.0-6.5 parts other terpenes (wt./vol.); 1 part trio (wt./vol.) and 6.5-7.0 parts other terpenes (wt./vol.); 1 part trio (wt./vol.) and 7.0-7.5 parts other terpenes (wt./vol.); 1 part trio (wt./vol.) and 7.5-8.0 parts other terpenes (wt./vol.); 1 part trio (wt./vol.) and 8.0-8.5 parts other terpenes (wt./vol.); 1 part trio (wt./vol.) and 8.5-9.0 parts other terpenes (wt./vol.); 1 part trio (wt./vol.) and 9.0-9.5 parts other terpenes (wt./vol.); 1 part trio (wt./vol.) and 9.5-10.0 parts other terpenes (wt./vol.); 1 part trio (wt./vol.) and 10.0-10.5 parts other terpenes (wt./vol.); and the like.

Ratios of the Three Terpenes in the Terpene Trio

In non-limiting embodiments, the present disclosure encompasses a composition that comprises a formulation that includes a terpene trio, e.g., terpene A, terpene B, and terpene C. The designations, A, B, and C, and the affiliated percentages (wt./vol.) do not imply any particular relationship with the terpene trios disclosed above. In other words, the designation "A (10%), B (15%), C (75%)," can be used to refer to each of the following formulations. The goal of this narrative is only to explain the versatility of the "A (xx %), B (xx %), C (xx %)," terminology, in applying the following table for describing terpene trios.

Beta-caryophyllene (10%); limonene (15%); and myrcene (75%).

Beta-caryophyllene (10%); myrcene (15%); and limonene (75%).

Limonene (10%); beta-caryophyllene (15%); and myrcene (75%).

Myrcene (10%); beta-caryophyllene (15%); and limonene (75%).

Myrcene (10%); limonene (15%); and beta-caryophyllene (75%).

Limonene (10%); myrcene (15%); and beta-caryophllene (75%).

The following table (Table 38) can be used to assign percentage values to any terpene trio. In other words, the following table is not limited to terpene trios that consist of beta-caryophyllene; limonene; and myrcene.

TABLE 38

Percentage values (wt./vol.) for three members of any terpene trio. The values listed below are not with respect to the order of terpenes, in any given terpene trio that is disclosed elsewhere in this specification.

| A | B | C | A | B | C | A | B | C | A | B | C |
|---|---|---|---|---|---|---|---|---|---|---|---|
| 2 | 5 | 93 | 2 | 10 | 88 | 2 | 15 | 83 | 2 | 20 | 78 |
| 4 | 5 | 91 | 4 | 10 | 86 | 4 | 15 | 81 | 4 | 20 | 76 |
| 5 | 5 | 90 | 5 | 10 | 85 | 5 | 15 | 80 | 5 | 20 | 75 |
| 6 | 5 | 89 | 6 | 10 | 84 | 6 | 15 | 79 | 6 | 20 | 74 |
| 8 | 5 | 87 | 8 | 10 | 82 | 8 | 15 | 77 | 8 | 20 | 72 |
| 10 | 5 | 85 | 10 | 10 | 80 | 10 | 15 | 75 | 10 | 20 | 70 |
| 12 | 5 | 83 | 12 | 10 | 78 | 12 | 15 | 73 | 12 | 20 | 68 |
| 14 | 5 | 81 | 14 | 10 | 76 | 14 | 15 | 71 | 14 | 20 | 66 |
| 16 | 5 | 79 | 16 | 10 | 74 | 16 | 15 | 69 | 16 | 20 | 64 |
| 18 | 5 | 77 | 18 | 10 | 72 | 18 | 15 | 67 | 18 | 20 | 62 |
| 20 | 5 | 75 | 20 | 10 | 70 | 20 | 15 | 65 | 20 | 20 | 60 |
| 25 | 5 | 70 | 25 | 10 | 65 | 25 | 15 | 60 | 25 | 20 | 55 |
| 30 | 5 | 65 | 30 | 10 | 60 | 30 | 15 | 55 | 30 | 20 | 50 |

TABLE 38-continued

Percentage values (wt./vol.) for three members of any terpene trio. The values listed below are not with respect to the order of terpenes, in any given terpene trio that is disclosed elsewhere in this specification.

| 35 | 5  | 60 | 35 | 10 | 55 | 35 | 15 | 50 | 35 | 20 | 45 |
|----|----|----|----|----|----|----|----|----|----|----|----|
| 40 | 5  | 55 | 40 | 10 | 50 | 40 | 15 | 45 | 40 | 20 | 40 |
| 45 | 5  | 50 | 45 | 10 | 45 | 45 | 15 | 40 | 45 | 20 | 35 |
| 50 | 5  | 45 | 50 | 10 | 40 | 50 | 15 | 35 | 50 | 20 | 30 |

| A  | B  | C  | A  | B  | C  | A  | B  | C  | A  | B  | C  |
|----|----|----|----|----|----|----|----|----|----|----|----|
| 2  | 25 | 73 | 2  | 30 | 68 | 2  | 35 | 63 | 2  | 40 | 58 |
| 4  | 25 | 71 | 4  | 30 | 66 | 4  | 35 | 61 | 4  | 40 | 56 |
| 5  | 25 | 70 | 5  | 30 | 65 | 5  | 35 | 60 | 5  | 40 | 55 |
| 6  | 25 | 69 | 6  | 30 | 64 | 6  | 35 | 59 | 6  | 40 | 54 |
| 8  | 25 | 67 | 8  | 30 | 62 | 8  | 35 | 57 | 8  | 40 | 52 |
| 10 | 25 | 65 | 10 | 30 | 60 | 10 | 35 | 55 | 10 | 40 | 50 |
| 12 | 25 | 63 | 12 | 30 | 58 | 12 | 35 | 53 | 12 | 40 | 48 |
| 14 | 25 | 61 | 14 | 30 | 56 | 14 | 35 | 51 | 14 | 40 | 46 |
| 16 | 25 | 59 | 16 | 30 | 54 | 16 | 35 | 49 | 16 | 40 | 44 |
| 18 | 25 | 57 | 18 | 30 | 52 | 18 | 35 | 47 | 18 | 40 | 42 |
| 20 | 25 | 55 | 20 | 30 | 50 | 20 | 35 | 45 | 20 | 40 | 40 |
| 25 | 25 | 50 | 25 | 30 | 45 | 25 | 35 | 40 | 25 | 40 | 35 |
| 30 | 25 | 45 | 30 | 30 | 40 | 30 | 35 | 35 | 30 | 40 | 30 |
| 35 | 25 | 40 | 35 | 30 | 35 | 35 | 35 | 30 | 35 | 40 | 25 |
| 40 | 25 | 35 | 40 | 30 | 30 | 40 | 35 | 25 | 40 | 40 | 20 |
| 45 | 25 | 30 | 45 | 30 | 25 | 45 | 35 | 20 | 45 | 40 | 15 |
| 50 | 25 | 25 | 50 | 30 | 20 | 50 | 35 | 15 | 50 | 40 | 10 |

| A | B  | C  | A  | B  | C  | A  | B  | C  | A  | B  | C  |
|---|----|----|----|----|----|----|----|----|----|----|----|
| 2 | 45 | 53 | 10 | 45 | 45 | 20 | 45 | 35 | 45 | 45 | 10 |
| 4 | 45 | 51 | 12 | 45 | 43 | 25 | 45 | 30 | 50 | 45 | 5  |
| 5 | 45 | 50 | 14 | 45 | 41 | 30 | 45 | 25 |    |    |    |
| 6 | 45 | 49 | 16 | 45 | 39 | 35 | 45 | 20 |    |    |    |
| 8 | 45 | 47 | 18 | 45 | 37 | 40 | 45 | 15 |    |    |    |

What is encompassed by the present disclosure are terpene trios of the disclosed values. What is also encompassed are values that are "approximately" the disclosed values. What is further encompassed are values that are in a range halfway between the immediately preceding value and the immediately succeeding value. Redundancies in this table are for stylistic reasons.

While the method and apparatus have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference.

Finally, all references listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant.

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC .sctn.132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

What is claimed is:

1. A prepared composition comprising:
   (i) myrcene present in 11-21% by mass of the prepared composition,
   (ii) alpha-pinene present in 5-35% by mass of the prepared composition, and
   (iii) one terpene or terpenoid selected from the group consisting of alpha-bisabolol, borneol, beta-caryophyllene, camphene, camphor, delta-3-carene, caryophyllene oxide, alpha-cedrene, beta-eudesmol, fenchol, geraniol, guaiol, isoborneol, limonene, linalool, menthol, nerol, cis-ocimene, trans-ocimene, alpha-phellandrene, alpha-humulene, beta-pinene, sabinene, alpha-terpinene, alpha-terpineol, terpinolene, alpha-guaiene, elemene, farnesene, germacrene, guaia-1(10),11-diene, trans-2-pinanol, selina-3,7(11)-diene, eudesm-7(11)-en-4-ol, and valencene.

2. The prepared composition according to claim 1, wherein the composition further comprises one or more modifiers selected from the group consisting of a thiol, a sulfur compound, an ester, a ketone, an aldehyde, a cannabinoid, and a combination thereof.

3. The prepared composition according to claim 1, wherein the myrcene, the alpha-humulene, and the one terpene or terpenoid is purified from a synthetic source.

4. The prepared composition according to claim 1, wherein the one terpene or terpenoid in (iii) is selected from the group consisting of linalool, geraniol, beta-caryophyllene, and elemene.

5. The prepared composition according to claim 1, comprising myrcene, and alpha-humulene.

6. A formulation comprising:
(i) the prepared composition according to claim 5, and
(ii) at least one or more additional terpenes or terpenoids selected from the group consisting of alpha-bisabolol, borneol, beta-caryophyllene, camphene, camphor, delta-3-carene, caryophyllene oxide, alpha-cedrene, beta-eudesmol, fenchol, geraniol, guaiol, isoborneol, limonene, linalool, menthol, nerol, cis-ocimene, trans-ocimene, alpha-phellandrene, alpha-pinene, beta-pinene, sabinene, alpha-terpinene, alpha-terpineol, terpinolene, alpha-guaiene, elemene, farnesene, germacrene, guaia-1(10), 11-diene, trans-2-pinanol, selina-3,7(11)-diene, eudesm-7(11)-en-4-ol, and valencene.

7. The formulation according to claim 6, wherein the composition further comprises one or more modifiers selected from the group consisting of a thiol, a sulfur compound, an ester, a ketone, an aldehyde, a cannabinoid, and a combination thereof.

8. The formulation according to claim 6, wherein the at least one or more additional terpenes or terpenoids is from a synthetic source.

9. The formulation according to claim 6, wherein the at least one or more additional terpenes or terpenoids is selected from the group consisting of linalool, geraniol, beta-caryophyllene, and nerol.

10. The formulation according to claim 6, wherein the at least one or more additional terpenes or terpenoids is alpha-humulene.

11. The formulation according to claim 6, wherein the at least one or more additional terpenes or terpenoids is beta-caryophyllene.

12. The formulation according to claim 6, wherein the at least one or more additional terpenes or terpenoids is linalool.

13. The formulation according to claim 6, wherein the at least one or more additional terpenes or terpenoids is geraniol.

14. The formulation according to claim 6, wherein the at least one or more additional terpenes or terpenoids is elemene.

15. The formulation according to claim 6, wherein the at least one or more additional terpenes or terpenoids are pinene and linalool.

16. The formulation according to claim 6, wherein the at least one or more additional terpenes or terpenoids are pinene and geraniol.

17. The formulation according to claim 6, wherein the at least one or more additional terpenes or terpenoids are beta-caryophyllene and elemene.

18. The formulation according to claim 6, wherein the at least one or more additional terpenes or terpenoids is not limonene.

19. The formulation according to claim 6, wherein the prepared composition comprises at least 2% (wt./vol.) to at least 98% (wt./vol.) of the formulation.

20. A container comprising the formulation according to claim 19.

21. A container comprising the prepared composition according to claim 1.

* * * * *